United States Patent
Gremyachinskiy et al.

(10) Patent No.: US 11,203,612 B2
(45) Date of Patent: Dec. 21, 2021

(54) METHODS OF GENERATING NANOARRAYS AND MICROARRAYS

(71) Applicant: NAUTILUS BIOTECHNOLOGY, INC., Seattle, WA (US)

(72) Inventors: Dmitriy Gremyachinskiy, Sunnyvale, CA (US); Rachel Galimidi, Belmont, CA (US); Parag Mallick, San Mateo, CA (US); Sujal M. Patel, Seattle, WA (US)

(73) Assignee: Nautilus Biotechnology, Inc., Seattle, WA (US)

( * ) Notice: Subject to any disclaimer, the term of this patent is extended or adjusted under 35 U.S.C. 154(b) by 0 days.

(21) Appl. No.: 17/062,405

(22) Filed: Oct. 2, 2020

(65) Prior Publication Data
US 2021/0101930 A1   Apr. 8, 2021

Related U.S. Application Data

(63) Continuation of application No. PCT/US2019/025909, filed on Apr. 4, 2019.

(60) Provisional application No. 62/652,849, filed on Apr. 4, 2018.

(51) Int. Cl.
C12Q 1/68 (2018.01)
C07K 1/04 (2006.01)
C12Q 1/6837 (2018.01)
G01N 33/543 (2006.01)

(52) U.S. Cl.
CPC ............ *C07K 1/047* (2013.01); *C12Q 1/6837* (2013.01); *G01N 33/54353* (2013.01)

(58) Field of Classification Search
USPC ........ 435/6.1, 6.11, 6.12, 91, 1, 91.2, 91.51, 435/287.1, 287.2; 436/94, 501; 536/23.1, 24.3, 24.33, 25.3
See application file for complete search history.

(56) References Cited

U.S. PATENT DOCUMENTS

| | | | |
|---|---|---|---|
| 5,445,934 A | 8/1995 | Fodor et al. | |
| 5,849,878 A * | 12/1998 | Cantor | C07K 16/2809 530/391.9 |
| 6,720,595 B2 | 4/2004 | Clevenger et al. | |
| 6,998,241 B2 | 2/2006 | Boga | |

(Continued)

FOREIGN PATENT DOCUMENTS

| | | |
|---|---|---|
| CN | 100500865 C | 6/2009 |
| EP | 2872898 B1 | 12/2016 |

(Continued)

OTHER PUBLICATIONS

Riccelli et al., Hybridization of single-stranded DNA targets to immobilized complementary DNA probes: comparison of hairpin versus linear capture probes. Nucleic Acids Research, 29, 996-1004, 2001.*

(Continued)

*Primary Examiner* — Frank W Lu

(74) *Attorney, Agent, or Firm* — Wilson Sonsini Goodrich & Rosati

(57) ABSTRACT

The methods described herein provide a means of producing an array of spatially separated proteins. The method relies on covalently attaching each protein of the plurality of proteins to a structured nucleic acid particle (SNAP), and attaching the SNAPs to a solid support.

25 Claims, 32 Drawing Sheets

Specification includes a Sequence Listing.

(56) References Cited

U.S. PATENT DOCUMENTS

| | | | |
|---|---|---|---|
| 7,252,954 | B2 | 8/2007 | Wang et al. |
| 7,842,793 | B2 | 11/2010 | Rothemund |
| 7,932,060 | B2 | 4/2011 | Nadeau et al. |
| 8,501,923 | B2 | 8/2013 | Rothemund |
| 9,340,416 | B2 | 5/2016 | Maune et al. |
| 9,528,984 | B2 | 12/2016 | Mitra |
| 9,880,175 | B2 | 1/2018 | Mitra |
| 10,175,248 | B2 | 1/2019 | Mitra |
| 10,351,909 | B2* | 7/2019 | Drmanac ........... G01N 15/1434 |
| 10,473,654 | B1 | 11/2019 | Mallick |
| 10,571,473 | B2 | 2/2020 | Mitra |
| 10,741,382 | B2 | 8/2020 | Sills et al. |
| 10,829,816 | B2 | 11/2020 | Staker et al. |
| 10,921,317 | B2 | 2/2021 | Mallick |
| 10,948,488 | B2 | 3/2021 | Mallick |
| 2003/0054408 | A1 | 3/2003 | Ravi et al. |
| 2004/0023413 | A1 | 2/2004 | Opalsky |
| 2004/0091931 | A1 | 5/2004 | Gold |
| 2004/0166106 | A1 | 8/2004 | Wang et al. |
| 2006/0160234 | A1 | 7/2006 | Lopez-Avila et al. |
| 2006/0263769 | A1* | 11/2006 | Luo .................... C12Q 1/6837 435/5 |
| 2007/0188750 | A1 | 8/2007 | Lundquist et al. |
| 2007/0218503 | A1 | 9/2007 | Mitra |
| 2009/0214591 | A1 | 8/2009 | Manucharyan |
| 2011/0065807 | A1* | 3/2011 | Radovic-Moreno ........................ C12N 15/115 514/772.3 |
| 2011/0263688 | A1 | 10/2011 | Barany et al. |
| 2012/0077688 | A1* | 3/2012 | Bergo ................ G01N 33/5308 506/9 |
| 2015/0160204 | A1 | 6/2015 | Mitra |
| 2015/0185199 | A1 | 7/2015 | Joo et al. |
| 2015/0330974 | A1 | 11/2015 | Staker et al. |
| 2016/0102344 | A1* | 4/2016 | Niemeyer ........ C12Q 2565/501 506/9 |
| 2016/0310926 | A1 | 10/2016 | Sun et al. |
| 2017/0044245 | A1 | 2/2017 | Meng et al. |
| 2017/0175184 | A1 | 6/2017 | Drmanac et al. |
| 2017/0191051 | A1 | 7/2017 | Nikiforov |
| 2017/0283868 | A1 | 10/2017 | Beechem et al. |
| 2019/0204339 | A1 | 7/2019 | Mitra |
| 2020/0025752 | A1 | 1/2020 | Gopinath et al. |
| 2020/0025757 | A1 | 1/2020 | Gopinath et al. |
| 2020/0158722 | A1 | 5/2020 | Mallick |
| 2020/0173988 | A1 | 6/2020 | Mallick |
| 2020/0232994 | A1 | 7/2020 | Mitra |
| 2020/0318101 | A1 | 10/2020 | Mallick et al. |

FOREIGN PATENT DOCUMENTS

| | | |
|---|---|---|
| WO | WO-02086081 A2 | 10/2002 |
| WO | WO-2006135527 A2 | 12/2006 |
| WO | WO-2007117444 A2 | 10/2007 |
| WO | WO-2010065531 A1 | 6/2010 |
| WO | WO-2014078855 A1 | 5/2014 |
| WO | WO-2015097077 A2 | 7/2015 |
| WO | WO-2016174525 A1 | 11/2016 |
| WO | WO-2017127762 A1 | 7/2017 |
| WO | WO-2018102759 A1 | 6/2018 |
| WO | WO-2019036055 A2 | 2/2019 |
| WO | WO-2019195633 | 10/2019 |
| WO | WO-2019236749 A2 | 12/2019 |
| WO | WO-2020106889 A1 | 5/2020 |
| WO | WO-2020223368 A1 | 11/2020 |

OTHER PUBLICATIONS

3-Aminopropyl)triethoxysilane. Wikipedia.org. Apr. 5, 2019 (Apr. 5, 2019), entire document esp p. 1 (https://en.wikipedia.org/w/index.php?title=(3-Aminopropyl)triethoxysilane&oldid=891131780).

Arnold et al. "The majority of immunogenic epitopes generate CD44-T cells that are dependent on MHC class II-bound peptide-flanking residues," J Immunol, Jul. 15, 2002 (Jul. 15, 2002), vol. 169, No. 2, pp. 739-749.

Ayoglu, et al., Autoantibody Profiling in Multiple Sclerosis Using Arrays of Human Protein Fragments, Molecular & Cellular Proteomics, (12)9 Sep. 1, 2013 (Sep. 1, 2013), pp. 2657-2672, XP055294116, US ,ISSN: 1535-9476, DOI: 10.1074/mcp.M112.026757.

Blatch, et al. The tetratricopeptide repeat: a structural motif mediating protein-protein interactions. Bioessays Nov. 1999;21 (11):932-939.

Buenrostro, et al. Quantitative analysis of RNA-protein interactions on a massively parallel array for mapping biophysical and evolutionary landscapes. Nat Biotechnol. Jun. 2014; 32(6): 562-568.

Bunka et al. "Production and characterization of RNA aptamers specific for amyloid fibril epitopes," J Biol Chem, Sep. 18, 2007 (Sep. 18, 2007), vol. 282, No. 47, pp. 34500-34509.

Buus, et al. High-resolution mapping of linear antibody epitopes using ultrahigh-density peptide microarrays.Molecular & Cellular Proteomics 11.12 (2012): 1790-1800.

Choung, et al. Determination of B-Cell Epitopes in Patients with Celiac Disease: Peptide Microarrays. PloS one vol. 11(1) e0147777. Jan. 29, 2016, doi:10.1371/journal.pone.0147777.

U.S. Appl. No. 16/760,032, inventors Chee; Mark S et al., filed Apr. 28, 2020.

Co-pending U.S. Appl. No. 16/972,341, inventor Mallick; Parag, filed Dec. 4, 2020.

Co-pending U.S. Appl. No. 17/153,877, inventor Mallick; Parag, filed Jan. 20, 2021.

Co-pending U.S. Appl. No. 17/191,632, inventor Mallick; Parag, filed Mar. 3, 2021.

Domenyuk, et al. Plasma Exosome Profiling of Cancer Patients by a Next Generation Systems Biology Approach. Sci Rep. 2017; 7: 42741.

EP17877076.4 The Extended European Search Report dated Aug. 11, 2020.

EP18846671.8 Extended European Search Report dated Apr. 23, 2021.

Fodor, et al. Light-Directed, Spatially Addressable Parallel Chemical Synthesis. Science , vol. 251, 767-773, 1991.

Ford et al. "Degenerate recognition of T cell epitopes: impact of T cell receptor reserve and stability of peptide:MHC complexes," Mol Immunol, Feb. 1, 2004 (Feb. 1, 2004), vol. 40, No. 14-15, pp. 1019-1025.

Hung, et al. Large-area spatially ordered arrays of gold nanoparticles directed by lithographically confined DNA origami. Nat Nanotechnol. Feb. 2010;5(2):121-6. doi: 10.1038/nnano.2009.450. Epub Dec. 20, 2009.

Hunniger, et al. Just in time-selection: A rapid semiautomated SELEX of DNA aptamers using magnetic separation and BEAMing. Anal Chem. Nov. 4, 2014;86(21):10940-7.

Kang, H. The prevention and handling of the missing data. Korean journal of anesthesiology vol. 64,5 (2013): 402-6. doi:10.4097/kjae.2013.64.5.402.

Laurenson, et al. Development of peptide aptamer microarrays for detection of HPV16oncoproteins in cell extracts, Analytical Biochemistry, Academic Press, Amsterdam,NL, vol. 410, No. 2, Oct. 30, 2010 (Oct. 30, 2010), pp. 161-170, XP028146256,ISSN: 0003-2697,DOI: 10.1016/J.AB.2010.10.038.

Lin et al. Development of a novel peptide microarray for large-scale epitope mapping of food allergens, Journal of Allergy and Clinical Immunology, Elsevier, Amsterdam, NL,vol. 124, No. 2, Aug. 1, 2009 (Aug. 1, 2009), pp. 315-322.e3, XP026390934, ISSN: 0091-6749,DOI: 10.1016/J.JACI.2009.05.024.

Lutz, et al. Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.

McKay, et al. Click Chemistry in Complex Mixtures: Bioorthogonal Bioconjugation. Chem Biol. Sep. 18, 2014; 21(9): 1075-1101.

Meldal, et al. Cu-catalyzed azide-alkyne cycloaddition. Chem Rev. Aug. 2008;108(8):2952-3015. doi: 10.1021/cr0783479.

(56) References Cited

OTHER PUBLICATIONS

Nonobe et al. A tabu search approach to the constraint satisfaction problem as a general problem solver. Eur. J. Oper. Res. 106 (1998): 599-623.
Patronov et al. "Peptide binding prediction for the human class II MHC allele HLA-DP2: a molecular docking approach," BMC Struct Biol, Jul. 14, 2011 (Jul. 14, 2011), vol. 11, No. 32, pp. 1-10.
PCT/US17/64322 International Search Report and Written Opinion dated Apr. 25, 2018.
PCT/US18/00364 International Search Report and Written Opinion dated Mar. 22, 2019.
PCT/US2019/025909 International Search Report and Written Opinion dated Jun. 14, 2019.
PCT/US2019/035654 International Search Report dated Nov. 25, 2019.
PCT/US2019/062482 International Search Report dated Mar. 3, 2020.
PCT/US2020/030501 International Search Report dated Aug. 11, 2020.
Price, et al., On silica peptide microarrays for high-resolution mapping of antibody epitopes and diverse protein-protein interactions, Nature Medicine, vol. 18, No. 9, Aug. 19, 2012, pp. 1434-1440, XP055793803, New York ISSN: 1078-8956, DOI: 10.1038/nm.2913 Retrieved from the Internet:URL:http://w.nature.com/articles/nm.2913.
Reyes et al. "Critical role of HLA-DR11" binding peptides' peripheral flanking residues in fully-protective malaria vaccine development," Biochem Biophys Res Commun, May 23, 2017 (May 23, 2017), vol. 489, No. 3, pp. 339-345.
Richer, et al., Epitope identification from fixed-complexity random-sequence peptide microarrays, Molecular & cellular proteomics, vol. 14, No. 1, Nov. 3, 2014, pp. 136-147.
Rothemund, et al. Folding DNA to create nanoscale shapes and patterns. Nature. Mar. 16, 2006;440(7082):297-302.

Santangelo et al. "Recognition of core and flanking amino acids of MHC class II-bound peptides by the T cell receptor," Eur J Immunol, Sep. 1, 2002 (Sep. 1, 2002), vol. 32, No. 9, pp. 2510-2520.
She, et al. Comprehensive and quantitative mapping of RNA-protein interactions across a transcribed eukaryotic genome. Proc Natl Acad Sci USA. Apr. 4, 2017; 114(14): 3619-3624.
Sjoberg et al. Validation of affinity reagents using antigen microarrays, NewBiotechnology, vol. 29, No. 5, Jun. 1, 2012 pp. 555-563, XP055793929,NLISSN: 1871-6784, DOI: 10.1016/j.nbt.2011.11.009.
Speltz, et al. Design of Protein-Peptide Interaction Modules for Assembling Supramolecular Structures in Vivo and in Vitro. ACS Chem Biol. Sep. 18, 2015;10(9):2108-15. doi: 10.1021/acschembio.5b00415. Epub Jul. 17, 2015.
Stöhr, et al. A 31-residue peptide induces aggregation of tau's microtubule-binding region in cells. Nat Chem. Sep. 2017; 9(9): 874-881. Published online Apr. 3, 2017.doi: 10.1038/nchem.2754.
Tessler, L. Digital Protein Analysis: Technologies for Protein Diagnostics and Proteomics through Single-Molecule Detection (2011). All Theses and Dissertations (ETDs). 346 https://openscholarship.wustl.edu/etd/346.
U.S. Appl. No. 16/659,132 Notice of Allowance dated Jan. 14, 2021.
U.S. Appl. No. 16/659,132 Office Action dated Oct. 8, 2020.
U.S. Appl. No. 16/788,536 Notice of Allowance dated Dec. 9, 2020.
U.S. Appl. No. 16/788,536 Office Action dated Mar. 10, 2020.
U.S. Appl. No. 16/788,536 Office Action dated Sep. 24, 2020.
U.S. Appl. No. 17/191,632 Office Action dated May 12, 2021.
U.S. Appl. No. 16/426,917 Notice of Allowance dated Oct. 1, 2019.
Wilson, et al. Single-Step Selection of Bivalent Aptamers Validated by Comparison with SELEX Using High-Throughput Sequencing. PLoS One. 2014; 9(6): e100572.
Zandian, Arash et al. Whole-Proteome Peptide Microarrays for Profiling Autoantibody Repertoires within Multiple Sclerosis and Narcolepsy. Journal of proteome research 16(3) 2017: 1300-1314. doi:10.1021/acs.jproteome.6b00916.

\* cited by examiner

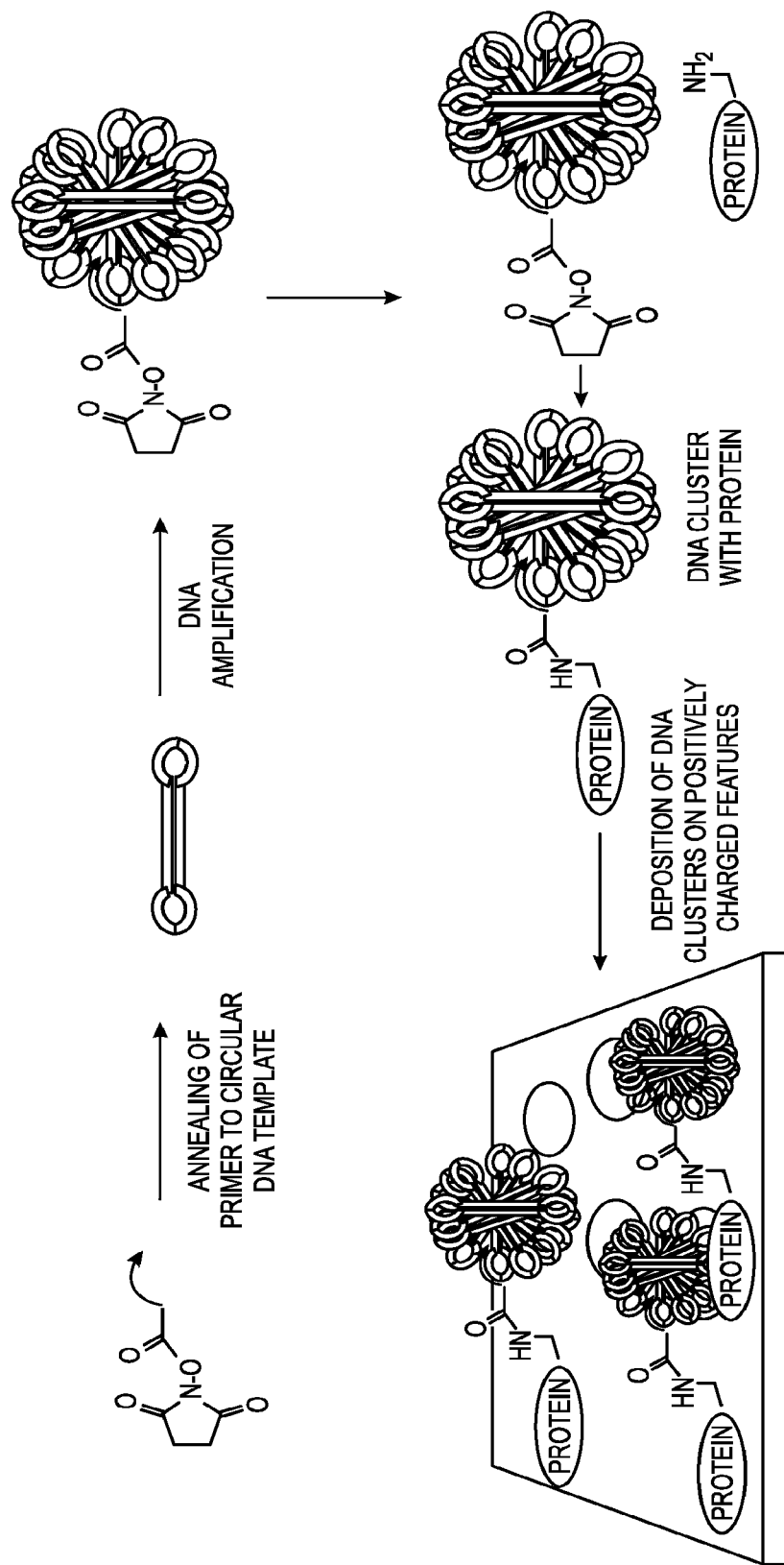

METHODS OF GENERATING NANOARRAYS AND MICROARRAYS

CROSS-REFERENCE

This application is a continuation application of International Patent Application No. PCT/US2019/025909, filed Apr. 4, 2019, which claims the benefit of U.S. Provisional Patent Application No. 62/652,849, filed Apr. 4, 2018, each of which is entirely incorporated herein by reference.

SEQUENCE LISTING

The instant application contains a Sequence Listing which has been submitted electronically in ASCII format and is hereby incorporated by reference in its entirety. Said ASCII copy, created on Dec. 4, 2020, is named 51612-706_301_SL.txt and is 1,458 bytes in size.

BACKGROUND OF THE INVENTION

Microarrays and nanoarrays may be used for assessing biological and chemical entities. It may be beneficial to tailor the design of nanoarrays and microarray to particular assessments.

SUMMARY OF THE INVENTION

The present disclosure provides methods and systems for separating biological and chemical entities.

An aspect of the invention provides a composition comprising a structured nucleic acid particle (SNAP) covalently attached to a protein. In some cases, said SNAP is attached to a solid support. In some cases, said SNAP is covalently attached to a solid support. In some cases, said SNAP is non-covalently attached to a solid support.

An aspect of the invention provides a composition comprising a SNAP covalently attached to a biomolecule. In some cases, said SNAP is attached to a solid support. In some cases, said SNAP is covalently attached to a solid support. In some cases, said SNAP is non-covalently attached to a solid support.

An aspect of the invention provides a composition comprising a solid support attached to a plurality of structured nucleic acid particles (SNAPs), wherein each of said plurality of SNAPs is attached to a biomolecule. In some cases, the plurality of SNAPs are arranged in an array.

An aspect of the invention provides a method of attaching a single protein to an attachment site on a solid support, wherein the attachment site is larger than the protein; the method comprising covalently attaching the protein to a SNAP; wherein the diameter of said SNAP is at least as large as the diameter of the attachment site; and attaching the SNAP to the attachment site. In some cases, each of said plurality of proteins is attached to an attachment site on said solid support; such that each attachment site is attached to a single protein.

An aspect of the invention provides a biomolecule array comprising a plurality of biomolecules attached to a solid support; wherein each biomolecule of the plurality of biomolecules is covalently attached to a linker and the linker is attached to the solid support; and wherein each linker is attached to only one biomolecule of the plurality of biomolecules and each linker has a diameter of at least 50 nm.

An aspect of the invention provides a method of producing an array of spatially separated proteins from a plurality of proteins, the method comprising covalently attaching each protein of the plurality of proteins to an end of a nucleic acid molecule comprising a SNAP, and attaching the SNAPs to a solid support, thereby producing an array of spatially separated proteins.

An aspect of the invention provides a composition comprising a protein, a SNAP and a solid support; wherein the protein is covalently bound to the SNAP, and wherein the protein does not contact the solid support.

An aspect of the invention provides a method of producing an array of spatially separated biological or chemical entities, the method comprising: obtaining a solid support with attachment sites, obtaining a sample comprising a plurality of biological or chemical entities, obtaining seeds, each with a functional group, covalently attaching each biological or chemical entity of the plurality of biological or chemical entities to a single seed via the functional group, growing each attached seed to a SNAP of desired size, attaching the SNAPs to the attachment sites of the array, thereby producing an array of spatially separated biological or chemical entities.

In some cases, a solid support is a glass, silica, plastic, silicon, gold, metal, chromium, titanium, titanium oxide, tin, or tin oxide support. In some cases, a solid support is optically opaque. In some cases, the solid support is optically clear. In some cases, said solid support is modified to have a positive charge. In some cases, said solid support is modified to have a negative charge. In some cases, said solid support is modified to have functional groups which may bind the SNAPs. In some cases, said solid support comprises attachment sites which are modified to be different to surrounding surfaces. In some cases, said solid support comprises an array of attachment sites. In some cases, each attachment site is at least 70 nm from each other attachment site. In some cases, each attachment site is at least 25 nm from each other attachment site. In some cases, the distance between the edges of any two attachment sites is greater than the radius of the SNAP used. In some cases, the distance between the edges of any two attachment sites is greater than the diameter of the SNAP used.

In some cases, the molecules are proteins. In some cases, the seeds are oligonucleotides.

In some cases, the oligonucleotides are modified on the 3' end with a functional group. In some cases, the oligonucleotides are modified on the 5' end with a functional group. In some cases, the functional group is selected from the group consisting of amines, thiols, carboxylic acids, triple bonds, double bonds, epoxides, alkynes, alkenes, cycloalkynes, azides, cyclo-octynes, cycloalkynes, norbornenes, tetrazines, cyclloctanes, epoxides, and hydroxyls. In some cases, the oligonucleotides are modified to comprise a photocleaveable bond. In some cases, the SNAPs are formed by rolling circle amplification. In some cases, the SNAPs are dendrimers. In some cases, the dendrimers are positively charged and the attachment sites on the array are negatively charged. In some cases, the dendrimers are negatively charged and the attachment sites on the array are positively charged. In some cases, the SNAPs have a diameter of approximately 100 nm. In some cases, the SNAPs have a diameter of approximately 300 nm. In some cases the SNAPs have a diameter of between about 10 nm and 500 µm. In some cases, the SNAPs have a diameter of between about 10 nm and 50 µm. In some cases, the SNAPs have a diameter of between about 10 nm and 5 µm. In some cases, the SNAPs have a diameter of between about 100 nm and 500 nm. In some cases, SNAPs adhere to the solid support through an electrostatic interaction.

An aspect of the invention provides a method of achieving spatial separation of molecules, the method comprising: obtaining a plurality of molecules, obtaining seeds, each with a functional group, covalently attaching each of the plurality of molecules to a single seed via the functional group, growing each attached seed to a SNAP of desired size, attaching the SNAPs to a solid support, thereby achieving spatial separation of single molecules.

An aspect of the invention provides an array of single molecules, each single molecule being attached to a SNAP of desired size, the SNAP being attached to the array via an attachment site.

An aspect of the invention provides a kit for producing an array of single molecules, the kit comprising: an array with attachment sites, seeds, each seed having a single attachment site, and reagents to grow the seeds into SNAPs.

An aspect of the invention provides a composition, comprising: a solid support; and a polymer-based molecule attached directly to the solid support, wherein the polymer-based molecule comprises a protein moiety that is oriented substantially opposite of the solid support, and wherein the protein moiety is accessible to affinity reagents.

An aspect of the invention provides a method of isolating biological or chemical entities on an array, the method comprising: generating a plurality of SNAPs; coupling a single biological or chemical entity to each of the plurality of SNAPs; attaching the plurality of SNAPs to an array, wherein the biological or chemical entity is substantially opposite the array, thereby isolating each biological or chemical entity of each of the plurality of SNAPs by a distance that is based on the size of each SNAP of the plurality of SNAPs.

An aspect of the invention provides a method of separating molecules, the method comprising converting each molecule into a larger charged molecule.

In some cases, converting each molecule into a larger charged molecule comprises conjugating the molecule to a biopolymer which can be grown to a desired size.

In some cases, converting each molecule into a larger charged molecule comprises converting each molecule into a molecule 10 times larger.

In some cases, converting each molecule into a larger charged molecule comprises conjugating each molecule to a larger charged molecule.

An aspect of the invention provides a method of producing an array of spatially separated biological or chemical entities, the method comprising: obtaining a solid support with attachment sites, obtaining a sample comprising a plurality of biological or chemical entities, obtaining SNAPs, each with a functional group, covalently attaching each biological or chemical entity of the plurality of biological or chemical entities to a single SNAP, attaching the SNAPs to the attachment sites of the array, thereby producing an array of spatially separated biological or chemical entities.

In some cases, a SNAP is a rolling circle amplification product. In some cases, a SNAP is a plasmid. In some cases, a SNAP is a DNA origami molecule. In some cases, a SNAP is a nucleic acid cluster.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1B illustrates an alternative method of attaching proteins to a substrate, wherein the SNAP is formed initially and then attached to a protein.

FIGS. 18A and 18D illustrate SNAPs detected using fluorescence with a 100×100 micron field of view. FIGS. 18B and 18E illustrate binding of fluorescent streptavidin to biotinylated lysate (FIG. 18B), or control lysate (FIG. 18E). FIGS. 18C and 18F show colocalization of the SNAPs and streptavidin from FIGS. 18A and 18B; and FIGS. 18D and 18E respectively.

FIGS. 19A and 19D illustrate SNAPs detected using fluorescence with a 35×35 micron field of view. FIGS. 19B and 19E illustrate fluorescence from the anti peptide aptamer on the peptide treat array (FIG. 19B), or control array (FIG. 19E). FIGS. 19C and 19F show colocalization of the SNAPs and aptamer from FIGS. 19A and 19B; and FIGS. 19D and 19E respectively.

DETAILED DESCRIPTION OF THE INVENTION

Microarrays and nanoarrays having a plurality of molecules spatially distributed over and stably associated with the surface of a solid support are becoming an increasingly important tool in bioanalysis and related fields. Microarrays of both polypeptides and polynucleotides have been developed and find use in a variety of applications, such as gene sequencing, monitoring gene expression, gene mapping, bacterial identification, drug discovery, and combinatorial chemistry. One area in particular in which microarrays find use is in gene expression analysis.

In some instances it may be desirable to produce a microarray or nanoarray wherein a plurality of biological or chemical entities are spatially distributed over and stably associated with the surface of a solid support such that each individual biological or chemical entity is spatially separated from each other biological or chemical entity.

In some embodiments this disclosure provides methods of producing an array of spatially separated biological or chemical entities, a method may comprise: obtaining a solid support with attachment sites, obtaining a sample comprising biological or chemical entities, obtaining seeds, each with a functional group, covalently attaching each biological or chemical entity to a single seed via the functional group, growing each attached seed to a SNAP (Structured Nucleic Acid Particles) of desired size, attaching the SNAPs to the attachment sites of the array, thereby producing a regular array of biological or chemical entities. In some instances, SNAPs can be any type of DNA based nanoparticle, such as rolling circle amplification based nanoparticles, plasmids, or DNA origami nanoparticles.

Figure 1A:
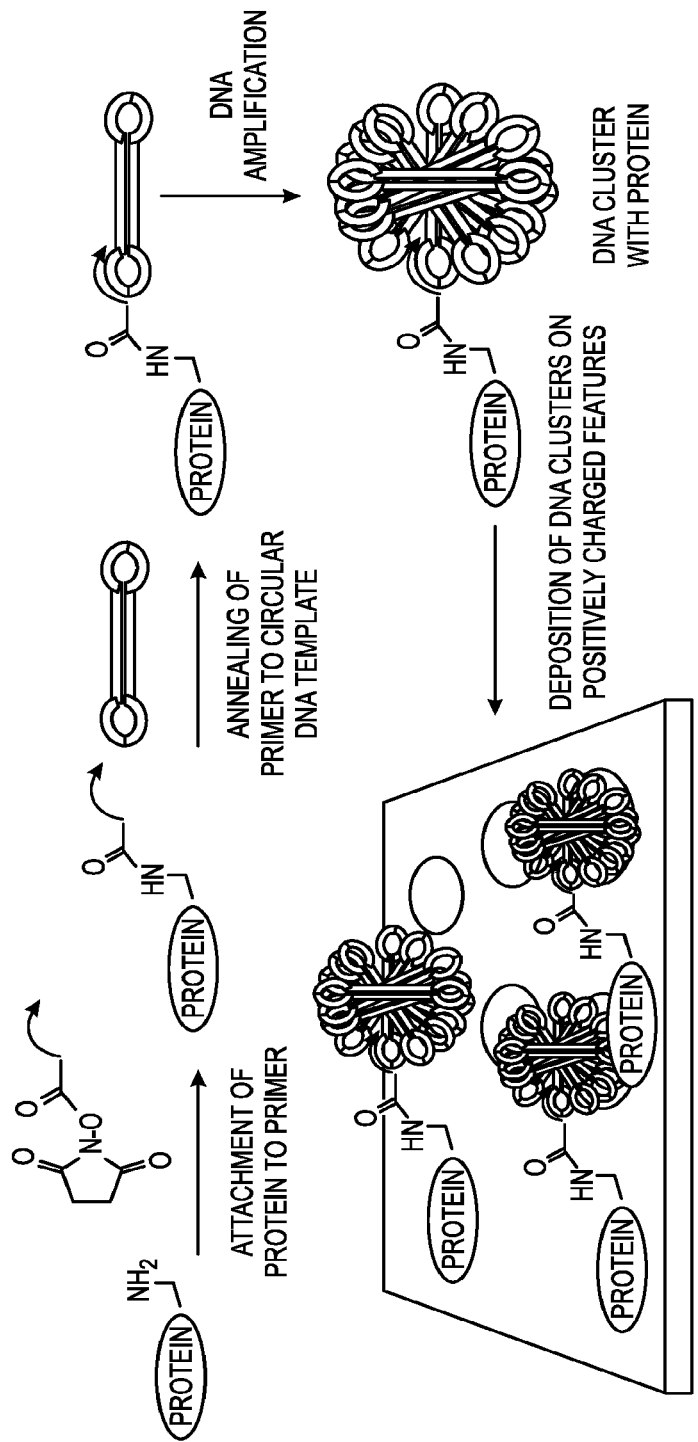
FIG. 1A illustrates an example method of attaching proteins to a substrate via a structured nucleic acid particle (SNAP), wherein a protein is covalently attached to an oligonucleotide primer which is then annealed to a circular DNA template which contains regions of internal complementarity, rolling circle DNA amplification of the primer on the template results in a DNA molecule with regions of internal hybridization resulting in formation of a DNA cluster (an example of a SNAP), since the SNAP is negatively charged it can attach to a positively charged attachment site on a solid support.

Examples of such methods of producing an array of entities such as proteins are provided in FIGS. 1 A-D. FIG. 1A depicts a method which begins with the attachment of a protein to an oligonucleotide primer via a linker. The primer can be then annealed to a circular DNA template, and rolling circle amplification can be performed to produce a SNAP (indicated in this example as a DNA cluster). The SNAP can be then deposited onto a chip. In this example, the negative charge of the DNA backbone can interact with positively charged features of an array, such that the SNAP becomes immobilized on the array.

FIG. 1B depicts a method which begins with a primer having a linker initiating rolling circle amplification with a circular DNA template. The resulting SNAP (indicated in this example as a DNA cluster) thus comprises a linker, which can then be conjugated to a protein. The SNAP can be then deposited onto a chip. In this example, the negative charge of the DNA backbone can interact with positively charged features of an array, such that the SNAP becomes immobilized on the array.

Figure 1C:
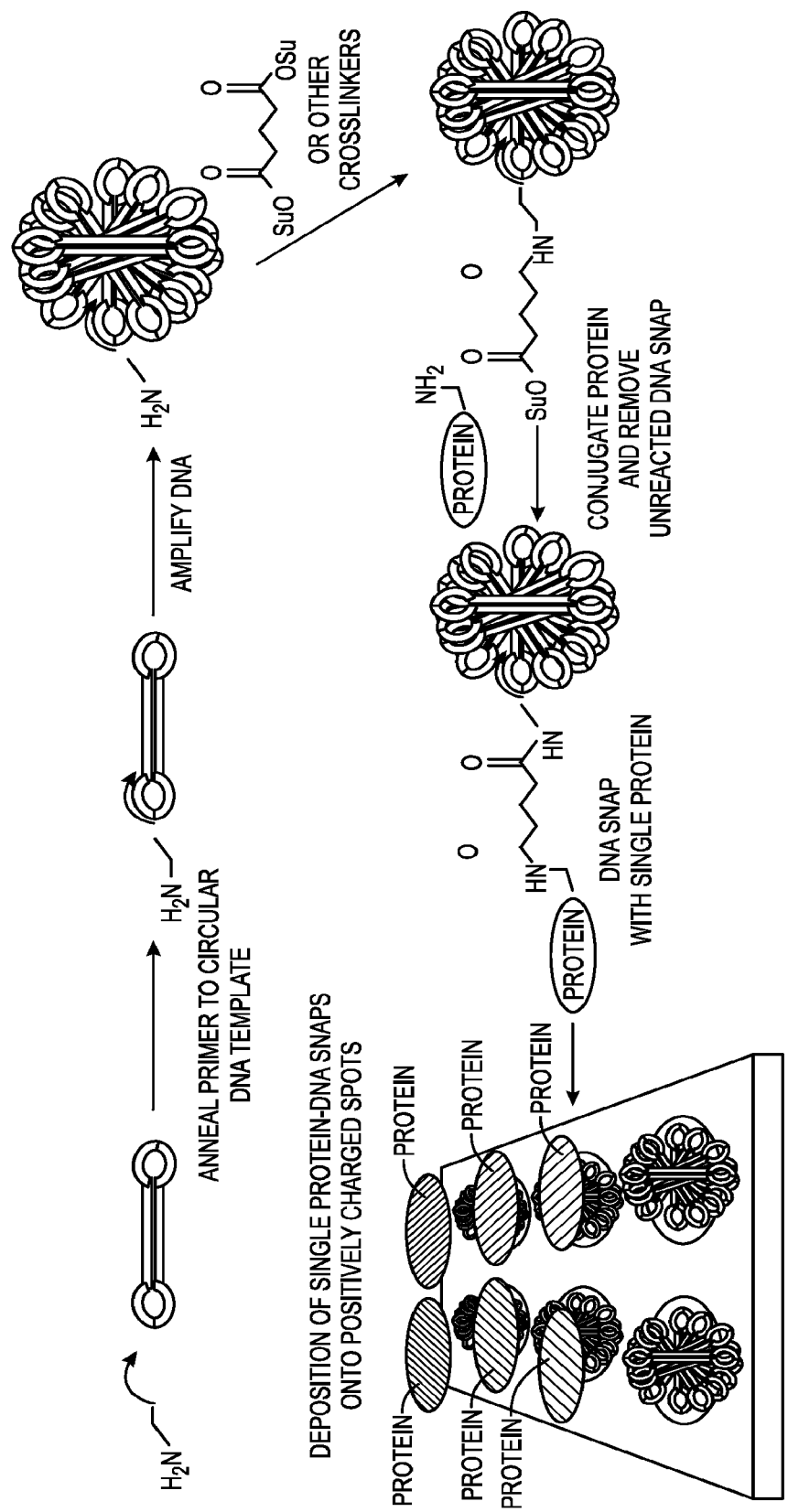
FIG. 1C illustrates an alternative method of attaching proteins to a substrate, wherein the SNAP is formed initially and covalently attached to a crosslinker that is then attached to a protein.

FIG. 1C depicts a method which begins with a primer initiating rolling circle amplification with a circular DNA template. The resulting SNAP (indicated in this example as a DNA cluster) can then be joined with a crosslinker, which can then be conjugated with a protein, to result in a SNAP which is crosslinked to a protein. The SNAP can be then deposited onto a chip. In this example, the negative charge of the DNA backbone can interact with positively charged features of an array, such that the SNAP becomes immobilized on the array.

Figure 1D:
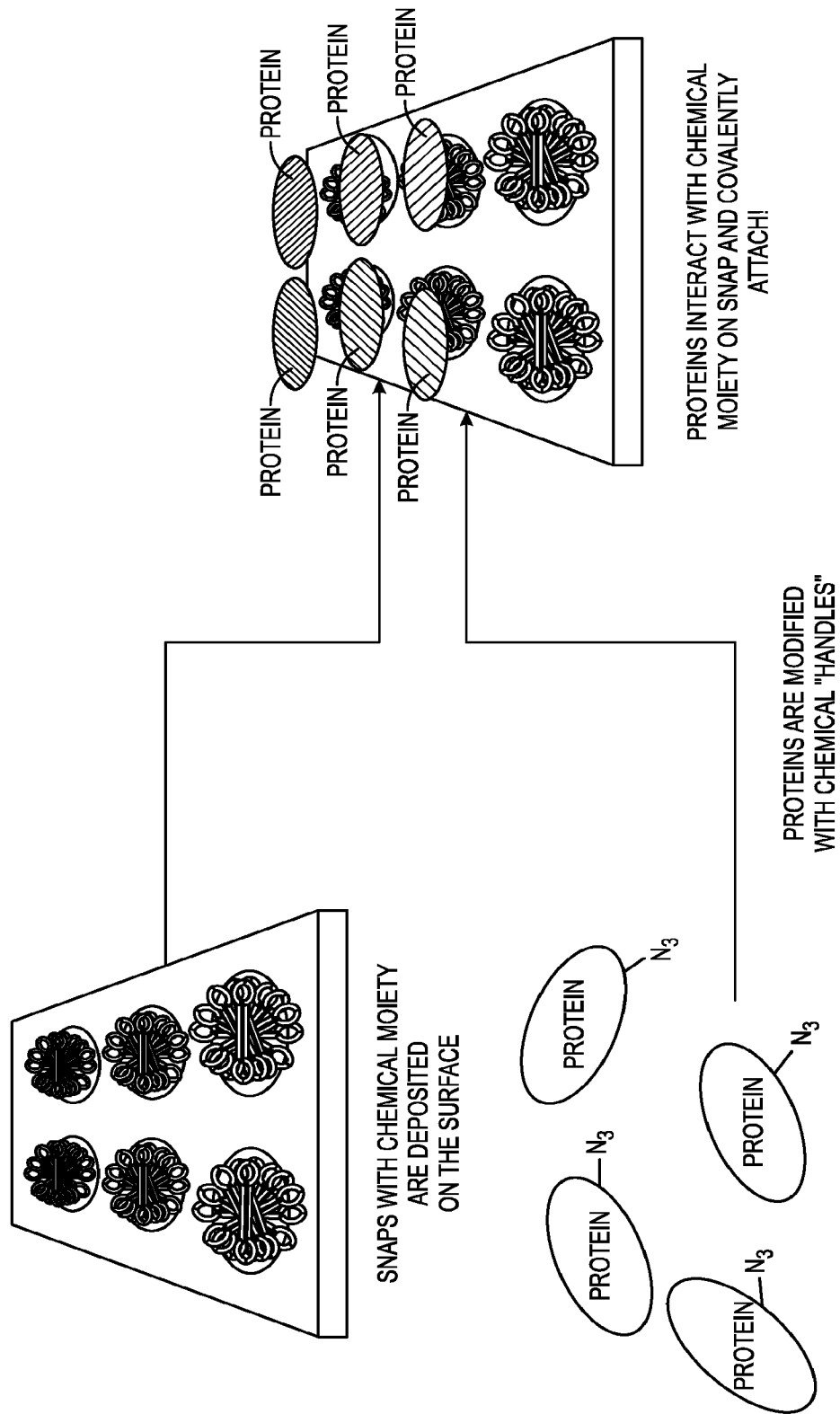
FIG. 1D illustrates an alternative method of attaching proteins to a substrate, wherein SNAPs are deposited onto a surface and proteins with chemical moieties react with the chemical moiety of a SNAP to attach the protein to the SNAP.

FIG. 1D depicts SNAPs which have already been created, for example by rolling circle amplification or other acceptable method. These SNAPs can be then deposited onto a chip. For example, the negative charge of the DNA backbone can interact with positively charged features of an array, such that the SNAP becomes immobilized on the array. Separately, proteins can be modified with chemical handles which can bind a chemical moiety which can be on the SNAPs. The handled proteins can then be applied to the SNAPs, such that they covalently attach to the SNAPs.

In some embodiments this disclosure provides arrays of single molecules and methods and kits for producing arrays of single molecules. In some embodiments this disclosure provides arrays of biological or chemical entities and methods and kits for producing arrays of biological or chemical entities. In some examples, an array of biological or chemical entities may comprise an ordered series of biological or chemical entities arrayed on a solid support. In other examples, an array of biological or chemical entities may comprise an irregular array of biological or chemical entities.

In some examples, biological or chemical entities on an array may be separated by less than 10 nm, about 10 nm, 20 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 μm, 1.2 μm, 1.4 μm, 1.6 μm, 1.8 μm, 2 μm, 2.5 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 40 μm, 50 μm, 75 μm, 100 μm, 200 μm, 300 μm, 400 μm, 500 μm, or more than 500 μm. In some cases, biological or chemical entities on the array may be separated by between about 50 nm and about 1 μm, about 50 nm and about 500 nm, about 100 nm and about 400 nm, about 200 nm and about 300 nm, about 500 nm and about 10 μm, about 50 nm and about 1 μm, or about 300 nm and about 1 μm. In some cases, the spacing of biological or chemical entities on the array may be determined by the presence of attachment sites arrayed on a solid support In some embodiments an array is created on a solid support. The solid support may be any solid surface to which molecules can be covalently or non-covalently attached. Non-limiting examples of solid substrates include slides, surfaces of elements of devices, membranes, flow cells, wells, chambers, and macrofluidic chambers. Solid supports used herein may be flat or curved, or can have other shapes, and can be smooth or textured. In some cases, solid support surfaces may contain microwells. In some cases, substrate surfaces may contain nanowells. In some cases, solid support surfaces may contain one or more microwells in combination with one or more nanowells. In some embodiments, the solid support can be composed of glass, carbohydrates such as dextrans, plastics such as polystyrene or polypropylene, polyacrylamide, latex, silicon, metals such as gold, chromium, titanium, or tin, titanium oxide, tin oxide, or cellulose. In some examples, the solid support may be a slide or a flow cell.

In some embodiments, surfaces of the solid support may be modified to allow or enhance covalent or non-covalent attachment of molecules such as the SNAPs described herein. The solid support and process for molecule attachment are preferably stable for repeated binding, washing, imaging and eluting steps. In some cases, surfaces may be modified to have a positive or negative charge. In some cases, surfaces may be functionalized by modification with specific functional groups, such as maleic or succinic moieties, or derivatized by modification with a chemically reactive group, such as amino, thiol, or acrylate groups, such as by silanization. Suitable silane reagents include aminopropyltrimethoxysilane, aminopropyltriethoxysilane and 4-aminobutyltriethoxysilane. The surfaces may be functionalized with N-Hydroxysuccinimide (NHS) functional groups. Glass surfaces can also be derivatized with other reactive groups, such as acrylate or epoxy, using, e.g., epoxysilane, acrylatesilane or acrylamidesilane.

In some embodiments, the solid support may be modified to reduce non-specific attachment of SNAPs to the solid support. In some embodiments, the solid support may be modified to reduce non-specific attachment of biological entities and/or chemical entities to the solid support. In some embodiments, the solid support may be passivated. In some further embodiments, the surface of the solid support may be passivated. In some embodiments, the passivation layer may include diamond-like carbon, hexa-methyldisilizane, Teflon, fluorocarbon, a polymer such as polyethylene glycol (PEG) and/or Parylene. In some embodiments, a solid support may be passivated by the attachment of Polyethylene glycol (PEG) molecules across the solid support. In some embodiments, a solid support may be passivated using salmon sperm DNA, glycols, albumin, or a combination of the above. In some embodiments, a solid support may be passivated using one or more components selected from the group consisting of salmon sperm DNA, glycols, and albumin. In some embodiments, passivation components may be exposed to a surface. In some embodiments, passivation components may not be covalently bound to a surface. In some embodiments, passivation materials may be not covalently bound to the solid support.

In some embodiments, the solid support may be modified across the entire surface to which molecules are to be attached. In other embodiments, the solid support may contain regions which are modified to allow attachment of molecules and regions which are not modified, or regions which are modified to decrease attachment of molecules and regions which are not modified, or regions which are modified to increase attachment of molecules and regions which are modified to decrease attachment of molecules. In some cases attachment sites may be created in an array, for example an ordered array.

An ordered array of attachment sites may be created by, for example, photolithography, Dip-Pen nanolithography, nanoimprint lithography, nanosphere lithography, cluster lithography, nanopillar arrays, nanowire lithography, scanning probe lithography, thermochemical lithography, thermal scanning probe lithography, local oxidation nanolithography, molecular self-assembly, stencil lithography, or electron-beam lithography. Attachment sites in an ordered array may be located such that each attachment site is less than 20 nanometers (nm), or about 20 nm, about 50 nm, about 75 nm, about 100 nm, about 125 nm, about 150 nm, about 175 nm, about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, about 800 nm, about 825 nm, about 850 nm, about 875 nm, about 900 nm, about 925 nm, about 950 nm, about 975 nm, about 1000 nm, about 1025 nm, about 1050 nm, about 1075 nm, about 1100 nm, about 1125 nm, about 1150 nm, about 1175 nm, about 1200 nm, about 1225 nm, about 1250 nm, about 1275 nm, about 1300 nm, about 1325 nm, about 1350 nm, about 1375 nm, about 1400 nm, about 1425 nm, about 1450 nm, about 1475 nm, about 1500 nm, about 1525 nm, about 1550 nm, about 1575 nm, about 1600 nm, about 1625 nm, about 1650 nm, about 1675 nm, about 1700 nm, about 1725 nm, about 1750 nm, about 1775 nm, about 1800 nm, about 1825 nm, about 1850 nm, about 1875 nm, about 1900 nm, about 1925 nm, about 1950 nm, about 1975 nm, about 2000 nm, or more than 2000 nm from any other attachment site.

In some cases, the spacing of attachment sites on the solid support may be selected depending on the size of the SNAPs to be used. For example the spacing of the attachment sites may be selected such that the distance between the edges of any two attachment sites is greater than the diameter of the SNAP used.

In some cases, the size of the attachment sites on the solid support may be selected depending on the size of the SNAPs to be used. For example the size of the attachment sites may be selected such that the diameter of each attachment sites is less than the diameter of the SNAP used.

In some cases, the attachment sites may be provided in microwells or nanowells.

In some cases, functional groups may be present in a random spacing and may be provided at a concentration such that functional groups are on average at least about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, or more than 100 nm from any other functional group.

The solid support may be indirectly functionalized. For example, the solid support may be PEGylated and a functional group may be applied to all or a subset of the PEG molecules.

In some cases, the efficiency of attachment of the SNAPs to the solid support may be high. In some cases, the efficiency of attachment of the SNAPs to the solid support may be moderate. In some cases, the efficiency of attachment of the SNAPs to the solid support may be low. The efficiency of the attachment of the SNAPs to the solid support may be influenced by many factors, including, but not limited to: sequence of clusters, size of SNAPs relative to size of a corresponding binding patch, the extent to which SNAPs have had their structure modified in such a way so as to influence their binding, age of SNAPs, storage conditions of a buffer or buffers that come into contact with SNAPs, storage conditions of SNAPs, pH or other properties of solvent in which the binding is hoping to be achieved can massively affect, percentages of positive cations, and temperature. In some cases, the reliability of attachment of the SNAPs to the solid support may be high. In some cases, the reliability of attachment of the SNAPs to the solid support may be moderate. In some cases, the reliability of attachment of the SNAPs to the solid support may be low.

In some embodiments the solid support may be optically opaque. In some cases the solid support may be optically clear at one or more wavelengths. In some cases, the solid support may be partially optically clear, or may be optically clear in some regions. For example a solid support may be optically opaque in regions that are not functionalized, and optically clear in regions that are functionalized.

Figure 2:
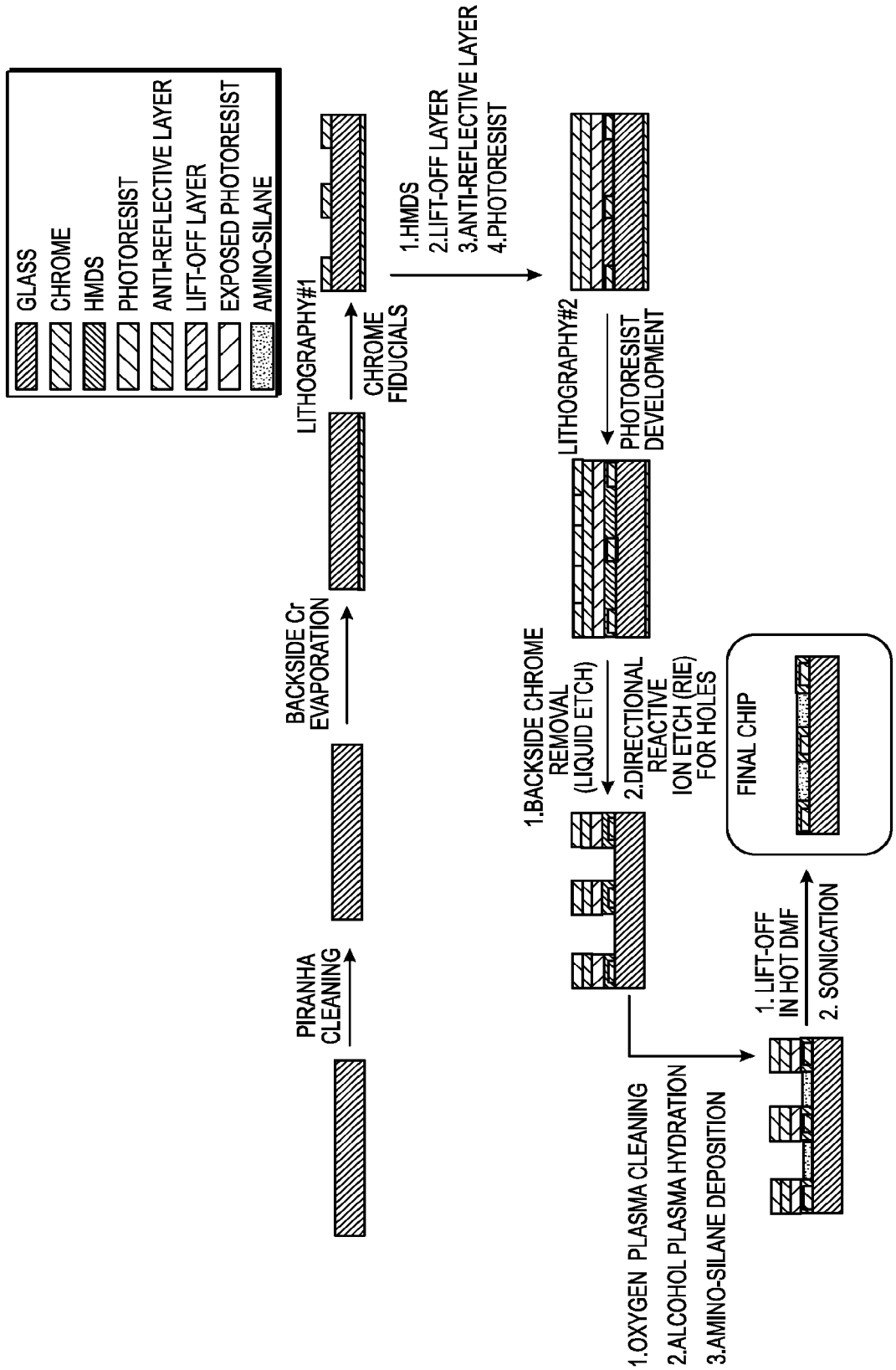
FIG. 2 illustrates a method for producing a solid support with attachment sites arrayed at desired intervals.

FIG. 2 illustrates a method for producing a solid support with attachment sites arrayed at desired intervals. Initially, a substrate is provided. In some embodiments, the substrate may be glass. In particular, in some embodiments, the substrate may be amorphous glass, fused silica, or quartz, among other examples. In some embodiments, the substrate may be silicon. In some embodiments, the thickness of the substrate may be less than 100 microns, 100 microns, 150 microns, 200 microns, 300 microns, 400 microns, 500 microns, 600 microns, 700 microns, 800 microns, 900 microns, 1 millimeter, 2 millimeters, or more than 2 millimeters.

Initially, the substrate is cleaned, such as with a piranha cleaning. In some embodiments, a substrate may be cleaned using a strong acid so as to clean the substrate without etching the substrate. In some embodiments, the substrate may be cleaned using a detergent. Alternatively, the substrate may be cleaned with solvent, sonication or with plasma such as $O_2$ or $N_2$ plasma, or with a combination thereof.

Once the substrate has been cleaned, a chrome layer is deposited on the backside of the substrate. Deposition methods may include, for example, evaporation or sputtering. In some embodiments, a backside chrome evaporation may not be applied when a substrate is opaque. A backside chrome evaporation may have a thickness of one Angstrom, two Angstroms, 10 Angstroms, 10 nanometers, 20 nanometers, 30 nanometers, 40 nanometers, 50 nanometers, 60 nanometers, 70 nanometers, 80 nanometers, 90 nanometers, 100 nanometers, 150 nanometers, 200 nanometers, 250 nanometers, 300 nanometers, 400 nanometers, 500 nanometers, or more than 500 nanometers. Alternatively, other metals can be used for deposition on the backside of the substrate, such as Aluminum, Tungsten, and/or Titanium, among other examples. Alternatively, dielectric mirrors can be used for deposition on the backside of the substrate.

Further, fiducials may be created on the front side of the substrate. Fiducials may be created by adding at least one layer of material and by patterning this at least one layer. In some embodiments, such material can be chrome, and/or such materials may be other metals like tungsten or gold. Alternatively, dielectric mirrors could be used as a material for fiducials. Alternatively, metal oxide could be used for the fiducials as for example $ZrO_2$. The patterning of such materials can be performed in a variety of ways. A first way to pattern the fiducial material is to deposit a blanket layer of the material, then to protect this material in selected areas and remove the material in the areas where it is not protected. This can for example be achieved by coating the front side of the substrate with photosensitive material (e.g. photoresist), patterning this photoresist by exposing it to UV light through a mask and then developing it. The etching of the fiducial material can then be performed by wet etch (for example acid) or dry etch (for example Reactive Ion Etching, RIE). Alternatively, the photoresist may be deposited and patterned first. In some embodiments where the photoresist is deposited and patterned first, areas are defined that are free of such photoresist and then the fiducial material may be deposited on top of the photoresist. The photoresist may then be removed (for example, in a solvent bath with sonication) and the fiducial material may be left on the areas that were initially free of photoresist (e.g., using a lift-off technique). Alternatively, fiducials may be created by removing material from the substrate in selected areas, for example by patterning a layer of photoresist on the front side of the substrate and then by dry etching the substrate in the areas that are not coated with photoresist. In an another alternative, fiducials may be defined by modifying the substrate locally (for example by laser melting and/or fractioning). Fiducials may come in a variety of shapes, lines, and/or orientations. In some embodiments, a pattern of fiducials may be applied to the substrate. In yet another embodiment, the shape of fiducials may vary in order to code information about their location on the surface of the substrate.

Once a pattern of fiducials is created on the front side of the substrate, this front side may be differentially coated to define features where the biological objects of interest (for example, nucleic acid clusters covalently attached to a protein) may be immobilized. In a first embodiment, the surface may be differentially patterned with two silanes, for example HMDS or a PEG-silane in the field and APTES on the immobilization spots. This differential patterning is achieved by, for example, depositing an initial HMDS layer on the surface, followed by a lift-off layer, followed by an optional anti-reflective layer, and followed by a photoresist layer. In some embodiments, an anti-reflective layer may not be provided when an opaque substrate is being used.

Once the photoresist is applied, a second lithography step may be provided. In particular, desired features may be provided. In some embodiments, desired features may have a length of approximately 300 nm. In some embodiments, features may have a length of less than 50 nm, 100 nm, 150 nm, 200 nm, 250 nm, 300 nm, 350 nm, 400 nm, 450 nm, 500 nm, 600 nm, 700 nm, or more than 700 nm. In some further embodiments, one or more layers deposited on the surface to perform this second lithography may not be etched by the developing step of this second lithography (for example, the antireflective coating).

In embodiments where a backside coating is provided, the backside coating may be removed, such as through the use of a wet etch or dry etch etc. Further, a directional reactive ion etch (RIE) may be provided so as to remove layers that haven't been removed by the lithography step (for example the antireflective coating).

Once the holes have been provided, cleaning may be performed. As seen in FIG. 2, an oxygen plasma cleaning and activation step is provided. Once the chip has been cleaned, an amino-silane deposition may be provided. Once the amino-silane deposition is provided, portions of the chip manufacture may be lifted-off, such as using hot DMF.

Further, a sonication step may be performed. The resulting chip may be used in flow cells for assessments of biological assays.

In an alternative embodiment, the surface may be differentially patterned with a silane layer and a metal layer (for example, (3-Aminopropyl)triethoxysilane (APTES) on the immobilization spots and chrome in the field). In another embodiment, the surface may be differentially patterned with a silane layer and a metal oxide layer (for example a PEG-silane layer in the field and a $ZrO_2$ layer on the immobilization spots). In yet another embodiment, the surface may be differentially patterned with a silane layer on the immobilization spots (for example, acyl protein thioesterases (APTS)) and a metal oxide layer (for example a $ZrO_2$) and a PEG-phosphonic acid layer in the field.

The biological or chemical entities of this disclosure may be any biological or chemical entities for which spatial separation is desired. In some embodiments, the biological or chemical entities are proteins. In some cases, the proteins may be proteins from a cell or tissue homogenate, from a biological fluid, or from an environmental sample. In some cases, the biological or chemical entities may be antibodies. In some embodiments the biological or chemical entities are nucleic acids. For example the biological or chemical entities may be DNAs, RNAs, mRNAs, tRNAs, or miRNAs. In some embodiments the biological or chemical entities are carbohydrates. In some embodiments, the biological or chemical entities are complex polymers. In some embodiments the biological or chemical entities are small molecules, for example chemical compounds rather than complex polymers.

The biological or chemical entities of this disclosure may be attached to seeds. These seeds are molecules which can be used as a starting 'seed' to grow a larger polymeric molecule. The seed may be a monomer capable of being grown into a polymer, or may comprise a monomer capable of being grown into a polymer. Generally, the seeds are molecules which can be covalently attached to the molecules. The seeds may have a polarity such that only one functional group of the seed is able to bind to a molecule of the molecules to be separated, while another one or more functional groups of the seed can form the starting point for a polymer.

Examples of monomers which may be present in the seeds include, but are not limited to, oligonucleotides, carbohydrates, proteins, amyloids, fibrils, and tetratricopeptide repeats. In some cases the seeds are small molecules.

The seeds may comprise a monomer and a functional group able to bind to a biological or chemical entity to be separated. Examples of such functional groups may include, but are not limited to, amines, thiols, carboxylic acids, triple bonds, double bonds, epoxides, alkynes, alkenes, cycloalkynes, azides, cyclo-octynes, cycloalkynes, norbornenes, tetrazines, cyclloctanes, epoxides, and hydroxyls. In some cases, the seed may comprise a functional group that is compatible with a click chemistry. In some cases, the seed may also comprise a linker or spacer between the seed and the functional group. In some cases, the linker or spacer may comprise a photo-cleavable bond. In some cases, the seed may comprise an oligonucleotide conjugated to an amine group on the 5' terminal. In some cases, the seed may comprise an oligonucleotide conjugated to a click chemistry component on the 5' terminal.

In some cases, bioconjugation may be used to form a covalent bond between two molecules, at least one of which is a biomolecule. Bioconjugation may be formed but not limited to via chemical conjugation, enzymatic conjugation, photo-conjugation, thermal-conjugation, or a combination thereof (Spicer, C. D., Pashuck, E. T., & Stevens, M. M., Achieving Controlled Biomolecule-Biomaterial Conjugation. Chemical Reviews., 2018, 118, Pgs. 7702-7743, and Greg T. Hermanson, "Bioconjugate Techniques", Academic Press; $3^{rd}$ Edition, 2013, herein incorporated by reference for this disclosure). In some cases, both the seed and the biological (e.g. SNAP) or chemical entity may be functionalized. Functionalizing both partners may improve the efficiency or speed of a conjugation reaction. For example, a sulfhydryl group (—SH) or amine (—$NH_2$) of a chemically active site of a seed, biological, or chemical entity may be functionalized to allow for greater reactivity or efficiency of a conjugation reaction. Any of a variety of sulfhydryl-reactive (or thiol-reactive) or amine conjugation chemistries may be used to couple chemical moieties to sulfhydryl or amine groups. Examples include, but are not limited to, use of haloacetyls, maleimides, aziridines, acryloyls, arylating agents, vinylsulfones, pyridyl disulfides, TNB-thiols and/or other sulfhydryl-reactive/amine-reactive/thiol-reactive agents. Many of these groups conjugate to sulfhydryl groups through either alkylation (e.g., by formation of a thioether or amine bond) or disulfide exchange (e.g., by formation of a disulfide bond). More strategies and detail regarding reactions for bioconjugation are described down below and may be extended to other appropriate biomolecules.

Bioconjugation can be accomplished in part by a chemical reaction of a chemical moiety or linker molecule with a chemically active site on the biomolecule. The chemical conjugation may proceed via an amide formation reaction, reductive amination reaction, N-terminal modification, thiol Michael addition reaction, disulfide formation reaction, copper(I)-catalyzed alkyne-azide cycloaddition (CuAAC) reaction, strain-promoted alkyne-azide cycloaddtion reaction (SPAAC), Strain-promoted alkyne-nitrone cycloaddition (SPANC), invers electron-demand Diels-Alder (IEDDA) reaction, oxime/hydrazone formation reaction, free-radical polymerization reaction, or a combination thereof. Enzyme-mediated conjugation may proceed via transglutaminases, peroxidases, sortase, SpyTag-SpyCatcher, or a combination thereof. Photoconjugated and activation may proceed via photoacrylate cross-linking reaction, photo thiol-ene reaction, photo thiol-yne reaction, or a combination thereof. In some cases, conjugation may proceed via noncovalent interactions, these may be through self-assembling peptides, binding sequences, host-guest chemistry, nucleic acids, or a combination thereof.

In some cases, site-selectivity methods may be employed to modify reaction moieties of biomolecules to increase conjugation efficiency, ease of use, reproducibility. Three common strategies are typically employed for site-selective bioconjugation (i) Modification strategies that can select a single motif among many, rather than targeting a generic reactive handle. This may be determined by surrounding a sequence, local environment, or subtle differences in reactivity. The ability of enzymes to modify a specific amino acid within a protein sequence or a glycan at a single position are particularly prominent. Reactions that display exquisite chemo-selectivity also fall within this category, such as those that target the unique reactivity of the protein N-terminus or the anomeric position of glycans. (ii) The site-specific incorporation of unnatural functionalities, by hijacking native biosynthetic pathways may be utilized. (iii) The installation of unique reactivity via chemical synthesis may be utilized. The complete or partial synthesis of peptides and oligonucleotides is widespread, particularly using solid-phase approaches. These techniques allow access to sequences of up to 100 amino acids or 200 nucleotides, with the ability to install a wide variety of functionalized monomers with precise positional control.

In some cases, chemical conjugation techniques may be applied for creating biomaterial-biomolecule conjugates. Functional groups used for bioconjugation may be native to the biomolecule or may be incorporated synthetically. In the illustrations below, R and R' may be a biomolecule (for example, but not limited to: SNAP, proteins, nucleic acids, carbohydrates, lipids, metabolites, small molecules, monomers, oligomers, polymers) and/or a solid support.

In some cases, reductive amination may be utilized for bioconjugation. Amines can react reversibly with aldehydes to form a transient imine moiety, with accompanying elimination of water. This reaction takes place in rapid equilibrium, with the unconjugated starting materials being strongly favored in aqueous conditions due to the high concentration of water. However, in a second step the unstable imine can be irreversibly reduced to the corresponding amine via treatment with sodium cyanoborohydride. This mild reducing reagent enables the selective reduction of imines even in the presence of unreacted aldehydes. As a result, irreversible conjugation of a biomolecule can gradually occur to a biomaterial of interest. In contrast, stronger reducing agents such as sodium borohydride are also able to reduce aldehydes. This two-step reductive amination process can also be utilized for the modification of ketones. For example, reductive amination has therefore been primarily used for the modification of sodium periodate-treated alginate and chitosan scaffolds. The order of reactivity may also be reversed for the attachment of reducing sugars, by exploiting the terminal aldehyde/ketone generated in the open-chain form. This strategy, for example, may be exploited to mimic the glucosylation and galactosylation patterns of native collagen in ECM, via reductive amination of maltose and lactose respectively.

In some cases, isothiocyanates of a biomolecule or solid support may be utilized for bioconjugation. For example, isothiocyanate of a biomolecule may react with nucleophiles such as amines, sulfhydryls, the phenolate ion of tyrosine side chains or other biomolecules to form a stable bond between two molecules.

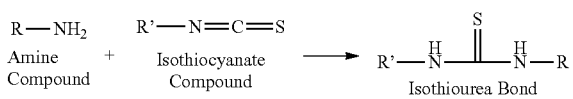

In some cases, an isocyanate of a biomolecule or solid support may be utilized for bioconjugation. For example, isocyanates can react with amine-containing molecules to form stable isourea linkages.

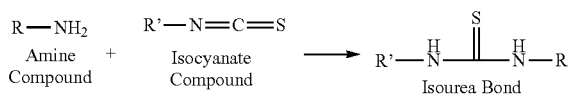

In some cases, an acyl azide of a biomolecule or solid support may be utilized for bioconjugation. For example, acyl azide are activated carboxylate groups that can react with primary amines to form amide bonds.

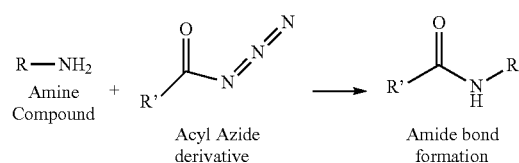

In some cases, an amide of a biomolecule or solid support may be utilized for bioconjugation. For example, the use of reactive N-hydroxysuccinimide (NHS) esters is particularly widespread. While NHS-esters can be preformed, often they are instead generated in situ through the use of N-(3-(dimethylamino)propyl)-N'-ethylcarbodiimide (EDC) coupling chemistry and coupled directly to the species of interest. Although formation of the activated NHS-ester is favored under mildly acidic conditions (pH ~5), subsequent amide coupling is accelerated at higher pHs at which the amine coupling partner is not protonated. One-step modification at an intermediate pH of ~6.5 is possible. Conjugation is typically undertaken by first forming the active NHS-ester at pH 5, before raising the pH to ~8 and adding the amine coupling partner in a two-step procedure. In some cases, water-soluble derivative sulfo-NHS may be utilized as an alternative. In some cases, NHS esters of a biomolecule can react and couple with tyrosine, serine, and threonine —OH groups as opposed to N-terminal α-amines and lysine side-chain ε-amines.

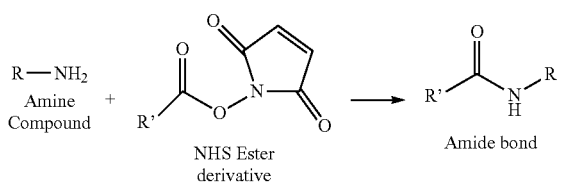

In some cases, a sulfonyl chloride of a biomolecule or solid support may be utilized for bioconjugation. For example, reaction of a sulfonyl chloride compound with a primary amine-containing molecule proceeds with loss of the chlorine atom and formation of a sulfonamide linkage.

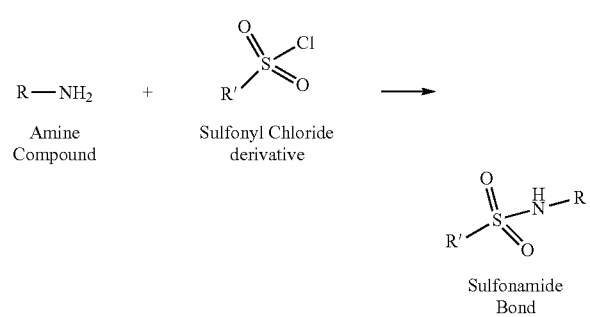

In some cases, a tosylate ester of a biomolecule or solid support may be utilized for bioconjugation. For example, reactive groups comprising tosylate esters can be formed from the reaction of 4-toluenesulfonyl chloride (also called tosyl chloride or TsCl) with a hydroxyl group to yield the sulfonyl ester derivative. The sulfonyl ester may couple with nucleophiles to produce a covalent bond and may result in a secondary amine linkage with primary amines, a thioether linkage with sulf-hydryl groups, or an ether bond with hydroxyls.

In some cases, a carbonyl of a biomolecule or solid support may be utilized for bioconjugation. For example, carbonyl groups such as aldehydes, ketones, and glyoxals can react with amines to form Schiff base intermediates which are in equilibrium with their free forms. In some cases, the addition of sodium borohydride or sodium cyanoborohydride to a reaction medium containing an aldehyde compound and an amine-containing molecule will result in reduction of the Schiff base intermediate and covalent bond formation, creating a secondary amine linkage between the two molecules.

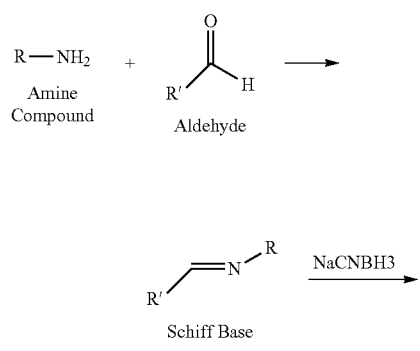

In some cases, an epoxide or oxirane of a biomolecule or solid support may be utilized for bioconjugation. For example, an epoxide or oxirane group of a biomolecule may react with nucleo-philes in a ring-opening process. The reaction can take place with primary amines, sulfhydryls, or hydroxyl groups to create secondary amine, thioether, or ether bonds, respectively.

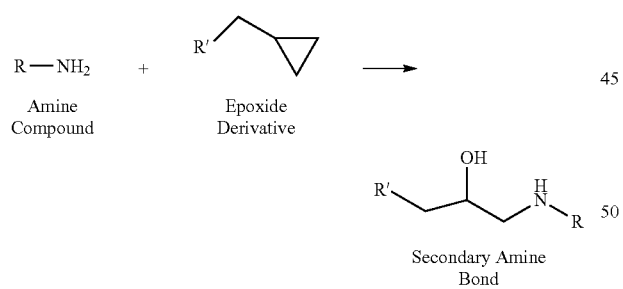

In some cases, a carbonate of a biomolecule or solid support may be utilized for bioconjugation. For example, carbonates may react with nucleophiles to form carbamate linkages, disuccinimidyl carbonate, can be used to activate hydroxyl-containing molecules to form amine-reactive succinimidyl carbonate intermediates. In some cases, this carbonate activation procedure can be used in coupling polyethylene glycol (PEG) to proteins and other amine-containing molecules. In some cases, nucleophiles, such as the primary amino groups of proteins, can react with the succinimidyl carbonate functional groups to give stable carbamate (aliphatic urethane) bonds

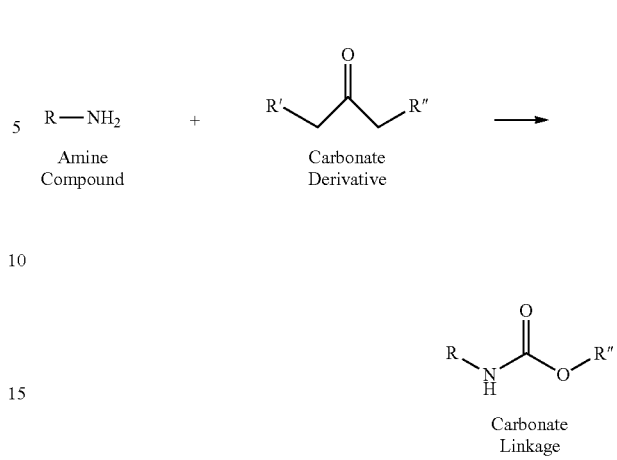

In some cases, an aryl halide of a biomolecule or solid support may be utilized for bioconjugation. For example, aryl halide compounds such as fluorobenzene derivatives can be used to form covalent bonds with amine-containing molecules like proteins. Other nucleophiles such as thiol, imidazolyl, and phenolate groups of amino acid side chains can also react to form stable bonds with a biomolecule or solid support. In some cases, fluorobenzene-type compounds have been used as functional groups in homobifunctional crosslinking agents. For example, their reaction with amines involves nucleophilic displacement of the fluorine atom with the amine derivative, creating a substituted aryl amine bond.

In some cases, an imidoester of a biomolecule or solid support may be utilized for bioconjugation. For example, the α-amines and ε-amines of proteins may be targeted and crosslinked by reacting with homobifunctional imidoesters. In some cases, after conjugating two proteins with a bifunctional imidoester crosslinker, excess imidoester functional groups may be blocked with ethanolamine.

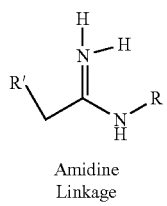

Amidine Linkage

In some cases carbodiimides may be utilized for bioconjugation. Generally, carbodiimides are zero-length cross-linking agents that may be used to mediate the formation of an amide or phos-phoramidate linkage between a carboxylate group and an amine or a phosphate and an amine, respectively. Carbodiimides are zero-length reagents because in forming these bonds no additional chemical structure is introduced between the conjugating molecules. In some cases, N-substituted carbodiimides can react with carboxylic acids to form highly reactive, O-acylisourea derivatives. This active species may then react with a nucleophile such as a primary amine to form an amide bond. In some cases, sulfhydryl groups may attack the active species and form thioester linkages. In some cases, hydrazide-containing compounds can also be coupled to carboxylate groups using a carbodiimide-mediated reaction. Using bifunctional hydrazide reagents, carboxylates may be modified to possess terminal hydra-zide groups able to conjugate with other carbonyl compounds.

In some cases, a biomolecule containing phosphate groups, such as the 5' phosphate of oligonucleotides, may also be conjugated to amine-containing molecules by using a carbodiimide-mediated reaction. For example, the carbodiimide of a biomolecule may activate the phosphate to an intermediate phosphate ester similar to its reaction with carboxylates. In the presence of an amine, the ester reacts to form a stable phosphoramidate bond.

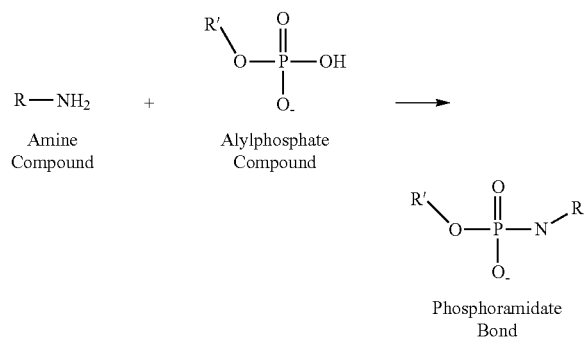

Phosphoramidate Bond

In some cases, an acid anhydride of a biomolecule or solid support may be utilized for bioconjugation. Anhydrides are highly reactive toward nucleophiles and are able to acylate a number of the important functional groups of proteins and other biomolecules. For example, protein functional groups able to react with anhydrides include but not limited to the α-amines at the N-terminals, the ε-amine of lysine side chains, cysteine sulfhydryl groups, the phenolate ion of tyrosine residues, and the imid-azolyl ring of histidines. In some cases, the site of reactivity for anhydrides in protein molecules is modification of any attached carbohydrate chains. In some cases, in addition to amino group modification in a polypeptide chain, glycoproteins may be modified at their polysaccharide hydroxyl groups to form esterified derivatives.

In some cases, a fluorophenyl ester of a biomolecule or solid support may be utilized for bioconjugation. Flurophenyl esters can be another type of carboxylic acid derivative that may react with amines consists of the ester of a fluorophenol compound, which creates a group capable of forming amide bonds with proteins and other molecules. In some cases, fluorophenyl esters may be: a pentafluorophenyl (PFP) ester, a tetrafluorophenyl (TFP) ester, or a sulfo-tetrafluoro-phenyl (STP) ester. In some cases, fluorophenyl esters react with amine-containing molecules at slightly alkaline pH values to give the same amide bond linkages as NHS esters.

In some cases, hydroxymethyl phosphine of a biomolecule or solid support may be utilized for bioconjugation. Phosphine derivatives with hydroxymethyl group substitutions may act as bioconjugation agents for coupling or crosslinking purposes. For example, tris(hydroxymethyl) phosphine (THP) and β-[tris(hydroxymethyl)phos-phino] propionic acid (THPP) are small trifunctional compounds that spontaneously react with nucleophiles, such as amines, to form covalent linkages.

In some cases, the thiol reactivity of a biomolecule or solid support may be utilized for bioconjugation. For example, the thiol group of cysteine is the most nucleophilic functional group found among the 20 proteinogenic amino acids. Through careful control of pH, selective modification over other nucleophilic residues such as lysine can be readily achieved. Another example, thiol modification of oligonucleotides may be used to enable derivatization, though the ease with which alternative reactive handles with enhanced chemical orthogonality can be installed has limited use for biomaterial-conjugation. Further, the conjugate addition of thiols to α,β-unsaturated carbonyls, also known as Michael addition, may be used to form polypeptide conjugates in the fields of tissue engineering, functional materials, and protein modification. In general, reaction rates and conjugation efficiencies are primarily controlled by three factors and may be modified as needed: (i) the $pK_a$ of the thiol; (ii) the electrophilicity of the Michael-acceptor; (iii) the choice of catalyst. Regarding (i): the thiolate anion is the active nucleophile during Michael addition, and the propensity of the thiol to undergo deprotonation may determine thiolate concentration and thus reaction rates. For example, the lower $pK_a$ of aromatic thiols, when compared to their aliphatic counterparts, leads to a higher rate of reaction rate a weak base is used to catalyze the. As a result, local structure can significantly alter conjugation efficiency, particularly for polypeptide substrates. The $pK_a$ and reactivity of cysteine containing peptides can be altered significantly through rational choice of surrounding amino acids, the presence of positively charged amino acids, such as lysine and arginine, acts to lower the thiol $pK_a$ and thus enhance reactivity. Regarding (ii): the Michael-acceptor becomes more electron deficient it becomes more activated toward nucleophilic attack, and thus reaction rates increase. Within the most widely utilized acceptors in the biomaterial field, a trend of reactivity can be generalized as maleimides>vinyl sulfones>acrylates>acrylamides>methacrylates. Regarding (iii) Michael additions can be accelerated by either basic or nucleophilic catalysis (although both act by increasing the concentration of the active thiolate).

In some cases, the unique nucleophilicity of thiols can be exploited for selective reaction with a number of alternative electrophiles, which allow efficient and selective biomolecule attachment to be achieved. For example, one such group are α-halocarbonyls, with iodoacetamide based reagents finding particular utility. Higher thiol selectivity may be achieved using less electrophilic bromo and even chloro derivatives, though reactivity is also drastically reduced. More recently, methylsulfonyl heteroaromatic derivatives have emerged as promising reagents for thiol-specific conjugation. In other cases, alternative thiol-reactive handles, such as disulfide-bridging pyridazinediones, carbonylacrylic reagents, and cyclopropenyl ketones may be utilized for bioconjugation.

In some cases, sulfhydryl of a biomolecule or solid support may be utilized for bioconjugation. In some cases, three forms of activated halogen derivatives can be used to create sulfhydryl-reactive compounds: haloacetyl, benzyl halides, and alkyl halides. In each of these compounds, the halogen group may be easily displaced by an attacking nucleophilic substance to form an alkylated derivative with loss of HX (where X is the halogen and the hydrogen comes from the nucleophile). Haloacetyl compounds and benzyl halides typically are iodine or bromine derivatives, whereas the halo-mustards mainly employ chlorine and bromine forms. Iodoacetyl groups have also been used successfully to couple affinity ligands to chromatography supports.

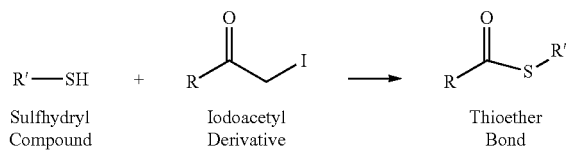

In some cases, a maleimide of a biomolecule or solid support may be utilized for bioconjugation. The double bond of maleimides may undergo an alkylation reaction with sulfhydryl groups to form stable thioether bonds.

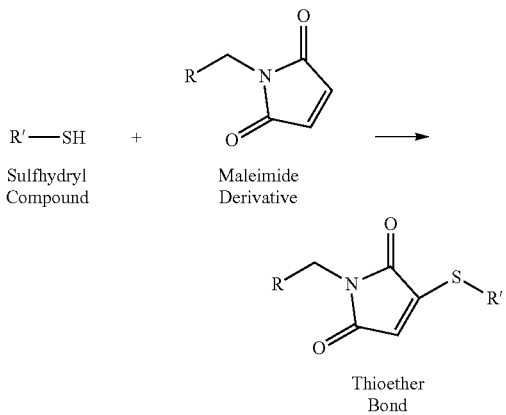

In some cases, an aziridine of a biomolecule or solid support may be utilized for bioconjugation. The highly hindered nature of this heterocyclic ring gives it strong reactivity toward nucleophiles. For example, sulfhydryls will react with aziridine-containing reagents in a ring-opening process, forming thioether bonds. The simplest aziridine compound, ethylenimine, can be used to transform available sulfhydryl groups into amines. In some cases, substituted aziridines may be used to form homobifunctional and trifunctional crosslinking agents.

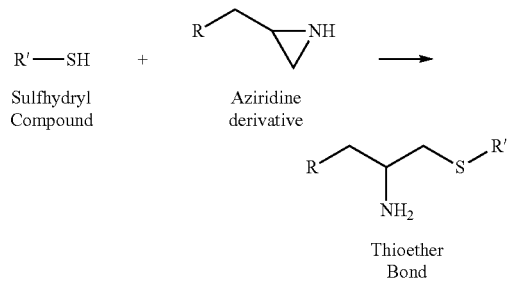

In some cases, thiol-maleimide reactions are particularly useful for undertaking conjugation at low concentrations or when requiring extremely high efficiencies due to the value of the biomolecule substrate. The use of maleimides in bioconjugation is further enhanced by the ease with which they may be introduced into a wide range of scaffold materials, through the modification of amines with the difunctional reagent succinimidyl 4-(N-maleimidomethyl) cyclohexane-1-carboxylate, more commonly referred to by its abbreviation SMCC. For example, this reagent has been widely used to first introduce a maleimide reactive handle on a biomaterial of choice and then to enable the attachment of both peptides and growth factors to produce bioactive scaffolds.

In some cases, an acryloyl of a biomolecule or solid support may be utilized for bioconjugation. The reactive double bonds are capable of undergoing additional reactions with sulfhydryl groups. In some cases, the reaction of an acryloyl compound with a sulfhydryl group occurs with the creation of a stable thioether bond. In some cases, the acryloyl has found use in the design of the sulfhydryl-reactive fluorescent probe, 6-acryloyl-2-dimethylaminonaphthalene.

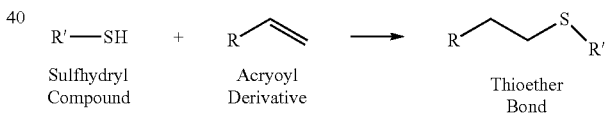

In some cases, an aryl group of a biomolecule or solid support may be utilized for bioconjugation with a sulfhydryl group. Although aryl halides are commonly used to modify amine-containing molecules to form aryl amine derivatives, they also may react quite readily with sulfhydryl groups. For example, fluorobenzene-type compounds have been used as functional groups in homobifunctional crosslinking agents. Their reaction with nucleophiles involves bimolecular nucleophilic substitution, causing the replacement of the fluorine atom with the sulfhydryl derivative and creating a substituted aryl bond. Conjugates formed with sulfhydryl groups are reversible by cleaving with an excess of thiol (such as DTT).

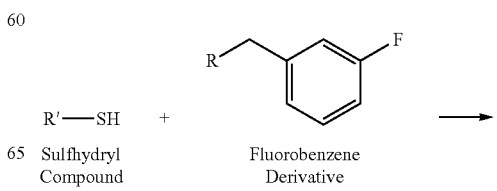

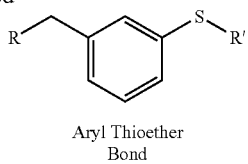

Aryl Thioether
Bond

In some cases, the disulfide group of a biomolecule or solid support may be utilized for bioconjugation. In some cases, compounds containing a disulfide group are able to participate in disulfide exchange reactions with another thiol. The disulfide exchange (also called interchange) process involves attack of the thiol at the disulfide, breaking the —S—S— bond, with subsequent formation of a new mixed disulfide comprising a portion of the original disulfide compound. The reduction of disulfide groups to sulfhydryls in proteins using thiol-containing reductants proceeds through the intermediate formation of a mixed disulfide. In some cases, crosslinking or modification reactions may use disulfide exchange processes to form disulfide linkages with sulfhydryl-containing molecules.

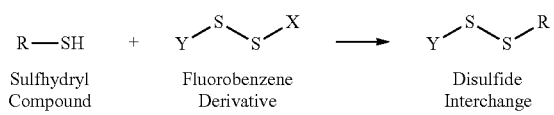

R—SH  +  Fluorobenzene Derivative  →  Disulfide Interchange

Sulfhydryl Compound

In some cases, disulfide bonds may be utilized for bioconjugation. For example, the use of disulfide exchange reactions may be favored for introducing peptides or proteins of interest. The most commonly used reagents in tissue engineering are based upon reactive pyridylthio-disulfides, which undergo rapid thiol-exchange to release the poorly nucleophilic and spectroscopically active 2-mercaptopyridine. Additionally, due to the reversible nature of disulfide bond formation, cleavage can be controlled with temporal precision by the addition of reducing agents such as dithiothreitol (DTT) or glutathione.

In some cases, a pyridyl dithiol functional group may be used in the construction of crosslinkers or modification reagents for bioconjugation. Pyridyl disulfides may be created from available primary amines on molecules through the reaction of 2-iminothiolane in tandem with 4,4'-dipyridyl disulfide. For instance, the simultaneous reaction among a protein or other biomolecule, 2-iminothiolane, and 4,4'-dipyri-dyl disulfide yields a modification containing reactive pyridyl disulfide groups in a single step. A pyridyl disulfide will readily undergo an interchange reaction with a free sulfhydryl to yield a single mixed disulfide product.

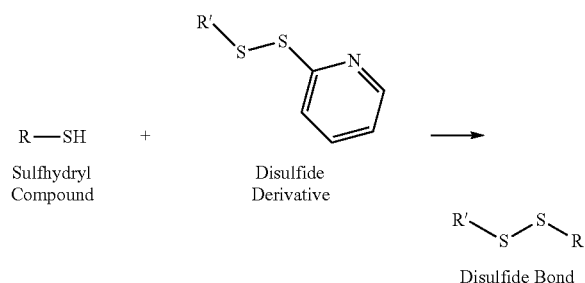

R—SH  +  Disulfide Derivative  →  Disulfide Bond

Sulfhydryl Compound

In some cases, sulfhydryl groups activated with the leaving group 5-thio-2-nitrobenzoic acid can be used to couple free thiols by disulfide interchange similar to pyridyl disulfides, as described herein. The disulfide of Ellman's reagent readily undergoes disulfide exchange with a free sulfhydryl to form a mixed disulfide with concomitant release of one molecule of the chromogenic substance 5-sulfido-2-nitro-ben-zoate, also called 5-thio-2-nitrobenzoic acid (TNB). The TNB-thiol group can again undergo interchange with a sulfhydryl-containing target molecule to yield a disulfide crosslink. Upon coupling with a sulfhydryl compound, the TNB group is released.

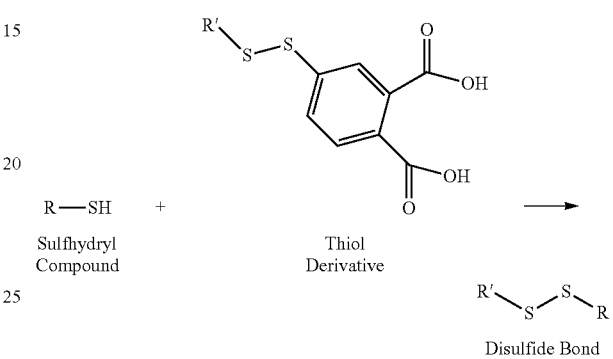

R—SH  +  Thiol Derivative  →

Sulfhydryl Compound

Disulfide Bond

In some cases, disulfide reduction may be performed using thiol-containing compounds such as TCEP, DTT, 2-mercaptoethanol, or 2-mercaptoethylamine.

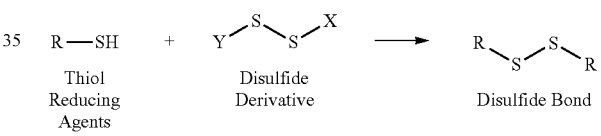

R—SH  +  Disulfide Derivative  →  Disulfide Bond

Thiol Reducing Agents

In some cases, a vinyl sulfone group of a biomolecule or solid support may be utilized for bioconjugation. For example, the Michael addition of thiols to activated vinyl sulfones to form biomolecule-material conjugates have been used to demonstrate that cysteine capped peptides could cross-link vinyl-sulfone functionalized multiarm PEGs to form protease responsive hydrogels, enabling cell invasion during tissue growth. In some cases, in addition to thiols, vinyl sulfone groups can react with amines and hydroxyls under higher pH conditions. The product of the reaction of a thiol with a vinyl sulfone gives a single stereoisomer structure. In addition, crosslinkers and modification reagents containing a vinyl sulfone can be used to activate surfaces or molecules to contain thiol-reactive groups.

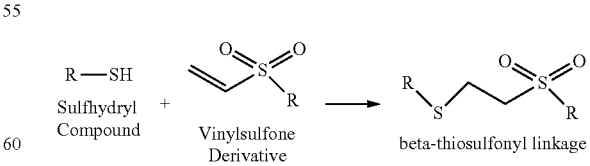

R—SH  +  Vinylsulfone Derivative  →  beta-thiosulfonyl linkage

Sulfhydryl Compound

In some cases, thiol-containing biomolecules can interact with metal ions and metal surfaces to form dative bonds for bioconjugation. In some cases, oxygen- and nitrogen-containing organic or biomolecules may be used to chelate metal ions, such as in various lanthanide chelates, bifunctional metal chelating compounds, and FeBABE. In addition, amino acid side chains and prosthetic groups in proteins frequently form bioinorganic motifs by coordinating a metal ion as part of an active center.

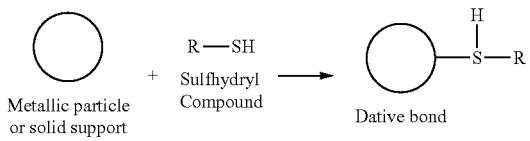

In some cases, thiol organic compounds may be used routinely to coat metallic surfaces or particles to form biocompatible layers or create functional groups for further conjugation of biomolecules. For instance, thiol-containing aliphatic/PEG linkers have been used to form self-assembled monolayers (SAMs) on planar gold surfaces and particles.

In some cases, strong binding of (strept)avidin may be used for the small molecule biotin for bioconjugation. In some cases, (strept)avidin and biotin may be attached to a biomolecule or solid support for bioconjugation. In some cases, modification reagents can add a functional biotin group to proteins, nucleic acids, and other biomolecules. In some cases, depending on the functionality present on the biotinylation compound, specific reactive groups on antibodies or other proteins may be modified to create a (strept)avidin binding site. Amines, carboxylates, sulfhydryls, and carbohydrate groups can be specifically targeted for biotinylation through the appropriate choice of biotin derivative. In some cases, photoreactive biotinylation reagents are used to add nonselectively a biotin group to molecules containing no convenient functional groups for modification. In some cases, biotin-binding proteins can be immobilized onto surfaces, chromatography supports, microparticles, and nanoparticles for use in coupling biotinylated molecules. In

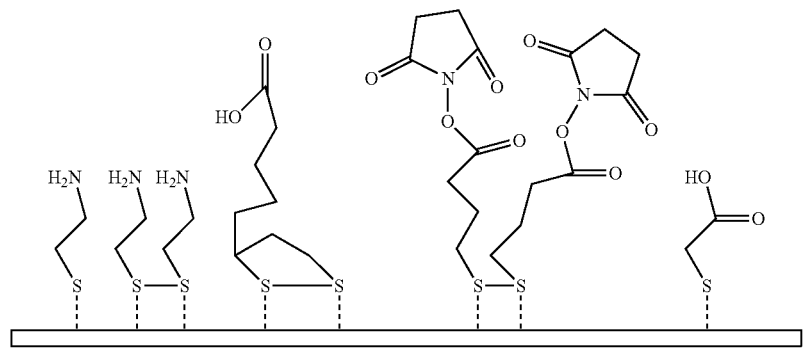

In some cases, a number of alternative coupling systems may be used for biomolecule functionalization. These include the use of O-nitrophenyl esters (which possess reduced stability in aqueous conditions) or 1,1'-carbonyldiimidazole (CDI) to form amine-bridging carbamate linkages rather than amides. Hydrazines can also be used in place of amines during EDC/NHS mediated couplings. Hydrazine-functionalized peptides can be coupled to biomaterials in a single step at pH 5-6. In doing so, a degree of site-selectivity can be achieved over lysine residues present. This approach has been successfully implemented by Madl and co-workers to conjugate reactive groups to alginate hydrogels, enabling indirect functionalization with growth factors and adhesion peptides.

In some cases, N-terminal modification of a biomolecule may be utilized for bioconjugation. For example, 2-pyridinecarboxaldehyde modified acrylamide hydrogels may react specifically with the N-terminus of ECM proteins, forming a cyclic imidazolidinone product with the adjacent amide bond and enabling the orientated display of these key bioinstructive motifs.

In some cases, acrylates, acrylamides, and methacrylates of a biomolecule or solid support may be utilized for bioconjugation. In some cases, thiol-ynes of a biomolecule or solid support may be utilized for bioconjugation.

In some cases, thiol-reactive conjugation such as native chemical ligation (NCL) can be utilized to attach peptides and proteins to biomaterial scaffolds via peptide bond formation. For example, a peptide having a C-terminal thioester reacts with an N-terminal cysteine residue in another peptide to undergo a trans-thioesterification reaction, which results in the formation of an intermediate thioester with the cysteine thiol.

some cases, a series of (strept)avidin biotin interactions can be built upon each other to utilize the multivalent nature of each tetrameric (strept)avidin molecule and enhance the detection capability for the target. In some cases, amine-reactive biotinylation reagents that may contain reactive groups off biotin's valeric acid side chain are able to form covalent bonds with primary amines in proteins and other molecules. In some cases, NHS esters spontaneously react with amines to form amide linkages whereas carboxylate-containing biotin compounds can be coupled to amines via a carbodiimide-mediated reaction using EDC. In some cases, NHS-iminobiotin can be used to label amine-containing molecules with an iminobiotin tag, providing reversible binding potential with avidin or streptavidin. In some cases, Sulfo-NHS-SS-biotin (also known as NHS-SS-biotin) is sulfosuccinimidyl-2-(biotinamido)ethyl-1,3-dithiopropionate, a long-chain cleavable bio-tinylation reagent that can be used to modify amine-containing proteins and other molecules. In some cases, 1-biotinamido-4-[4'-(maleimidomethyl) cyclohexane-carboxamido]butane, a biotinylation reagent containing a maleimide group at the end of an extended spacer arm reacts with sulfhydryl groups in proteins and other molecules to form stable thioether linkages. In some cases, N-[6-(biotinamido)hexyl]-3'-(2'-pyridyldithio)propionamide where the reagent contains a 1,6-diaminohexane spacer group which is attached to biotin's valeric acid side chain, the terminal amino group of the spacer may be further modified via an amide linkage with the acid precursor of SPDP to create a terminal, sulfhydryl-reactive group. The pyridyl disulfide end of biotin-HPDP may react with free thiol groups in proteins and other molecules to form a disulfide bond with loss of pyridine-2-thione.

In some cases, a carboxylate of a biomolecule or solid support may be utilized for bioconjugation. In some cases, diazomethane and other diazoalkyl derivatives may be used to label caroxylate groups. In some cases, N,N'-Carbonyl diimidazole (CDI) may be used to react with carboxylic acids under nonaqueous conditions to form N-acylimidazoles of high reactivity. An active carboxylate can then react with amines to form amide bonds or with hydroxyl groups to form ester linkages. In addition, activation of a styrene/4-vinylbenzoic acid copolymer with CDI may be used to immobilize an enzyme lysozyme or other biomolecule through its available amino groups to the carboxyl groups on to a matrix.

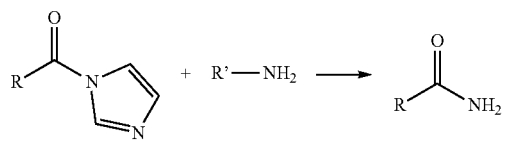

In some cases, carbodiimides function as zero-length crosslinking agents capable of activating a carboxylate group for coupling with an amine-containing compound for bioconjugation or a solid support. In some cases, carbodiimides are used to mediate the formation of amide or phosphoramidate linkages between a carboxylate and an amine or a phosphate and an amine.

In some cases, N,N'-disuccinimidyl carbonate or N-hydroxysuccinimidyl chloroformate may be utilized in bioconjugation. N,N'-Disuccinimidyl carbonate (DSC) consists of a carbonyl group containing, in essence, two NHS esters. The compound is highly reactive toward nucleophiles. In aqueous solutions, DSC will hydrolyze to form two molecules of N-hydroxysuccinimide (NHS) with release of one molecule of $CO_2$. In nonaqueous environments, the reagent can be used to activate a hydroxyl group to a succinimidyl carbonate derivative. DSC-activated hydroxylic compounds can be used to conjugate with amine-containing molecules to form stable crosslinked products.

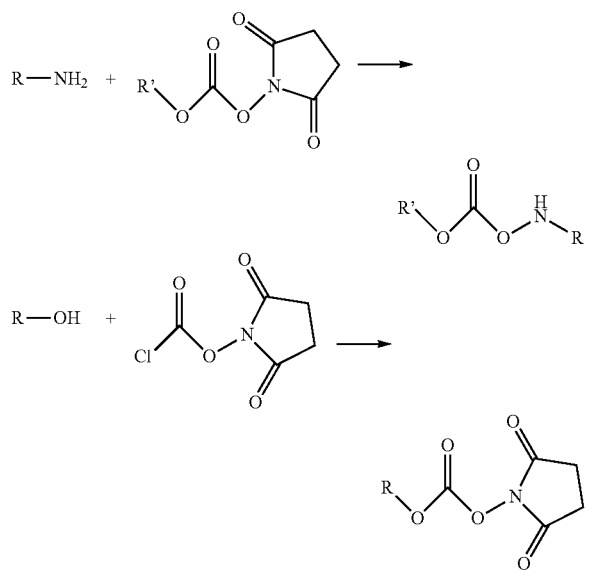

In some cases, sodium periodate can be used to oxidize hydroxyl groups on adjacent carbon atoms, forming reactive aldehyde residues suitable for coupling with amine- or hydrazide-containing molecules for bioconjugation. For example, these reactions can be used to generate crosslinking sites in carbohydrates or glyco-proteins for subsequent conjugation of amine-containing molecules by reductive amination.

In some cases, enzymes may be used to oxidize hydroxyl-containing carbohydrates to create aldehyde groups for bioconjugation. For example, the reaction of galactose oxidase on terminal galactose or N-acetyl-d-galactose residues proceeds to form C-6 aldehyde groups on polysaccharide chains. These groups can then be used for conjugation reactions with amine- or hydrazide-containing molecules.

In some cases, reactive alkyl halogen compounds can be used to specifically modify hydroxyl groups in carbohydrates, polymers, and other biomolecules for bioconjugation.

In some cases, an aldehyde or ketone of a biomolecule or solid support may be used for bioconjugation. For example, derivatives of hydrazine, especially the hydrazide compounds formed from carboxylate groups, can react specifically with aldehyde or ketone functional groups in target biomolecules. To further stabilize the bond between a hydrazide and an aldehyde, the hydrazone may be reacted with sodium cyanoborohydride to reduce the double bond and form a secure covalent linkage.

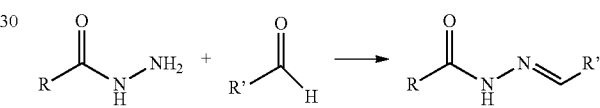

In some cases, an aminooxy group of a biomolecule or solid support may be used for bioconjugation. For example, the chemoselective ligation reaction that occurs between an aldehyde group and an aminooxy group yields an oxime linkage (aldoxime) that has been used in many bioconjugation reactions, as well as in the coupling of ligands to insoluble supports including surfaces. This reaction is also quite efficient with ketones to form an oxime called a ketoxime.

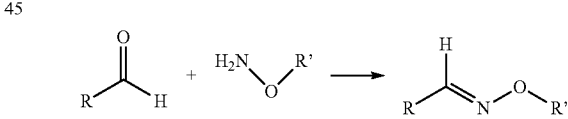

In some cases, cycloaddition reactions may be utilized for bioconjugation. In cycloaddition reactions for bioconjugation, two or more unsaturated molecules are brought together to form a cyclic product with a reduction in the degree of unsaturation, these reaction partners required are typically absent from natural systems, and so the use of cycloadditions for conjugation requires the introduction of unnatural functionality within the biomolecule coupling partner.

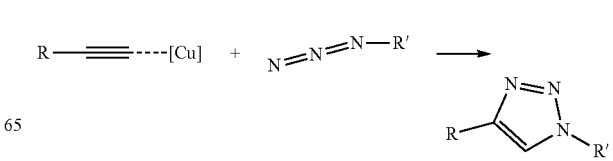

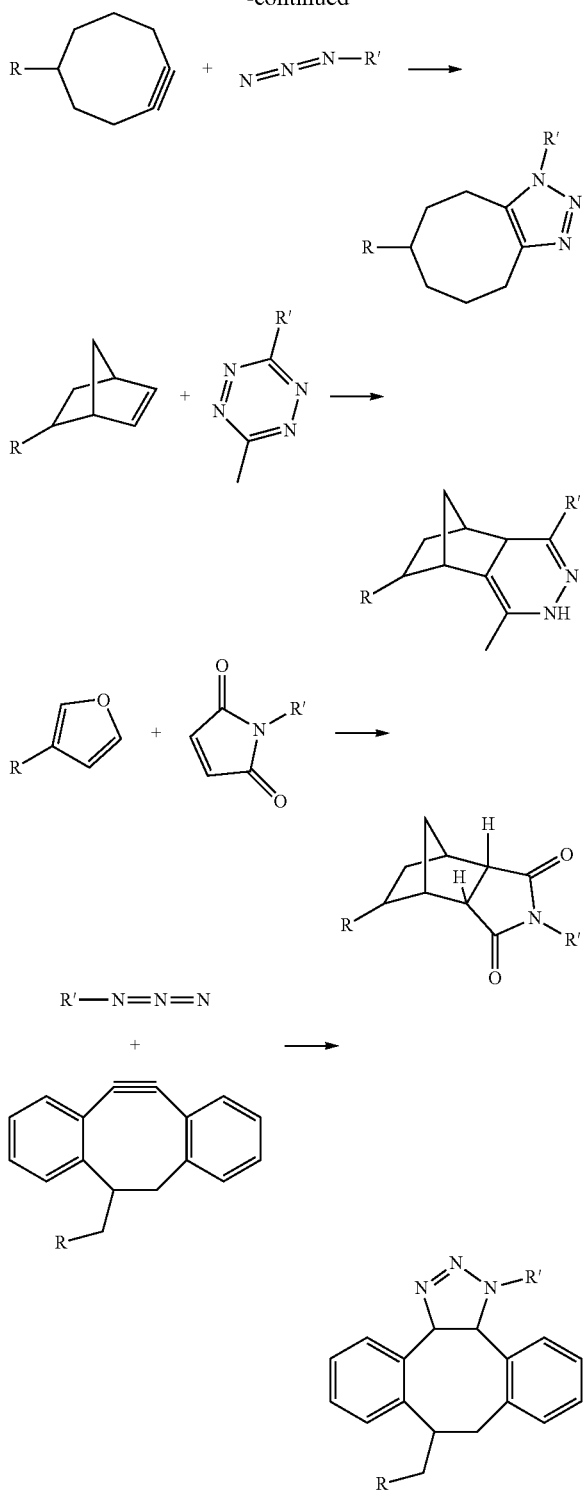

In some cases, Copper-Catalyzed Azide-Alkyne Cycloadditions may be utilized for bioconjugation. In some cases, the (3+2) cycloaddition between an azide and alkyne proceeds spontaneously at high temperatures (>90° C.), producing a mixture of two triazole isomers. In some cases, this reaction proceeds at room temperature, ambient, oxygenated, and/or aqueous environments. In some cases, for example, the formation of peptide-material conjugates by CuAAC, using alkyne-capped peptides to form hydrogels with azide-functionalized PEG. In some cases, CuAAC has been widely used to functionalize scaffolds with alkyne and azide functionalized peptides and carbohydrates, in part due to the ease with which the amino acids azidolysine and homopropargylglycine can be introduced by solid-phase peptide synthesis. In some cases, To achieve biomaterial conjugation via CuAAC, the required copper(I) catalyst can either be added directly, or generated in situ by reduction of an initial copper(II) complex, most commonly using ascorbic acid. The addition of a reducing agent further reduces the sensitivity of the CuAAC ligation to oxygen. Although no additional ligand is necessary for triazole formation, the addition of tertiary amine based ligands may be used.

In some cases, Strain-Promoted Azide-Alkyne Cycloadditions (SPAAC) may be utilized for bioconjugation. In some cases, highly strained cyclooctynes react readily with azides to form triazoles under physiological conditions, without the need for any added catalyst. In some cases, in addition to the use of SPAAC for peptide conjugation, a number of prominent reports have used SPAAC to conjugate protein substrates to cyclooctyne functionalized biomaterials via the introduction of an unnatural azide motif into the protein coupling partner. In some cases, for example, this is achieved by including maleimide functionalization of native cysteines present in bone morphogenetic protein-2 (BMP-2), via enzyme-mediated N-terminal modification of IFN-γ, or via codon reassignment with the unnatural amino acid 4-azidophenylalanine in a number of protein substrates. In some cases, supramolecular host-guest interactions can also be used to promote azide-alkyne cycloaddition. For example, by bringing two reactive partners into close proximity within the cavity of a cucurbit[6]uril host, efficient cycloaddition could be achieved on the surface of proteins, this strategy may be extended to other appropriate biomolecules.

In some cases, inverse-electron demand Diels-Alder reactions (IEDDA) may be utilized for bioconjugation. For example, the inverse-electron demand Diels-Alder (IEDDA) reaction between 1,2,4,5-tetrazines and strained alkenes or alkynes may be employed. A wide range of suitable derivatives for undertaking biomolecule conjugation have been reported, for example, a series of increasingly strained (and thus reactive) trans-cyclooctenes may be utilized. In some cases, functionalized norbornene derivatives may be utilized for undertaking IEDDA reactions. In some cases, triazines may be utilized. In some cases, spirohexene may be utilized. These strategies may be extended to other appropriate biomolecules. In some cases, hetero-Diels-Alder cycloaddition of maleimides and furans may be utilized for bioconjugation. For example, the coupling of furan-functionalized RGDS peptides to maleimide-functionalized PEG-hydrogels may be utilized, this strategy may be extended to other appropriate biomolecules. In some cases, furan-functionalized hyaluronic acid hydrogels can be cross-linked with a dimaleimide-functionalized peptide via Diels-Alder cycloaddition. MMP-cleavable peptides enable the migration of seeded cancer through the gel.

In some cases, oxime and hydrazone formation may be utilized for bioconjugation. In some cases, the stable attachment of peptides and DNA to biomaterials via hydrazone formation can be achieved via difunctional cross-linking, this strategy may be extended to other appropriate biomolecules. In some cases, the attachment of ketone or aldehyde modified green fluorescent protein (GFP) or metallothionein to hydroxylamine-functionalized synthetic polymers may be extended to other appropriate biomolecules. For example, protein cross-linked hydrogels were produced through oxime modification at both the protein N- and C-termini.

In some cases, the Diels-Alder reaction consists of the covalent coupling of a diene with an alkene to form a six-membered ring complex for bioconjugation.

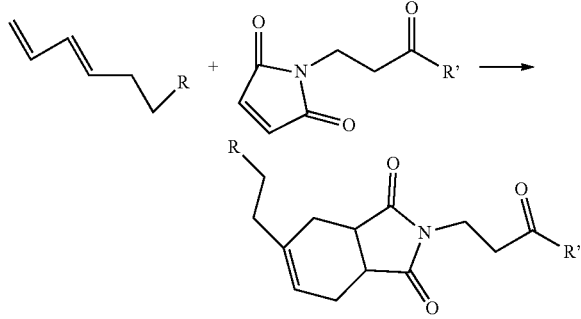

In some cases, transition metal complexes may be utilized for bioconjugation. The nature of late transition metals may make a transition metal complex well suited to the manipulation of unsaturated and polarizable functional groups (olefins, alkynes, aryl iodides, arylboronic acids, etc.). For example, Pd(0)-functionalized microspheres may mediate allyl carbamate deprotections and Suzuki-Miyaura crosscouping in the cytoplasm. In other examples, a ruthenium catalyst may be used to mediate allyl carbamate deprotection of a caged fluorophore inside living cells. In some cases, applications of palladium-based applications in cell culture include copper-free Sonagashira coupling, extracellular Suzuki coupling on the surface of E. coli cells, and conjugation of thiol groups with allyl selenosulfate salts. In some cases, olefin metathesis may be utilized for bioconjugation. For example, with ruthenium complexes, S-allylcysteine can be easily introduced into proteins by a variety of methods, including conjugate addition of allyl thiol to dehydroalanine, direct allylation of cysteine, desulfurization of allyl disulfide, or metabolic incorporation as a methionine surrogate in methionine auxotrophic E. coli.

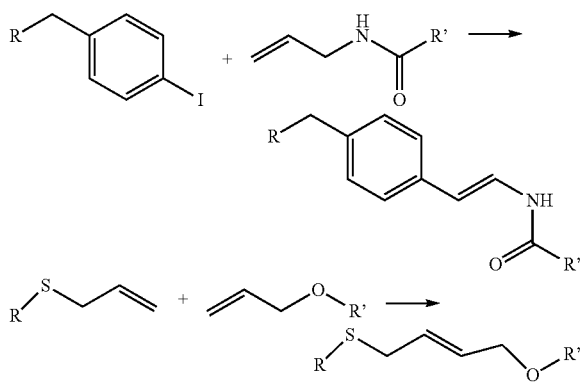

In some cases, complex formation with boronic acid derivatives may be used for bioconjugation. For example, boronic acid derivatives are able to form ring structures with other molecules having neighboring functional groups consisting of 1,2- or 1,3-diols, 1,2- or 1,3-hydroxy acids, 1,2- or 1,3-hydroxylamines, 1-2- or 1,3-hydroxyamides, 1,2- or 1,3-hydroxyoximes, as well as various sugars or biomolecules containing these species.

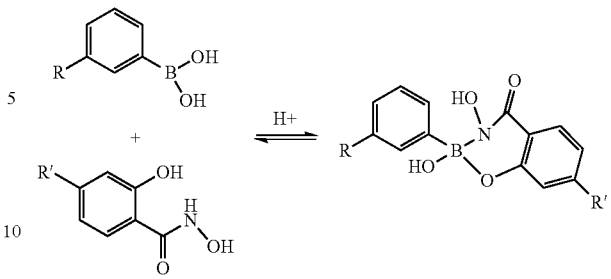

In some cases, enzyme-mediated conjugation may be utilized for bioconjugation. For example, the transglutaminase enzyme family catalyzes the formation of isopeptide bonds between the primary amine of lysine side chains and the amide bonds of a complementary glutamine residue, this strategy may be extended to other appropriate biomolecules. In other cases, peroxidase-mediated conjugation may be utilized for bioconjugation. For example, horse radish peroxidase (HRP) may be utilized to oxidize a wide range of organic substrates such as phenol group of tyrosie to generate a highly reactive radical or quinone intermediate that undergoes spontaneous dimerization, resulting in the formation of an ortho carbon-carbon bond between two tyrosine residues, this strategy may be extended to other appropriate biomolecules. In some cases short peptide tags may be utilized for bioconjugation. These peptide tags may be as short as 5 amino acids long and may be appended to a peptide or protein substrate which allows for their subsequent modification.

In some cases, polymerization of low molecular weight monomers may be utilized for bioconjugation. Polymerization may be classified as proceeding via one of two mechanisms, either chain-growth or step-growth. During chain-growth polymerization, monomers are added at the "active" end of a growing polymer chain, resulting in the formation of high molecular weight materials even at low conversions. During step-growth polymerizations short oligomer chains couple to form polymeric species, requiring high conversions in order to reach high molecular weights. Both techniques can be used to form biomolecule-polymer conjugates. The polymerization of acrylate and methacrylate monomers has proven particularly fruitful. For example, acrylate and methacrylate modified peptides and glycans can be readily polymerized. Similarly, availability of the synthetic oligonucleotide phosphoramidite building block "Acrydite", free-radical polymerization remains one of the most common methods through which to form DNA and RNA functionalized biomaterials. By undertaking polymerization in the presence of a comonomer, the density of biomolecule presentation can be easily tuned, allowing potential difficulties from steric hindrance to be overcome. Initiation of polymerization can be triggered by a number of means, including heat, UV and visible light, redox reactions, and electrochemistry. Acrylate modified proteins can also undergo polymerization to produce functional materials, while retaining biological activity. In some cases living radical polymerizations (LRPs) may be utilized for bioconjugation. For example, the most commonly used LRPs for the formation of bioconjugates include atom-transfer radical polymerization (ATRP), reversible addition-fragmentation chain transfer (RAFT) polymerization, and nitroxide-mediated polymerization (NMP).

In some cases, photoconjugation may be utilized for bioconjugation. In some cases polymerization is initiated by the production of a radical species, which then propagates through bond formation to create an active polymer chain. The initiation step can be induced via a number of stimuli, with thermal decomposition, redox activation, and electrochemical ionization of an initiating species being among the most common. Alternatively, many initiators can be activated via light-induced photolytic bond breakage (type I) or photoactivated abstraction of protons from a co-initiator (type II). Photoinitiation offers the benefits of being applicable across a wide temperature range, using narrow and tunable activation wavelengths dependent on the initiator used, rapidly generating radicals, and the ability to control polymerization by removing the light source. Importantly, the tolerance of polymerizations to oxygen is greatly enhanced, enabling polymerization in the presence of cells and tissues. The incorporation of acrylate-functionalized peptides and proteins during photopolymerization may be used as a method for producing biomaterial conjugates. Alternatively, the photoinitiated attachment of polypeptides to pendant vinyl groups on preformed materials has also been widely reported and more recently used for 3D patterning via two-photon excitation. A wide range of photoinitiators may be used in photoconjugation conjugations. For example but not limited to, Eosin Y, 2,2-dimethoxy-2-phenyl-acetophenone, Igracure D2959, lithium phenyl-2,4,6-trimethylbenzoylphosphinate, and riboflavin may be used as photoinitiators. Photoinitiators generally absorb light to initiate the photoreaction processes. In some cases, photoconjugation may utilize a photo thiol-ene reaction. Thiols can also react with alkenes via a free-radical mechanism. A thiol radical first reacts with an alkene to generate a carbon-centered radical, which can then abstract a proton from another thiol and thus propagate the reaction. Photo thiol-ene reactions may be accelerated by electron-rich alkenes, which generate unstable carbon-radical intermediates able to rapidly abstract thiol-hydrogens. Exceptions to this rule are norbornene derivatives, in which reactivity is driven instead by the release of ring strain upon thiol addition. This leads to a general trend in reactivity of norbornene>vinyl ether>propenyl>allyl ether>acrylate>maleimide. Norbornenes and allyloxycarbonyls (alloc groups) have been particularly widely used for peptide/protein-biomaterial functionalization, due to the almost negligible contribution of chain transfer and their ease of introduction during peptide synthesis, respectively. For example, an alloc group, typically used as an orthogonal lysine protecting group during solid-phase peptide synthesis, is an efficient photo thiol-ene reactive handle. In other examples, norbornene photo thiol-ene reactions may be used for the tethering and spatial patterning of bioactive peptides and growth factor proteins. In addition to the most commonly used alloc and norbornene reactive groups, other alkenes have also been used for biomaterial functionalization. For example, codon reassignment has been used to site-specifically incorporate allyl-cysteine residues into proteins, which can subsequently undergo conjugation through the use of photo thiol-ene reactions. Alternatively, acrylates can undergo mixed-mode photopolymerizations in the presence of cysteine capped peptides, while allyl disulfide structures have recently been shown to undergo reversible and controlled exchange of conjugated thiols.

In some cases, aryl azide or halogenate aryl azides of a biomolecule or solid support may be utilized for bioconjugation.

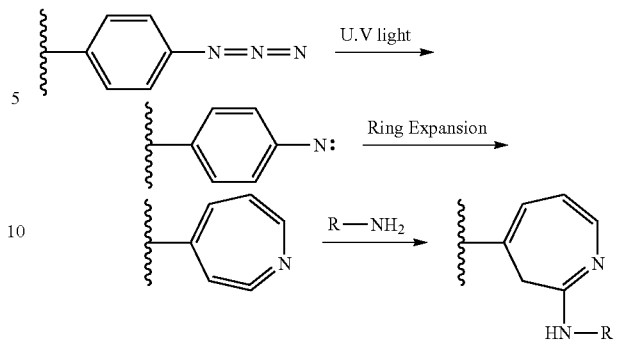

In some cases, photoreactive group benzophenone may be utilized for bioconjugation.

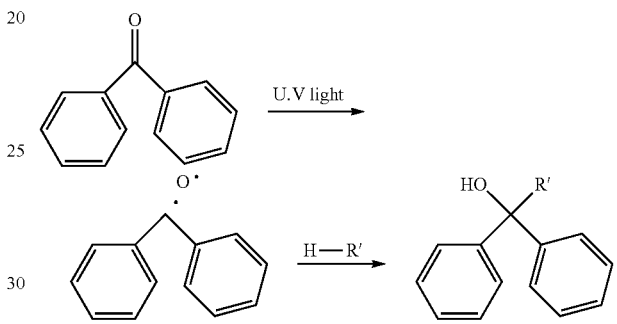

In some cases, photoreactive group anthraquinone may be utilized for bioconjugation.

In some cases, photo thiol-yne reactions may be utilized for bioconjugation. Most examples of photo thiol-yne reactions have exploited simple propargyl-ether or -amine reactive handles.

In some cases, photocaging and activation of reactive functionalities may be utilized for bioconjugation. Generally, a transient reactive species is formed whether it be an acrylate or thiol derived radical. In some cases, photocaging may be used to mask or protect a functional group until it is desirable for it to be exposed. In some cases, the most widely utilized cages are based around o-nitrobenzyl and coumarin chromophores. For example, nitrobenzyl-capped cysteine residues may be decaged by irradiation with 325 nm UV light, the released thiol may then react with maleimide-functionalized peptides via Michael addition, to generate a patterned hydrogel able to guide cell migration. In some cases, 6-bromo-hydroxycoumarins may be used for thiol-caging. In some cases, photoaffinity probes may be utilized for bioconjugation where a highly reactive intermediate upon irradiation, which then reacts rapidly with the nearest accessible functional group with high spatial precision. In some cases, the most commonly used are phenylazides, benzophenones, and phenyl-diazirines. In some cases, photocaged cycloadditions may be used. For example, the UV irradiation of tetrazoles has been shown to generate a reactive nitrile-imine intermediate which can undergo rapid cycloaddition with electron-deficient alkenes such as acrylates or acrylamides. In some cases, the nitrile-imine side-reactivity with thiols may be utilized for site-specifically conjugate cysteine containing proteins to tetrazole functionalized surfaces.

In some cases, noncovalent interactions may be utilized for bioconjugation. In some cases, noncovalent binding plays a vital role in cells, controlling biomolecular interfaces and influencing protein-protein interactions, DNA-DNA complexation, DNA-protein interfaces, protein localization, and more. In some cases, noncovalent sequences which display a binding affinity for the biomolecule of interest, allow for postfabrication modification or for native biomolecules to be simply sequestered from the surroundings within biological samples. The most commonly used binding sequences are short peptides between 7 and 20 amino acids in length, derived from a variety of sources, including known protein binding domains present in vivo or determined through techniques such as phage display. In some cases, short oligonucleotides known as aptamers can also be used to bind a variety of protein substrates, including the cytokines vascular endothelial growth factor (VEGF) and platelet derived growth factor (PDGF), as well as cell surface proteins such as epidermal growth factor receptor (EGFR). In some cases, binding sequences can also be introduced into a biomaterial with affinity for native biopolymers, such as heparin. In some cases, by first inducing biopolymer binding, the adsorption of an added or endogenous growth factor or signaling protein to a biomaterial scaffold can then be controlled. In some cases, binding affinity at the amino acid level can also be exploited to enable peptide and protein conjugation to certain biomaterial substrates. For example, the binding of unnatural catechol-based amino acids can be used to induce binding to metal oxide containing bioglasses and metallic implants, enabling the bioactivity of these important technologies to be enhanced.

In some cases, self-assembling peptides may be utilized for bioconjugation. For example, native peptides and proteins adopt a series of secondary structures, including β-sheets and α-helices, which can both stabilize individual sequences and control interprotein aggregation. In some cases, self-assembling peptides have been used extensively to assemble hydrogels and fibrous materials. In many of these structures, biological epitopes or functional groups can be appended to some or all of the peptide building blocks during peptide synthesis, to add the desired bioactivity into the system. Peptide-ligands ranging from simple adhesion motifs, to laminin derived epitopes, and growth factor mimetics have all been displayed on the surface of self-assembled fibrils. Alternatively, glycopeptides can be assembled in order to recruit extracellular signaling proteins and growth factors, mimic glycosylation patterns within hyaluronic acid, or investigate optimal sulfonation ratios in glycosaminoglycan scaffolds. In some cases, self-assembling domains can also be added to full-length proteins, leading to the incorporation of pendant functionality during hydrogel formation. In some cases, the propensity of peptides to form secondary structures has also been exploited within nonself-assembling scaffolds. This may be achieved by mixing a self-assembling peptide into a covalent hydrogel, composed of either a noninteracting polymer such as interpenetrating networks of PEG or systems where additional charge interactions further stabilize the final construct, for example between positively charged peptides and negatively charged alginate gels. As an alternative, pendant helical groups can be attached to a covalent material and used to drive the noncovalent attachment of bioactive groups such as growth factors via self-assembly into coiled-coil triple helices.

In some cases, host-guest chemistry may be utilized for bioconjugation. For example, the adhesive properties of a β-cyclodextrin modified alginate scaffold could be controlled in situ through the addition of a guest naphthyl-functionalized RGDS peptide and by subsequently introducing a non-cell adhesive adamantane-RGES peptide with a higher host binding constant, dynamic modulation of fibroblast cell attachment was enabled. Host-guest interactions between cyclodextrin and naphthyl- or adamantane-functionalized peptides allow alginate functionalization, this may be applied to other appropriate biomolecules.

In some cases, biotin-(strept)avidin may be utilized for bioconjugation. For example, avidin and streptavidin are homotetrameric proteins that can simultaneously bind up to four molecules of their small molecule binding partner biotin. The small size of biotin (with a mass of just 244 Da) and the ease with which it can be functionalized via its free carboxylic acid has led to biotin-(strept)avidin binding finding widespread use as a means to undertake biomaterial conjugation. Streptavidin-protein fusions can be produced recombinantly and bound to suitably functionalized surfaces to achieve conjugation. In some cases, biomolecule biotinylation is undertaken, and this construct is then bound to a (strept)avidin functionalized surface. In some cases, this can either be achieved by a direct route, via chemical preconjugation of the material with (strept)-avidin, or by exploiting the tetrameric binding of (strept)avidin to mediate indirect modification or cross-linking of biotin-functionalized scaffolds.

In some cases, nucleic acids may be utilized for bioconjugation. In some cases, in an analogous fashion to self-assembling peptides, nucleic acids can also form assembled materials themselves, to generate tunable platforms for the display of biomolecules. In some cases, DNA-tagged peptides and growth factors can be conjugated to a suitably functionalized biomaterial and used to elicit a desired biological effect on a localized cell population.

Generally, incorporating reactive handles may be utilized for bioconjugation. For example, introducing uniquely reactive motifs into biomolecule substrates provides a chemical "tag" which allows single-site selectivity or specificity to be achieved. In some cases, short peptides and oligonucleotides can typically be produced via solid phase synthesis (SPS). The versatility of organic synthesis allows difficulties in reactive handle incorporation to be overcome, with a wide range of suitably functionalized amino acids and oligonucleotides available as described herein. In some cases, an alternative approach is to introduce unnatural amino acids (UAAs) bearing the desired reactive handles. This may be achieved via the modification of lysine residues with amine-reactive derivatives. In some cases, the use of auxotrophic bacterial strains, which are unable to biosynthesise a particular amino acid and thus require uptake from the growth media, by starving the bacteria of the native amino acid and supplementing it with a structurally related unnatural analogue, the bacterial cells can will incorporate the UAA during translation. This technique may be used to install azide- and alkyne-based mimics of methionine, leading to the introduction of reactive handles for undertaking CuAAC and SPAAC reactions. Analogous strategies can be used for the incorporation of unnatural monosaccharides, enabling the remodelling of complex glycans. In some cases, the use of codon reassignment using orthogonal tRNA and tRNA synthetase pairs that selectively recognize and charge an UAA during translation. In some cases, this may be achieved by reassigning the amber stop-codon, UAG, by incorporating a $tRNA_{CUA}$/RNA synthetase pair from an alternative kingdom into the host cell. This pair may be able to install the desired UAA, while being effectively invisible to the endogenous cell machinery. As a result, site-directed mutagenesis can be used to introduce a single TAG codon at the desired position of the coding DNA, leading to the singular introduction of the UAA with high specificity and selectivity.

In some cases, one or more functional groups may release a reporter when reacted with another functional group, or with a SNAP or biological entity or chemical entity. Having a reporter released when the SNAP and biological or chemical entity are conjugated may allow tracking of the reaction. In some cases, it may be possible to monitor the degree of completion of a SNAP-biological/chemical entity conjugation reaction by monitoring the concentration of free reporter. In some cases, the reporter may fluoresce once released by the conjugation reaction.

In some cases, the biological or chemical entity may be functionalized with a linker. In some cases, functionalizing the biological or chemical entity with a linker may decrease steric hindrance. A linker may comprise a rigid or semi-rigid moiety which can hold the biological or chemical entity away from the SNAP. In some cases, the linker may be a long, moderate or short linker. In some cases, the linker may comprise one or more component selected from PEG, DNA, short carboxyl, carbon chain, peptoid, spacer, and/or glycer, among other examples.

In some cases, the SNAPs, seeds, and/or biological or chemical entities may be functionalized using single pot proteomics methods. Single pot proteomics methods may result in very high efficiency of functionalization. In some cases, single pot proteomics methods may be useful to functionalize biological or chemical entities with very low levels of loss of the entities.

In some embodiments, a SNAP is a polymer which may be grown from the seed. For example if the seed is a DNA oligonucleotide then the SNAP may be a DNA molecule. In some cases, the SNAP may be a DNA molecule with regions of internal complementarity such that the molecule may self-hybridize. For example, the SNAP may be a DNA cluster, formed by self hybridization within the molecule. In some cases, the SNAP may be formed from DNA, RNA, L-DNA, L-RNA, LNA, PNA, or a mixture of two or more different types of nucleic acid. In some cases, the SNAP may have a repeating structure, such as a repeating sequence of nucleotides. In some cases, the SNAP may be an irregular polymer without a repeating sequence. For example, the SNAP may comprise a random sequence of nucleotides.

In some cases, a SNAP may be formed by rolling circle amplification. A plasmid, or other circular nucleic acid molecule, may be provided as a template, together with a primer that binds to the circular nucleic acid molecule, wherein the primer comprises a functional group on the 5' end. Performing a polymerase chain reaction (PCR) with a sufficiently long extension step, or merely a polymerase extension reaction, will allow the functionalized primer to bind the circular nucleic acid molecule and produce a single stranded nucleic acid product. The length of the single stranded nucleic acid product may be influenced by altering the extension time, the polymerase enzyme used, or the reaction conditions. In some cases, the circular nucleic acid template contains regions of internal complementarity, such that the single stranded nucleic acid product will contain regions which may self-hybridize. In some cases, the circular nucleic acid template is a dsDNA molecule. In some cases, the single stranded nucleic acid product is an ssDNA molecule. In some cases, the polymerase used is a DNA polymerase.

In some cases, a SNAP may be formed by nucleic acid origami, or DNA origami. DNA origami generally refers to the nanoscale folding of DNA to create non-arbitrary two- and three-dimensional shapes at the nanoscale. The specificity of the interactions between complementary base pairs can make DNA a useful construction material. In some cases, the interactions between different regions may be controlled through design of the base sequences. DNA origami may be used to create scaffolds that hold other molecules in place or to create structures all on its own.

SNAPs as described herein can include those created via nucleic acid origami. Commonly, nucleic acid origami can refer to DNA origami, but it can also refer to RNA origami, origami of a combination of DNA and RNA molecules, or origami of nucleic acid molecules which can be other than DNA or RNA, such as a silicon-based nucleic acid, among other examples. Nucleic acid origami can result in a nucleic acid molecule which has an engineered shape. The engineered shape can be a shape which has been partially or fully planned. The planning of the shape can comprise planning or engineering what sections of nucleic acid bind, where a segment of nucleic acid can fold, where a segment of nucleic acid can be single stranded, where a segment of nucleic acid can be double stranded, where a segment of nucleic acid can be bound to a segment of nucleic acid of the same strand, or where a segment of nucleic acid can be bound to a segment of nucleic acid on another strand. In some cases, non-nucleic acid molecules, such as protein, can be used to encourage nucleic acid into the engineered shape.

Generally, nucleic acid origami can comprise at least one or more long nucleic acid strand and one or more short nucleic acid strands. Commonly, these nucleic acid strands are single stranded, although they can have segments which can be double stranded. One of the short strands can comprise at least a first segment which can be complementary to a first segment of the long strand, as well as a second segment which can be complementary to a second segment of the long strand. When the short and long strands are incubated under conditions that can allow hybridization of nucleotides, the shorter oligonucleotide can hybridize with the longer oligonucleotide. This hybridization can give shape to the nucleic acid molecule. For example, if the two segments on the first strand are separated, then these two segments can be brought together during hybridization to create a shape. In some cases, a short strand can bind to at least 2, 3, 4, 5, or 6 segments which can bind to at least 2, 3, 4, 5, or 6 complementary segments of the long nucleic acid strand.

In some cases, a short strand can have one or more segments which can be not complementary to the long strand. In such a case, the segment which is not complementary to the long strand can be at least about 1, 2, 3, 4, 5, 10, 15, or 20 nucleotides long.

This process can be performed with at least about 1, 2, 3, 4, 5, 6, 7, 8, 9, 10, 15, 20, 30, 40, 50, 60, 70, 80, 90, 100, 150, 200, 250, 300, or more short nucleic acid strands. These short nucleic acid strands can each bind to one or more different segments of the long nucleic acid strand. Each short nucleic acid strand which hybridizes to the long nucleic acid strand can lead to a fold in the long nucleic acid strand. In some cases, the number of short strands can be correlated with the complexity of the engineered shape. For example, an engineered shape with many folds can utilize more short nucleic acid strands than an engineered shape with few folds. An engineered shape can have at least about 1, 2, 3, 4, 5, 6, 7, 8, 9, 10, 15, 20, 30, 40, 50, 60, 70, 80, 90, 100, 150, 200, 250, 300, or more folds.

In some cases, more than one long strand can be incorporated into the nucleic acid origami structure. This can be done for example to increase the complexity of the engineered shape, to ease the designing or planning of the engineered shape, to avoid the creating of a shape which is more thermodynamically stable than the desired engineered shape, to make the creation of the engineered shape easier, or to manage costs of creating the engineered shape.

Incorporation of more than one long strand can be accomplished by designing the 2 or more long strands such that each strand has at least one segment that can be complimentary to a segment of the other strand, or by designing the 2 or more long strands such that each has at least one segment which can be complementary to a region of a short nucleic acid strand, such that both long strands have segments complementary to the short nucleic acid strand.

Short nucleic acid strands can have complementarity to one long nucleic acid strand or more than one long nucleic acid strand. In some cases, a short nucleic acid strand can also have complementarity to one or more short nucleic acid strands.

The terms "long" and "short" herein are meant to be general terms. A long strand can be longer than a short strand, although in some instances a long strand can be the same size as a short strand. In some cases, a long strand can be at least about 30, 40, 50, 100, 150, 200, 250, 300, 400, 500, 600, 700, 800, 900, 1000, or more nucleotides long. In some cases, a short strand can be at least about 6, 7, 8, 9, 10, 15, 20, 25, 30, 35, 40, 45, 50, 60, 70, 80, 90, 100, or more nucleotides long.

An engineered shape can be designed for a specific purpose. For example, an engineered shape can be designed to support a load, encapsulate a molecule, bind a molecule, connect two or more molecules, fit into a cavity, bind a protuberance, or other purpose. An engineered shape can any shape, such as oblong, rectangular, round, circular, spherical, flat, textured, smooth, symmetrical, asymmetrical, conical, or irregular. An engineered shape can be a cube, pyramid, boxe, cage, ladder, or tree.

An engineered shape or SNAP formed via nucleic acid origami as described above can be assembled. Assembly can refer to the process by which the nucleic acid strands hybridize to each other to create the engineered shape.

An engineered shape or SNAP can be spontaneously self-assembling. Self-assembly can occur when long and short oligonucleotides having regions which can be complimentary are incubated together. During spontaneous self-assembly, the nucleotides can hybridize and the engineered shape can be created during incubation without the help of a helper molecule or catalyst. Such self-assembling can occur under specific conditions or a range of specific conditions. Conditions which can be considered when incubating DNA strands for self-assembly can be salt concentration, temperature, and time.

Sometimes, assembly can utilize or require a catalyst. In such cases, the catalyst can speed up assembly or ensure the assembly results in a particular desired engineered shape. A catalyst can comprise RNA, DNA, or protein components.

The salt concentration during assembly can be less than 1 M, less than 0.5M, less than 0.25 M, less than 0.1M, less than 0.05 M, less than 0.01 M, less than 0.005 M, or less than 0.001 M.

The temperature during assembly can be at least room temperature. In some cases, the temperature during assembly can be at least about 50, 60, 70, 80, 85, 90, or 95° C. In some cases, the temperature during assembly can vary. For instance, the temperature can be increased to at least about 20, 30, 40, 50, 60, 70, 80, 85, 90, or 95° C. This increase can ensure the nucleic acid strands do not comprise a secondary structure prior to assembly. Once the temperature is increased as described, it can be decreased, for example to about 20, 30, 40, 50, 60, 70, or 80° C. This decrease in temperature can allow the nucleic acids to hybridize. In some cases, the decrease in temperature can occur over about 0.5, 1, 2, 3, 4, 5, 10, 15, 20, 25, 30, 45, or 60 minutes.

Assembly can be performed stepwise. In such cases, a subset of the nucleic acid molecules can be incubated together first. After these molecules are allowed to hybridize, one or more additional nucleic acid molecules can be added and allowed to hybridize. In some cases, two or more engineered shapes which have been assembled can be incubated together for assembly into a larger engineered shape.

In some cases, assembly can comprise fractal assembly. Fractal assembly can create a SNAP which can be an array of engineered shapes. Assembly can occur in stages, which can simplify the design process or ensure correct assembly. Such an array can be assembled in at least 1, 2, 3, 4, 5, 10, 15, 20, 30, 40, 50, 60, 70, 80, 90, 100, 200, 300, 400, 500, 1000, or more stages. In some cases, the number of stages used can correlate with a reduction of spurious interactions. This can be due to a reduction in the total number of possible reactions at any given time.

SNAPs can be assembled into an array which can be at least 3×3, at least 5×5, at least 10×10, at least 50×50, at least 100×100, or at least 1000×1000 (engineered shapes×engineered shapes).

Each hybridization reaction can take about 10, 20, 30, 40, 50, or 60 seconds. In some cases, each hybridization reaction can take about 1, 2, 3, 4, 5, 10, 15, 20, 30, 40, 50, or 60 minutes. In some cases, a hybridization reaction can take more than 1 hour.

Nucleic acid origami may be used to preferentially choose how the SNAP will "land" on the solid support. For example, nucleic acid origami may be used to construct a SNAP with a landing surface that can preferentially contact the solid support, A SNAP such as one made via nucleic acid origami can be designed to comprise a region that can create steric or electrostatic interactions with the support that can influence the orientation of the SNAP on the support. For example, the region can comprise nucleotides having modifications e.g. to the backbone of the nucleic acid which can promote interaction between the SNAP and the solid support. In further examples, the region can comprise protuberances or cavities which can "fit" to cavities or protuberances on the solid support. In some cases, the support surface can comprise chemical structuring (e.g. nanoparticles or oligonucleotides), click reagents, or other rationally designed materials that can influence the position and orientation of SNAP structures, including SNAPs synthesized via nucleic acid origami.

Nucleic acid origami can be used to construct a SNAP with a linker which can attach a biological or chemical entity, wherein the linker is positioned relative to the landing surface such that the biological or chemical entity can be distal or approximately distal to the solid support. The linker may also comprise a region of dsDNA to force a rigid outpost from the SNAP. In some cases, protein origami may also be used.

A surface can have properties such that a SNAP can bind to the surface in such a way that it can flop or lean. The SNAP can flop or lean to the left, to the right, to the front, to the back, or to any combination of sides thereof. The SNAP can flop or lean once and remain in place, or it can flop freely between sides over time. In some cases, the SNAP can preferentially flop in one direction over one or more other directions. In some cases, the SNAP can preferentially avoid flopping in a particular direction.

In some cases, for example, filamentous or stranded molecules, such as nanoparticles or oligonucleotide strands, can be attached to a surface. A SNAP, which can comprise an engineered shape, can comprise one or more moieties which can bind to a filamentous or stranded molecule, such as a dangling single stranded oligonucleotide or nanoparticle. Upon contacting the surface with such SNAPs, the one or more moieties can interact with one or more of the filamentous or stranded molecules. In some cases, the moieties can bind tightly to the filamentous or stranded molecules. The SNAPs can be removable or non-removable in such cases.

Computational modeling or simulation tools may be employed to design and optimize oligonucleotide or protein sequences to create particular SNAP structures.

In some cases, a SNAP may be a nucleic acid plasmid, such as a DNA plasmid. Plasmids may exist in a compact form known as supercoiled DNA. The radii of a supercoiled plasmid may be determined by the plasmid size—i.e. a plasmid with a longer backbone will form a larger supercoiled entity. In some cases, a SNAP may comprise a plasmid with a backbone of between 5 kb and 150 kb. In some cases, a SNAP may comprise a plasmid with a backbone of between 5 kb and 100 kb. In some cases, a SNAP may comprise a plasmid with a backbone of between 5 kb and 90 kb. In some cases, a SNAP may comprise a plasmid with a backbone of between 25 kb and 50 kb. In some cases, a SNAP may comprise a plasmid with a backbone of at least about 5 kb, 10 kb, 15 kb, 20 kb, 25 kb, 30 kb, 35 kb, 40 kb, 45 kb, 50 kb, 55 kb, 60 kb, 65 kb, 70 kb, 75 kb, 80 kb, 85 kb, 90 kb, 95 kb, 100 kb, 105 kb, 110 kb, 115 kb, 120 kb, 125 kb, 130 kb, 135 kb, 140 kb, 145 kb, or 150 kb. In some embodiments, SNAPs may be imaged using an imaging platform, such as Nanocyte or Leica.

In some cases, a SNAP may have a branched structure. For example the SNAP may be a dendrimer. Some examples of dendrimers may be found in Newkome, George R., and Carol D. Shreiner. "Poly (amidoamine), polypropylenimine, and related dendrimers and dendrons possessing different 1→2 branching motifs: an overview of the divergent procedures." Polymer 49.1 (2008): 1-173. A dendrimer used with the methods of this disclosure may be a G1, G2, G3, G4, G5, G6, G7, G8, G9, G10, G11, G12, G13, G14, or G15 dendrimer. In some cases, the dendrimer may be higher than a G15 dendrimer, for example dendrimer between G15 and G30.

In some embodiments, the SNAP may be a protein, or comprised of proteins. For example the SNAP may be a protein fibril. The SNAP may be comprised of proteins known to form into fibrils, such as, for example, the tau protein, or portions of the tau protein. A 31 residue portion of tau which assembles into fibrils is described in Stöhr, Jan, et al "A 31-residue peptide induces aggregation of tau's microtubule-binding region in cells." *Nature chemistry* 9.9 (2017): 874. In some cases, the SNAP may comprise tetratricopeptide repeats. Examples of tetratricopeptide repeats may be found in Blatch, Gregory L., and Michael Lässie. "The tetratricopeptide repeat: a structural motif mediating protein-protein interactions." *Bioessays* 21.11 (1999): 932-939. Other examples of proteins which may assemble may be found in Speltz, Elizabeth B., Aparna Nathan, and Lynne Regan. "Design of protein-peptide interaction modules for assembling supramolecular structures in vivo and in vitro." *ACS chemical biology* 10.9 (2015): 2108-2115.

In some embodiments, the SNAP may be a single molecule. In some embodiments the SNAP may not be a single molecule. In some cases, the SNAP may be assembled from several molecules which bind non-covalently. For example the SNAP may be formed from two or more nucleic acid molecules which hybridize together. In another example the SNAP may be formed from two or more protein molecules which assemble together via non-covalent bonds.

In some embodiments, the SNAPs are between about 50 nm and about 100 um in diameter.

The SNAPs are generally polymeric molecules. These may be grown through a controlled polymerization reaction, a stepwise polymerization reaction, or a step by step synthesis method. The growth of the SNAPs may be controlled by the amount of monomers available, the length of time the reaction is allowed to proceed, or the number of synthesis steps performed.

Each SNAP may have a diameter of at least about 10 nanometers (nm), or about 10 nm, about 50 nm, about 75 nm, about 100 nm, about 125 nm, about 150 nm, about 175 nm, about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, about 800 nm, about 825 nm, about 850 nm, about 875 nm, about 900 nm, about 925 nm, about 950 nm, about 975 nm, about 1000 nm, about 1025 nm, about 1050 nm, about 1075 nm, about 1100 nm, about 1125 nm, about 1150 nm, about 1175 nm, about 1200 nm, about 1225 nm, about 1250 nm, about 1275 nm, about 1300 nm, about 1325 nm, about 1350 nm, about 1375 nm, about 1400 nm, about 1425 nm, about 1450 nm, about 1475 nm, about 1500 nm, about 1525 nm, about 1550 nm, about 1575 nm, about 1600 nm, about 1625 nm, about 1650 nm, about 1675 nm, about 1700 nm, about 1725 nm, about 1750 nm, about 1775 nm, about 1800 nm, about 1825 nm, about 1850 nm, about 1875 nm, about 1900 nm, about 1925 nm, about 1950 nm, about 1975 nm, about 2000 nm, about 3000 nm, about 4000 nm, about 5000 nm, about 6000 nm, about 7000 nm, about 8000 nm, about 9000 nm, about 10 µm, about 15 µm, about 20 µm, about 25 µm, about 30 µm, about 40 µm, about 50 µm, about 75 µm, about 100 µm, about 200 µm, about 300 µm, about 400 µm, about 500 µm, or more than about 500 µm. In some cases, the SNAP may have a diameter between about 100 nm and 500 nm, between about 200 nm and about 400 nm, between about 500 nm and about 10 µm, or between about 1000 nm and about 10 µm.

In some cases the SNAPs may be covalently attached to the solid support using a click chemistry. Generally, the term "click chemistry" is used to describe reactions that are high yielding, wide in scope, create only byproducts that can be removed without chromatography, are stereospecific, simple to perform, and can be conducted in easily removable or benign solvents (McKay, C., & Finn M. G. (2014) Click Chemistry in Complex Mixtures Bioorthogonal Bioconjugation vol 21, Issue 9, pp 1075-1101; M. G. Meldal, M., & Tornoe, C. W. (2008). Cu-Catalyzed Azide-Alkyne Cycloaddition. Chemical Reviews, 108(8), 2952-3015; Lutz, J., & Zarafshani, Z. (2008). Efficient construction of therapeutics, bioconjugates, biomaterials and bioactive surfaces using azide-alkyne "click" chemistry. Advanced Drug Delivery Reviews, 60(9), 958-970, herein incorporated by reference).

In some cases, the click chemistry reaction may be a CuAAC, SPAAC, SPANC, or as described elsewhere herein. In some cases, the click chemistry reaction may need a copper source such as, for example, $CuSO_4$, Cu(0), CuBr$(Ph_3P)_3$, CuBr, $CuBr/Cu(OAc)_2$, $CuBr_2$, [Cu(CH3CN)4] PF6, PS-NMe2:CuI, silica:CuI, (EtO)3P:CuI, CuCl/Pd2 (dba)3, $CuBF_4$, CuCl, $CuCl_2$, $Cu(AcO)2$, Cu(2), TTA: CuSO4, Cu(1) zeolite (USY), Cu(CH3CN)4OTf, CuOTf, Cu(2):bis-batho, or a combination thereof. In some cases a copper source is not needed for the click chemistry reaction to proceed. In some cases, the reducing agent of the click chemistry reaction may be, for example, NaAsc, air, ICl, oxygen, $N_2$, HAsc, TCEP, dithithreitol (DTT), PPh3, mercaptoethanol, tris(2-carboxyethyl)phosphine (TCEP), TCEPT-hydrochloric acid a combination thereof, or no reducing agent. In some cases, the solvent of the click chemistry reaction may be, for example, THF, pyridine, DMSO, DMF, toluene, NMP, acetonitrile, water, tBuOH, iBuOH, EtOH, MeOH, dioxane, dichloromethane, HEPES, NaCl buffer, acetone, PBS, SFM, Tris buffer, borate buffer, PB, TFH, AcOEt, PIPES, urea, acetone, Tris, saline, $AllOCO_2Me$, $TMS-N_3$, urea solution, bicarbonate buffer, a combination thereof, or no solution. In some cases, the base of the click chemistry reaction may be, for example, DIPEA, Lut Na2CO3, $iPr_2NH$, DBU, $Et_3N$, $Et_3N.HCl$, $Et_3NH+$-OAc, $K_2CO_3$, TBAF, $CuSO_4$, $PS-NMe_2$, piperidine, a desired pH, or a combination thereof. In some cases, the ligand of the click chemistry reaction may be, for example, TBTA, proline, BMAH, Lut, chiral Lig's, pyridine, His, Batho, TTA, Bim, Phen, Bipy, PMDETA, dNbipy, TRMEDA, or a combination thereof. In some cases, the temperature of the click chemistry reaction may be, for example, 0-5° C., 5-15° C., 15-25° C., 20-25° C., 25-35° C., 35-45° C., 45-55° C., 55-65° C., 65-75° C., 75-85° C., 85-95° C., or greater. In some cases, the temperature of the click chemistry reaction may be less than 0° C. In some reactions, the click chemistry reaction may be covered by aluminum foil. In some cases, the click chemistry reaction may include an acid, for example, trifluoroacetic acid, trichloroacetic acid, or tribromoacetic acid.

In some cases, a crosslinker may be used for conjugation. In some cases, the crosslinker may be a zero-length crosslinker, homobifunctional crosslinker, heterobifunctional crosslinker, or a trifunctional cross linker. Crosslinkers may be incorporated into a biomolecule preformed or in-situ.

In some cases, zero-length crosslinkers mediate the conjugation for bioconjugation by forming a bond containing no additional atoms. Thus, one atom of a molecule is covalently attached to an atom of a second molecule with no intervening linker or spacer. In so conjugation schemes, the final complex is bound together by virtue of chemical components that add foreign structures to the substances being crosslinked. Carbodiimides may be used to mediate the formation of amide linkages between carboxylates and amines or phosphoramidate linkages between phosphates and amines and are popular type of zero-length crosslinker that may be used, being efficient in forming conjugates between two protein molecules, between a peptide and a protein, between an oligonucleotide and a protein, between a biomolecule and a surface or particle, or any combination of these with small molecules. In some cases, EDC (or EDAC; 1-ethyl-3-(3-dimethylaminopropyl) carbodiimide hydrochloride) may be used for conjugating biomolecules containing carboxylates and amines. In some cases, CMC, or 1-cyclohexyl-3-(2-morpholinoethyl) carbodiimide (usually synthesized as the metho p-toluene sulfonate salt), is a water soluble reagent used to form amide bonds between one molecule containing a carboxylate and a second molecule containing an amine that may be used as a crosslinker for bioconjugation. In some cases, DIC, or diisopropyl carbodiimide may be used for bioconjugation as a zero-length crosslinker. In some cases, DCC (dicyclohexyl carbodiimide) may be used for bioconjugation as a zero-length crosslinker. In some cases, Woodward's reagent K is N-ethyl-3-phenylisoxazolium-3'-sulfonate, a zero-length crosslinking agent able to cause the condensation of carboxylates and amines to form amide bonds. In some cases, CDI, or N,N'-carbonyl diimidazole may be used for bioconjugation as a zero-length crosslinker. In some cases, schiff base formation and reductive amination may be used for bioconjugation as a zero-length cross linker.

In some cases, homobifunctional crosslinkers mediate the conjugation for bioconjugation. In some cases, homofunctional NHS esters may be used for bioconjugation. For example, Lomant's reagent [(dithiobis(succinimidylpropionate), or DSP]) is a homobifunctional NHS ester crosslinking agent containing an eight-atom spacer 12 Å in length. The sulfo-NHS version of DSP, dithiobis(sulfosuccin-imidylpropionate) or DTSSP, is a water soluble analog of Lomant's reagent that can be added directly to aqueous reactions without prior organic solvent dissolution. In some cases, disuccinimidyl suberate (DSS), an amine-reactive, homobifunctional, NHS ester, crosslinking reagent produces an eight-atom bridge (11.4 Å) between conjugated biomolecules. In some cases, disuccinimidyl tartarate (DST), a homobifunctional NHS ester crosslinking reagent that contains a central diol that is susceptible to cleavage with sodium periodate may be used forms amide linkages with α-amines and ε-amines of proteins or other amine-containing molecules. In some cases, BSOCOES [bis[2-(succinim-idyloxycarbonyloxy)ethyl] sulfone], a water-insoluble, homobifunctional NHS ester crosslinking reagent that contains a central sulfone group, where the two NHS ester ends are reactive with amine groups in proteins and other molecules to form stable amide linkages. In some cases, ethylene glycolbis(succinimidylsuccinate) (EGS), a homobifunctional crosslinking agent that contains NHS ester groups on both ends. The two NHS esters are amine reactive, forming stable amide bonds between cross-linked molecules within a pH range of about 7 to 9. In some cases, disuccinimidyl glutarate (DSG), a water-insoluble, homobifunctional crosslinker containing amine-reactive NHS esters at both ends, may be used for bioconjugation. In some cases, N,N'-Disuccinimidyl carbonate (DSC), the smallest homobifunctional NHS ester crosslinking reagent available may be used. In some cases, Dimethyl adipimidate (DMA), Dimethyl pimelimidate (DMP), Dimethyl suberimidate (DMS), dimethyl 3,3'-dithiobispropionimidate (DTBP), 1,4-di-[3'-(2'-pyridyldithio)propionamido] butane, bismaleimidohexane, 1,5-difluoro-2,4-dinitrobenzene or 1,3-difluoro-4,6-dinitrobenzene, DFDNPS (4,4'-difluoro-3,3'-dinitrophenylsulfone), Bis-[β-(4-azidosalicylamido)ethyl]disulfide (BASED), formaldehyde, Glutaraldehyde, 1,4-butanediol diglycidyl ether, adipic dihydrazide, carbohydrazide, 3,3'-dimethylbenzidine, p-diaminodiphenyl, or haloacetyl derivatives may be used as homobifunctional crosslinkers.

In some cases, heterobifunctional crosslinkers mediate the conjugation for bioconjugation. Heterobifunctional reagents can be used to crosslink proteins and other molecules in a two- or three-step process. In some cases, one protein is modified with a heterobifunctional compound using the crosslinker's most reactive or most labile end. The modified protein may then be purified from excess reagent by gel filtration or rapid dialysis. In some cases, heterobifunctionals contain at least one reactive group that displays extended stability in aqueous environments, therefore allowing purification of an activated intermediate before adding the second molecule to be conjugated. For instance, an N-hydroxysuccinimide (NHS ester-aleimide hetero-bifunctional can be used to react with the amine groups of one protein through its NHS ester end (the most labile functionality), while preserving the activity of its maleimide functionality. Since the maleimide group has greater stability in aqueous solution than the NHS ester group, a maleimide-activated intermediate may be created. After a quick purification step, the maleimide end of the crosslinker can then be used to conjugate to a sulfhydryl-containing molecule. Heterobifunctional crosslinking reagents may also be used to site-direct a conjugation reaction toward particular parts of target molecules. In some cases, amines may be coupled on one molecule while sulfhydryls or carbohydrates are targeted on another molecule. In some cases, heterobifunctional reagents containing one photo-reactive end may be used to insert nonselectively into target molecules by UV irradiation. Another component of heterobifunctional reagents is the cross-bridge or spacer that ties the two reactive ends together. Crosslinkers may be selected based not only on their reactivities, but also on the length and type of cross-bridge they possess. Some heterobifunctional families differ solely in the length of their spacer. The nature of the cross-bridge may also govern the overall hydrophilicity of the reagent. For instance, polyethylene glycol (PEG)-based cross-bridges create hydrophilic reagents that provide water solubility to the entire heterobifunctional compound. In some cases, a number of heterobifunctionals contain cleavable groups within their cross-bridges, lending greater flexibility to the experimental design. A few crosslinkers contain peculiar cross-bridge constituents that actually affect the reactivity of their functional groups. For instance, it is known that a maleimide group that has an aromatic ring immediately next to it is less stable to ring opening and loss of activity than a maleimide that has an aliphatic ring adjacent to it. In addition, conjugates destined for use in vivo may have different properties depending on the type of spacer on the associated crosslinker. Some spacers may be immunogenic and cause specific antibody production to occur against them. In other instances, the half-life of a conjugate in vivo may be altered by the choice of cross-bridge, especially when using cleavable reagents. In some cases, the heterobifunctional crosslinker may be N-succinimidyl 3-(2-pyridyldithio)propionate (SPDP), standard SPDP, LC-SPDP, sulfo-LC-SPDP, succinimidyloxycarbonyl-α-methyl-α-(2-pyri-dyldithio) toluene, succinimidyl-4-(N-maleimidomethyl)cyclo-hexane-1-carboxylate, sulfosuccinimidyl-4-(N-maleimidomethyl) cyclohexane-1-carboxylate, m-maleimidobenzoyl-N-hydroxysuccinimide ester, m-maleimidobenzoyl-N-hydroxysulfo-succinimide ester, N-succinimidyl(4-iodoacetyl)aminobenzoate, sulfosuccinimidyl(4-iodoacetyl)amino-benzoate, succinimidyl-4-(p-maleimidophenyl)butyrate, N-(γ-maleimidobutyryloxy) succinimide ester, succinimidyl-3-(bromoacetamide) propionate, succinimidyl iodoacetate, 4-(4-N-maleimidophenyl)butyric acid hydrazide, 4-(N-maleimidomethyl)cyclohexane-1-carboxyl-hydrazide, 3-(2-pyridyldithio)propionyl hydrazide, N-hydroxysuccinimidyl-4-azidosalicylic acid, sulfosuccinimidyl-2-(p-azidosalicylamido) ethyl-1,3'-dithiopropionate, N-hydroxysulfosuccinimidyl-4-azido-benzoate, N-succinimidyl-6-(4'-azido-2'-nitrophenylamino)hexanoate, sulfosuccinimidyl-6-(4'-azido-2'-nitrophenylamino)hexanoate, N-5-Azido-2-nitrobenzoyloxysuccinimide, Sulfosuccinimidyl-2-(m-azido-o-nitrobenzamido)-ethyl-1,3'-dithiopropionate, N-succinimidyl-(4-azidophenyl) 1,3'-dithiopropionate, sulfosuccinimidyl 4-(p-azidophenyl) butyrate, Sulfosuccinimidyl 2-(7-azido-4-methylcoumarin-3-acetamide)ethyl-1,3'-dithiopropionate, sulfosuccinimidyl 7-azido-4-methylcoumain-3-acetate, p-Nitrophenyl diazopyruvate, p-nitrophenyl-2-diazo-3,3,3-trifluoropropionate, 1-(p-azidosalicylamido)-4-(iodoacetamido)butane, N-[4-(p-azidosalicylamido)butyl]-3'-(2'-pyridyldithio) propionamide, Benzophenone-4-maleimide, p-azidobenzoyl hydrazide, 4-(p-azidosalicylamido)butylamine, or p-azidophenyl glyoxal.

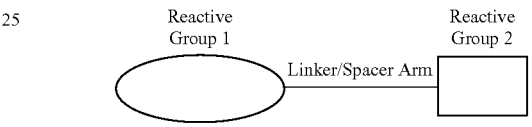

Other examples of crosslinkers, but not limited to, may be NHS-PEG$_4$-Azide, NHS-phosphine, N-γ-maleimidobutyryl-oxysulfosuccinimide ester, m-maleimidobenzoyl-N-hydroxysuccinimide ester, sulfosuccinimidyl (4-iodoacetyl)aminobenzoate, succinimidyl 3-(2-pyridyldithio)propionate), sulfosuccinimidyl (4-iodoacetyl)aminobenzoate, m-maleimidobenzoyl-N-hydroxysuccinimide ester, 1-Ethyl-3-[3-dimethylaminopropyl]carbodiimide hydrochloride, dimethyl pimelimidate, sulfosuccinimidyl 6-(3'-(2-pyridyldithio)propionamido)hexanoate, 6-(3'[2-pyridyldithio]-propionamido) hexanoate, tris-(succinimidyl)aminotriacetate, Sulfo-NHS-LC-Diazirine, bismaleimidohexane, 1,4-bismaleimidobutane, sulfosuccinimidyl 4-(N-maleimidophenyl)butyrate, Sulfo-SBED Biotin Label Transfer Reagent, succinimidyl 6-(3(2-pyridyldithio)propionamido)hexanoate, succinimidyl 3-(2-pyridyldithio)propionate, sulfosuccinimidyl 6-(3'-(2-pyridyldithio)propionamido)hexanoate, L-Photo-Leucine, L-Photo-Methionine, sulfosuccinimidyl 4-(N-maleimidomethyl)cyclohexane-1-carboxylate, Pierce BS(PEG)5, sulfosuccinimidyl 2-((4,4'-azipentanamido)ethyl)-1,3'-dithiopropionate, Sulfo-NHS-SS-Diazirine, Pierce SM(PEG)n, NHS-dPEG-Mal, N-hydroxysulfosuccinimide, sulfosuccinimidyl 4-(N-maleimidomethyl)cyclohexane-1-carboxylate, Sulfosuccinimidyl-4-(N-maleimidomethyl)cyclohexane-1-carboxylate, 1-Ethyl-3-(3-Dimethylaminopropyl)carbodiimide Hydrochloride, N-α-maleimidoacet-oxysuccinimide ester, Sulfo-NHS-LC-Biotin, bis(sulfosuccinimidyl)suberate, trans-4-(maleimidylmethyl)cyclohexane-1-Carboxylate, bismaleimidohexane, 1,8-bismaleimido-diethyleneglycol, N-β-maleimidopropionic acid hydrazide, N-succinimidyl 3-(2-pyridyldithio)-propionate, sulfosuccinimidyl 4-(N-maleimidomethyl)cyclohexane-1-carboxylate, 3-(2-pyridyldithio)propionyl hydrazide, 4-(4-N-maleimidophenyl)butyric acid hydrazide, 3,3'-dithiobis(sulfosuccinimidyl propionate, bis(sulfosuccinimidyl) 2,2,4,4-glutarate-d4, or Succinimidyl-4-(N-maleimidomethyl)cyclohexane-1-carboxylate.

In some cases, the alkyne derivative attached to the solid support or SNAP may be, for example, dibenzocyclooctyne-amine, dibenzocyclooctyne-acid, dibenzocyclooctyne-N-hydroxysuccinimidyl ester, dibenzocyclooctyne-N-hydroxysuccinimidyl ester, dibenzocyclooctyne-sulfo-N-hydroxysuccinimidyl ester, ibenzocyclooctyne-sulfo-N-hydroxysuccinimidyl ester, Dibenzocyclooctyne-S—S—N-hydroxysuccinimidyl ester, dibenzocyclooctyne-PEG4-N-hydroxysuccinimidyl ester, dibenzocyclooctyne-PEG4-acid, dibenzocyclooctyne-maleimide, sulfo-dibenzocyclooctyne-biotin conjugate, (1R,8S,9s)-Bicyclo[6.1.0]non-4-yn-9-ylmethyl N-succinimidyl carbonate, (1R,8S,9s)-Bicyclo6.1.0non-4-yn-9-ylmethanol, APN-BCN, (1R,8S, 9s)-Bicyclo6.1.0non-4-yn-9-ylmethanol, ethyl (1R,8S,9s)-bicyclo6.1.0non-4-ene-9-carboxylate, Alkyne-PEG5-acid, (R)-3-Amino-5-hexynoic acid hydrochloride, (S)-3-Amino-5-hexynoic acid hydrochloride, (R)-3-(Boc-amino)-5-hexynoic acid, (S)-3-(Boc-amino)-5-hexynoic acid, N-Boc-4-pentyne-1-amine, 4-pentyne-1-amine, Boc-propargyl-Gly-OH, 3-Ethynylaniline, 4-Ethynylaniline, PC biotin-alkyne, Propargyl chloroformate, Propargyl-N-hydroxysuccinimidyl ester, N—Z-4-pentyne-1-amine, 1-Azido-2-(2-(2-ethoxyethoxy)ethoxy)ethane, O-(2-Azidoethyl)heptaethylene glycol, Click-iT® DIBO-Alexa Fluor® 488, Click-iT® DIBO-Alexa Fluor® 555, Click-iT® DIBO-Alexa Fluor® 594, Click-iT® DIBO-Alexa Fluor® 647, Click-iT® DIBO TAMRA, Click-iT® DIBO-biotin, Click-iT® DIBO-amine, Click-iT® DIBO-maleimide, Click-iT® DIBO-succinimidyl ester, Alexa Fluor® 488 alkyne, Alexa Fluor® 555 alkyne, triethylammonium salt, Alexa Fluor® 594 carboxamido-(5-(and 6-)propargyl), bis(triethylammonium salt, 3-propargyloxypropanoic acid, succinimidyl ester, biotin alkyne, tetraacetyl fucose alkyne, Oregon Green® 488 alkyne *6-isomer*, iodoacetamide alkyne, or 5-carboxytetramethylrhodamine propargylamide.

In some cases, the azide derivative attached to a solid support, SNAP, or biomolecule may be, for example, (S)-5-Azido-2-(Fmoc-amino)pentanoic acid, (S)-(–)-2-Azido-6-(Boc-amino)hexanoic acid (dicyclohexylammonium), (S)-2-Azido-3-(4-tert-butoxyphenyl)propionic acid cyclohexylammonium salt, L-Azidohomoalanine hydrochloride, (S)-2 Azido-3-(3-indolyl)propionic acid cyclohexylammonium salt, (S)-2-Azido-3-methylbutyric acid cyclohexylammonium salt, (S)-2-Azido-3-phenylpropionic acid (dicyclohexylammonium) salt, Boc-3-azido-Ala-OH (dicyclohexylammonium) salt, N-Boc-4-azido-L-homoalanine (dicyclohexylammonium) salt, N-Boc-6-azido-L-norleucine (dicyclohexylammonium) salt, Boc-4-azido-Phe-OH, (S)-(–)-4-tert-Butyl hydrogen 2-azidosuccinate (dicyclohexylammonium) salt, N2-[(1,1-Dimethylethoxy) carbonyl]-N6-[(2-propynyloxy)carbonyl]-L-lysine, Fmoc-β-azido-Ala-OH, 2-Acetamido-2-deoxy-β-D-glucopyranosyl azide, 2-Acetamido-2-deoxy-β-D-glucopyranosyl azide 3,4,6-triacetate, 2-Acetamido-3,4,6-tri-O-benzyl-2-deoxy-β-D-glucopyranosyl azide, N-Azidoacetylgalactosamine-tetraacylated, N-Azidoacetylglucosamine, N-Azidoacetyl-glucosamine-tetraacylated, 6-Azido-6-deoxy-1,2:3,4-di-O-isopropylidene-α-D-galactopyranose, 1-Azido-1-deoxy-β-D-galactopyranoside, 1-Azido-1-deoxy-β-D-galactopyranoside tetraacetate, 6-Azido-6-deoxy-D-galactose, 1-Azido-1-deoxy-β-D-glucopyranoside, 2-Azido-2-deoxy-D-glucose, 6-Azido-6-deoxy-D-glucose, 1-Azido-1-deoxy-β-D-lactopyranoside, 3-Azido-2,3-dideoxy-1-O-(tert-butyldimethylsilyl)-β-D-arabino-hexopyranose, 2-Azido-D-galactose tetraacetate, 1,2-Di-O-acetyl-3-azido-3-deoxy-5-O-(p-toluoyl)-D-ribofuranose, α-D-Mannopyranosyl azide tetraacetate, 2,3,4,6-Tetra-O-acetyl-1-azido-1-deoxy-α-D-galactopyranosyl cyanide, 2,3,4-Tri-O-acetyl-β-D-xylopyranosyl azide, 3'-Azido-3'-deoxythymidine, γ-(2-Azidoethyl)-ATP sodium salt solution, γ-[(6-Azidohexyl)-imido]-ATP sodium salt, (2'S)-2'-Deoxy-2'-fluoro-5-ethynyluridine, 5-Ethynyl-2'-deoxycytidine, N6-Propargyl-ATP sodium salt, 4-Acetamidobenzenesulfonyl azide, (E)-N-(2-Aminoethyl)-4-{2-[4-(3-azidopropoxy)phenyl] diazenyl}benzamide hydrochloride, Azidoacetic acid NHS ester, 1-Azidoadamantane, 4-Azidoaniline hydrochloride, (4S)-4-[(1R)-2-Azido-1-(benzyloxy)ethyl]-2,2-dimethyl-1, 3-dioxolane, NHS-PEG$_4$-azide, [3aS-(3aα,4α,5β,7aα)]-5-Azido-7-bromo-3a,4,5,7a-tetrahydro-2,2-dimethyl-1,3-benzodioxol-4-ol, 3'-Azido-3'-2-azido-1-methylquinolinium tetrafluoroborate, 5-Azidopentanoic acid, 4-Azidophenacyl bromide, 4-Azidophenyl isothiocyanate, 3-(4-Azidophenyl) propionic acid, 3-Azido-1-propanamine, 3-Azido-1-propanol, Azo biotin-azide, Biotin picolyl azide, tert-Butyl 2-(4-{[4-(3-azidopropoxy)phenyl]azo}benzamido) ethylcarbamate, 4-Carboxybenzenesulfonazide, 7-(Diethylamino)coumarin-3-carbonyl azide, Ethidium bromide monoazide, Ethyl azidoacetate, 4-Methoxybenzyloxycarbonyl azide, aryl azides, diazierines, or O-(2-Aminoethyl)-O'-(2-azidoethyl)heptaethylene glycol, bromoacetomido-PEG$_3$-azide, iodoacetamide-azide, Alexa Fluor® 488 azide, Alexa Fluor® 488 5-carboxamido-(6-azidohexanyl), bis(triethylammonium salt), Alexa Fluor® 555 azide triethylammonium salt, Alexa Fluor® 594 carboxamido-(6-azidohexanyl), bis(triethylammonium salt), Alexa Fluor® 647 azide triethylammonium salt, 3-(azido-tetra(ethyleneoxy))propionic acid succinimidyl ester, biotin azide, L-azidohomoalanine, L-homopropargylglycine, Click-iT® farnesyl alcohol azide, 15-azidopentadecanoic acid, 12-azidododecanoic acid, tetraacetylated N-azidoacetylgalactosamine, tetraacetylated N-azidoacetyl-D-mannosamine, tetraacetylated N-azidoacetylglucosamine, iodoacetamide azide, or tetramethylrhodamine 5-carboxamido-(6-azidohexanyl).

In some cases, the SNAPs may be covalently attached to the solid support using an inherent chemistry of the SNAP. In some cases, the solid support may be covered with functional groups that may be reactive to the SNAP. These functional groups, for example, may be hydroxyl, carbonyl, carboxyl, amino, amides, azides, alkynes, alkenes, phosphates, sulfhydryl, thiols, isothiocyanates, isocyanates, acyl azides, NHS esters, silane, sulfonyl chlorides, aldehydes, esters, glyoxals, epoxides, oxiranes, alkanethiols, carbonates, aryl halides, imidoesters, carbodiimides, anhydrides, fluorophenyl esters, amines, thymines or a combination thereof. In some cases, the SNAP may have a functional group that may react with a functional group on the solid support to form a covalent bond. For example, a DNA SNAP may be attached to a solid support by reacting one or more thymines in the DNA with amines on the solid support. For example, the —NH$_2$ at the N-terminus of a polypeptide chain or —COOH at the C-terminus of a polypeptide chain may react with an appropriate functional group and be attached to the solid support through a covalent bond. In some cases, for example, the functional group of a SNAP may be hydroxyl, carbonyl, carboxyl, amino, amides, azides, alkynes, silane, alkenes, phosphates, sulfhydryl, thiols, isothiocyanates, isocyanates, acyl azides, NHS esters, sulfonyl chlorides, aldehydes, esters, glyoxals, epoxides, oxiranes, alkanethiols, carbonates, aryl halides, imidoesters, carbodiimides, anhydrides, fluorophenyl esters, amines, thymines or a combination thereof. Other bioconjugation processes, reactions, and functional groups are described elsewhere within that may be used to attach a SNAP to a solid support.

Such a reaction could be spontaneous, or could be induced by application of heat or ultraviolet radiation.

In some cases, silane chemistry may be employed for bioconjugation. In some cases, functional silane compounds containing an organofunctional or organo-reactive arm can be used to conjugate biomolecules to inorganic substrates. The appropriate selection of the functional or reactive group for a particular application can allow the attachment of proteins, oligonucleotides, whole cells, organelles, or even tissue sections to substrates. The organosilanes used for these applications may include functional or reactive groups such as hydroxyl, amino, aldehyde, epoxy, carboxylate, thiol, and even alkyl groups to bind molecules through hydrophobic interactions. In some cases, 3-Aminopropyltriethoxysilane (APTS) and 3-Aminopropyltrimethoxysilane are used to create a functional group on an inorganic surface or particle. In some cases, once deposited on a substrate, the alkoxy groups form a covalent polymer coating with the primary amine groups sticking off the surface and available for subsequent conjugation. Carboxyl- or aldehyde-containing ligands may be directly coupled to the aminopropyl groups using a carbodiimide reaction or reductive amination. In some cases, alternatively, surfaces initially derivatized with an aminopropylsilane compound can be modified further with spacer arms or crosslinkers to create reactive groups for coupling affinity ligands or biomolecules. For instance, the amine groups may be derivatized with an NHS-PEGn-azide compound for use in click chemistry or Staudinger ligation reactions for linking proteins or other biomolecules. In some cases, APTS-modified surfaces may be further derivatized with amine-reactive crosslinkers to create additional surface characteristics and reactivity. Modification with NHS-PEG4-azide forms a hydrophilic PEG spacer terminating in an azido group that can be used in a click chemistry or Staudinger ligation reaction to couple other molecules.

In some cases, other crosslinking agents that contain an amine-reactive group on one end also may be used to modify and activate the APTS-modified substrate. Surfaces may be designed to contain, for instance, reactive hydrazine or aminooxy groups for conjugation with carbonyl-containing molecules, such as aldehydes formed through periodate oxidation of carbohydrates or natively present at the reducing end of sugars and glycans.

In some cases, the amine groups on ATPS surfaces may be acylated using glutaric anhydride to create carboxylate functionalities, which were then activated with NHS/DCC to form the NHS ester. This derivative could be used to couple amine-containing proteins and other molecules via amide bond formation. In a second activation strategy, the aminopropyl groups on the surface were activated with 1,4-phenylenediisothiocyanate (PDITC) to create terminal isothiocyanate groups for coupling amines. Both methods resulted in the successful coupling of amine-dendrimers to silica surfaces for use in arrays. In some cases, amine surfaces prepared using an aminosilane compound can be modified to contain carboxylate groups using the following protocol involving the reaction with an anhydride, such as succinic anhydride or glutaric anhydride. After modification, the carboxylates then can be used to couple amine-containing molecules using a carbodiimide reaction with EDC plus sulfo-NHS. In some cases, modification of an APTS surface with glutaric anhydride creates terminal carboxylates for coupling of amine-containing ligands which may be used for bioconjugation.

In some cases, aminosilane surfaces also may be activated by use of a bifunctional crosslinker to contain reactive groups for subsequent coupling to biomolecules. In one such reaction, N,N'-disuccinimidyl carbonate (DSC) was used to react with the amines on a slide surface and create terminal NHS-carbonate groups, which then could be coupled to amine-containing molecules, which may be used for bioconjugation. In some cases, APTS-modified surfaces can be activated with DSC to form amine-reactive succinimidyl carbonates for coupling proteins or other amine-containing molecules.

In some cases, silane coupling agents containing carboxylate groups may be used to functionalize a surface with carboxylic acids for subsequent conjugation with amine-containing molecules. For example, carboxyethylsilanetriol contains an acetate organo group on a silanetriol inorganic reactive end. The silanetriol component is reactive immediately with inorganic —OH substrates without prior hydrolysis of alkoxy groups, as in the case with most other silanization reagents. In some cases, carboxyethylsilanetriol has been used to add carboxylate groups to fluorescent silica nanoparticles to couple antibodies for multiplexed bacteria monitoring. This reagent can be used in similar fashion to add carboxylate functionality to many inorganic or metallic nano-materials, which also will create negative charge repulsion to maintain particle dispersion in aqueous solutions. In some cases, covalent coupling to the carboxylated surface then can be done by activation of the carboxylic acid groups with a carbodiimide to facilitate direct reaction with amine-containing molecules or to form intermediate NHS esters, which may be used for bioconjugation. In some cases, carboxylethylsilanetriol can be used to modify an inorganic substrate to containing carboxylate groups for coupling amine-containing ligands.

In some cases, silane modification agents such as glycidoxy may be utilized for bioconjugation to a surface substrate. Glycidoxy compounds contain reactive epoxy groups. Surfaces covalently coated with these silane coupling agents can be used to conjugate thiol-, amine-, or hydroxyl-containing ligands, depending on the pH of the reaction. In some cases, 3-glycidoxy-propyltrimethoxysilane (GOPTS) or 3-glycidoxypro-pyltriethoxysilane can be used to link inorganic silica or other metallic surfaces containing —OH groups with biological molecules containing any three of these major functional groups. In some cases, epoxy-containing silane coupling agents form reactive surfaces that can be used to couple amine-, thiol-, or hydroxyl-containing ligands which may be used for bioconjugation.

In some cases, the reaction of the epoxide with a thiol group yields a thioether linkage, whereas reaction with a hydroxyl gives an ether and reaction with an amine results in a secondary amine bond. The relative reactivity of an epoxy group is thiol>amine>hydroxyl, and this is reflected by the optimal pH range for each reaction. In this case, the lower the reactivity of the functional group the higher the pH required to drive the reaction efficiently.

In some cases, isocyanates groups may be utilized for bioconjugation to a surface support. Isocyanate groups are extremely reactive toward nucleophiles and will hydrolyze rapidly in aqueous solution which are especially useful for covalent coupling to hydroxyl groups under nonaqueous conditions, which is appropriate for conjugation to many carbohydrate ligands. Silanization can be accomplished in dry organic solvent to form reactive surfaces while preserving the activity of the isocyanates. Isocyanatopropyltriethoxysilane (ICPTES) contains an isocyanate group at the end of a short propyl spacer, which is connected to the triethoxysilane group useful for attachment to inorganic substrates. In some cases, the isocyanate-containing silane coupling agent can be used to couple hydroxyl-containing molecules to inorganic surfaces which may be used for bioconjugation.

In some cases, ICPTES may be used to create novel chitosan-siloxane hybrid polymers by coupling the isocyanate groups to the functional groups of the carbohydrate and forming a silica polymer using the triethoxysilane backbone. In some cases, ICPTES and APTS have been used in combination to create organically modified silica xerogels through carboxylic acid solvolysis that formed hybrid materials with luminescent properties.

In some cases, nanoparticles or microparticles may be utilized as a surface support for bioconjugation. In some cases, particle types and compositions of almost limitless shape and size, including spherical, amorphous, or aggregate particles, as well as elaborate geometric shapes like rods, tubes, cubes, triangles, and cones. In addition, new symmetrical organic constructs have emerged in the nanometer range that include fullerenes (e.g., Bucky-balls), carbon nanotubes, and dendrimers, which are highly defined synthetic structures used as bioconjugation scaffolds. The chemical composition of particles may be just as varied as their shape. Particles can comprise of polymers or copolymers, inorganic constructs, metals, semiconductors, superparamagnetic composites, biodegradable constructs, synthetic dendrimers, and dendrons. Polymeric particles can be constructed from a number of different monomers or copolymer combinations. Some of the more common ones include polystyrene (traditional "latex" particles), poly(styrene/divinylbenzene) copolymers, poly(styrene/acrylate) copolymers, polymethylmethacrylate (PMMA), poly (hydroxyethyl methacrylate) (pHEMA), poly (vinyltoluene), poly(styrene/butadiene) copolymers, and poly(styrene/vinyltoluene) copolymers. In some cases, by mixing into the polymerization reaction combinations of functional monomers, one can create reactive or functional groups on the particle surface for subsequent coupling to affinity ligands. One example of this is a poly(styrene/acrylate) copolymer particle, which creates carboxylate groups within the polymer structure, the number of which is dependent on the ratio of monomers used in the polymerization process. In some cases, inorganic particles are used extensively in various bioapplications. For example, gold nanoparticles may be used for detection labels for immunohistochemical (IHC) staining and lateral flow diagnostic testing. In some cases, the use of particles in bioapplications like bioconjugation involves the attachment of affinity capture ligands to their surface, by either passive adsorption or covalent coupling. The coupling of an affinity ligand to such particles creates the ability to bind selectively biological targets in complex sample mixtures. The affinity particle complexes can thus be used to separate and isolate proteins or other biomolecules or to specifically detect the presence of these targets in cells, tissue sections, lysates, or other complex biological samples. In some cases, the reactions used for coupling affinity ligands to nanoparticles or microparticles are basically the same as those used for bioconjugation of molecules described herein.

In some cases, particle type used for bioapplications (e.g. bioconjugation) is the polymeric microsphere or nanosphere, which comprises a spherical, nonporous, "hard" particle made up of long, entwined linear or crosslinked polymers. In some cases, creation of these particles involves an emulsion polymerization process that uses vinyl monomers, sometimes in the presence of divinyl crosslinking monomers. In some cases, larger microparticles may be built from successive polymerization steps through growth of much smaller nanoparticle seeds. In some cases, polymeric particles comprise of polystyrene or copolymers of styrene, like styrene/divinylbenzene, styrene/butadiene, sty-rene/acrylate, or styrene/vinyltoluene. Other common polymer supports include polymethylmethacrylate (PMMA), polyvinyltoluene, poly(hydroxyethyl meth-acrylate) (pHEMA), and the copolymer poly(ethylene glycol dimethacrylate/2-hydroxyethylmetacrylate) [poly(EGDMA/HEMA)].

In some cases, one method of attaching biomolecules to hydrophobic polymeric particles is the use of passive adsorption. In some cases, protein adsorption onto hydrophobic particles takes place through strong interactions of nonpolar or aromatic amino acid residues with the surface polymer chains on the particles with concomitant exclusion of water molecules. Since proteins usually contain hydrophobic core structures with predominately hydrophilic surfaces, their interaction with hydrophobic particles must involve significant conformational changes to create large-scale hydrophobic contacts.

In some cases, particle types contain functional groups that are built into the polymer backbone and displayed on their surface. The quantity of these groups can vary widely depending on the type and ratios of monomers used in the polymerization process or the degree of secondary surface modifications that have been performed. In some cases, functionalized particles can be used to couple covalently biomolecules through the appropriate reaction conditions.

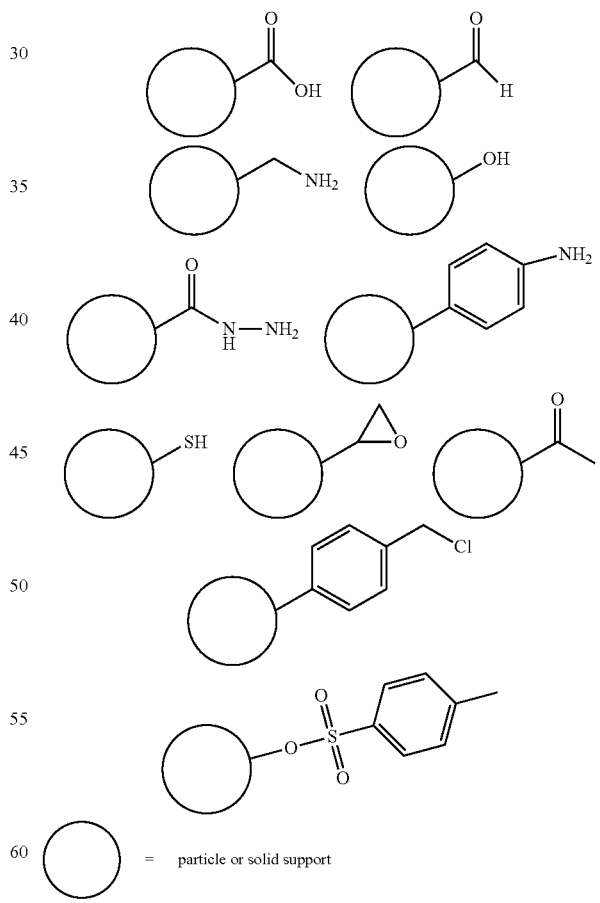

Common Functional Groups or Reactive Groups on Particles for Bioconjugation

In some cases, a particle may couple with a crosslinker for bioconjugation.

In some cases, the rate of attachment of DNA SNAPs s to the solid support, or the efficacy or strength of attachment, may be altered by altering the sequence of DNA comprising the SNAP. For example, in the case of a DNA SNAP attached to a solid support by a reaction involving one or more thymines the attachment may be varied by varying the number of thymines in the DNA sequence. In some cases, increasing the number of thymines may facilitate the attachment of the SNAP to the solid support.

In some cases, the solid support is a part of a flow cell. In some cases, the SNAPs may be attached to a solid support in a flow cell. In some cases, the SNAPs may be directly conjugated to a solid support in a flow cell. In some cases, the SNAPs may be adsorbed to a solid support in a flow cell. Attaching the SNAPs in the flow cell may allow visualization of the SNAPs as they attach to the solid support. The attachment of the SNAPs may be optimized by monitoring the number of attached SNAPs compared to the number of attachment sites during the attachment process. In some cases, the attachment of the SNAPs may be optimized by monitoring the area of the solid support covered by the SNAPs and the area of the solid support that is unoccupied by the SNAPs during the attachment process.

In some cases, the SNAPs may be conjugated directly in a flow cell. In some cases, the SNAPs may be conjugated to a surface within the flow cell. In some cases, the SNAPs may be conjugated to a surface within the flow cell before being conjugated to the biological or chemical entities. In some cases, a biological or chemical entity may be flowed into a flow cell and conjugated to a SNAP that is already conjugated to the solid support. In some cases, a biological or chemical entity may be conjugated to a SNAP before the SNAP is introduced into a flow cell and conjugated to a solid support in a flow cell. In some cases, a biological or chemical entity and a SNAP may be introduced into a flow cell and conjugated to each other within the flow cell, before the SNAP is conjugated to a solid support within the flow cell.

In some cases, the biological or chemical entities may be conjugated to the SNAPs prior to attaching the SNAPs to a solid support. After performing such a reaction the products may be purified to separate out conjugated SNAP-biological/chemical entity moieties from unconjugated SNAPs and biological/chemical entities.

The methods of this disclosure may be used to spatially separate biological or chemical entities. In some embodiments, methods of this disclosure may be used to spatially separate proteins, small molecules, DNAs, RNAs, glycoproteins, metabolites, carbohydrates, enzymes, or antibodies. In some embodiments, methods of this disclosure may be used to spatially separate complexes, such as protein complexes comprising two or more proteins, protein nucleic acid complexes, or other complexes. In some cases, the methods may be used to spatially separate viral particles or viroids. In some cases, the methods may be used to separate cells, such as bacterial cells, microbial cells, mammalian cells or other cells.

In some embodiments, the SNAP may be formed on the seed prior to the seed being attached to the biological or chemical entity.

In some embodiments this disclosure provides a composition comprising a nucleic acid SNAP attached to a protein, a nucleic acid SNAP attached to a small molecule, a nucleic acid SNAP attached to a protein complex, a nucleic acid SNAP attached to a protein nucleic acid SNAP, a nucleic acid SNAP attached to a carbohydrate, a nucleic acid SNAP attached to a viral particle or a nucleic acid SNAP attached to a cell.

In some embodiments this disclosure provides a composition comprising a dendrimer attached to a protein, a dendrimer attached to a small molecule, a dendrimer attached to a protein complex, a dendrimer attached to a protein dendrimer, a dendrimer attached to a carbohydrate, a dendrimer attached to a viral particle or a dendrimer attached to a cell.

In some cases, the biological or chemical entities may be eluted from the solid support either by cleaving a photocleavable bond, or by chemically or enzymatically digesting the SNAP.

In some cases, the biological or chemical entities may attach to the solid support directly, while the SNAPs occlude other biological or chemical entities from attaching in the immediate vicinity. In some cases the biological or chemical entities may attach directly to an attachment site within a microwell or nanowell, and the size of the SNAPs may be selected to prevent more than one SNAP from occupying the microwell or nanowell. In such cases, the SNAP may be removed, either by cleaving a photo-cleavable bond, or by chemically or enzymatically digesting the SNAP.

In some embodiments, SNAPs of this disclosure may be used as nanoparticles. For example, SNAPs of this disclosure may be used as nanoparticles for detection or visualization. In some cases, a nucleic acid SNAP may be formed which incorporates modified nucleotides which comprise fluorescent moieties. Any fluorescently labeled nucleotide known in the art may be used in a SNAP of this disclosure. Examples of fluorescently labeled nucleotides include, but are not limited to, Alexa Fluor™ 555-aha-dCTP, Alexa Fluor™ 555-aha-dUTP, 1 mM in TE buffer, Alexa Fluor™ 647 ATP (Adenosine 5'-Triphosphate, Alexa Fluor™ 647 2'-(or-3)-O—(N-(2-Aminoethyl) Urethane), Hexa(Triethylammonium) Salt), Alexa Fluor™ 647-aha-dCTP, Alexa Fluor™ 647-aha-dUTP, 1 mM in TE buffer, BODIPY™ FL ATP (Adenosine 5'-Triphosphate, BODIPY™ FL 2'-(or-3')-O—(N-(2-Aminoethyl)Urethane), Trisodium Salt), 5 mM in buffer, BODIPY™ FL ATP-γ-S, Thioester (Adenosine 5'-O-(3-Thiotriphosphate), BODIPY™ FL Thioester, Sodium Salt), BODIPY™ FL GDP (Guanosine 5'-Diphosphate, BODIPY™ FL 2'-(or-3)-O—(N-(2-Aminoethyl) Urethane), Bis (Triethylammonium) Salt), ChromaTide™ Alexa Fluor™ 488-5-UTP, ChromaTide™ Alexa Fluor™ 488-5-dUTP, ChromaTide™ Alexa Fluor™ 546-14-UTP, ChromaTide™ Alexa Fluor™ 546-14-dUTP, ChromaTide™ Alexa Fluor™ 568-5-dUTP, ChromaTide™ Alexa Fluor™ 594-5-dUTP, ChromaTide™ Fluorescein-12-dUTP, ChromaTide™ Texas Red™-12-dUTP, Fluorescein-12-dUTP Solution (1 mM), Fluorescein-aha-dUTP—1 mM in TE Buffer, Guanosine 5'-O-(3-Thiotriphosphate), BODIPY™ FL Thioester, Sodium Salt (BODIPY™ FL GTP-γ-S, Thioester), Guanosine 5'-Triphosphate, BODIPY™ FL 2'-(or-3)-O—(N-(2-Aminoethyl) Urethane), Trisodium Salt (BODIPY™ FL GTP), Guanosine 5'-Triphosphate, BODIPY™ TR 2'-(or-3')-O—(N-(2-Aminoethyl) Urethane), Trisodium Salt (BODIPY™ TR GTP), MANT-ADP (2'-(or-3)-O—(N-Methylanthraniloyl) Adenosine 5'-Diphosphate, Disodium Salt), MANT-ATP (2'-(or-3')-O—(N-Methylanthraniloyl) Adenosine 5'-Triphosphate, Trisodium Salt), MANT-GDP (2'-(or-3)-O—(N-Methylanthraniloyl) Guanosine 5'-Diphosphate, Disodium Salt), MANT-GMPPNP (2'-(or-3)-O—(N-Methylanthraniloyl)-β:γ-Imidoguanosine 5'-Triphosphate, and Trisodium Salt), MANT-GTP (2'-(or-3)-O—(N-Methylanthraniloyl) Guanosine 5'-Triphosphate, Trisodium Salt).

In some cases, a SNAP of this disclosure may be designed such that probes may be attached onto the surface of the SNAP. A SNAP with attached probes may be used as a detection reagent. In some cases, a SNAP with attached probes is also labeled with fluorescent moieties to form a fluorescent detection reagent. In some cases, a SNAP with attached probes and fluorescent moieties may provide a high degree of signal amplification. The amount of probes on the SNAP may be titrated to achieve a desired degree of sample amplification. In some cases, differently sized SNAPs may be attached to different probes. In some cases, differently colored SNAPs may be attached to different probes. In some cases a library of different probes may be attached to fluorescently labeled SNAPs such that a first probe is attached to a SNAP which is a different size and/or color from a SNAP each other probe is attached to.

EXAMPLES

Example 1—Generation of DNA SNAPs

Oligos were reconstituted in dH20 to a final concentration of 100 uM with the exception of the extension primer which was reconstituted to 500 uM (2.9 mg/ml). The extension primer was conjugated to Deep Red 200 nm bead.

```
Primer 1 -
                                           (SEQ ID NO: 1)
5'-GCCAGGGTGCGAGGGTTTGTTTCATTGCTTCACGCCCTTACCCTCGC

ACCCTGGCACGG

Primer 2 -
                                           (SEQ ID NO: 2)
5'-TCCCACGGTGGCACCTCGCACCT Primer 3 -
                                           (SEQ ID NO: 3)
5'-CGCACGCTGCCACCCTCGCTTTTGCGAGGGTGGCAGCGT Primer 4 -
                                           (SEQ ID NO: 4)
5'-GCGAGGTGCGAGGTGCCACCGTGGGACCGT Extension Primer -
                                           (SEQ ID NO: 5)
5'-AAGGGCGTGAAGCAATGA
```

Amplification of Template
The following submixes were prepared:

| Submix 1: | |
| --- | --- |
| Water | 187.5 μL |
| 1M Tris-HCl pH 7.5 | 12.5 μL |
| Primer 1 [100 uM] | 50 μL |
| Submix 2: | |
| Water | 375 μL |
| 1M Tris-HCl pH 7.5 | 25 μL |
| Primer 2 [100 uM] | 50 μL |
| Primer 4 [100 uM] | 50 μL |
| Submix 3: | |
| Water | 187.5 μL |
| 1M Tris-HCl pH 7.5 | 12.5 μL |
| Primer 3 [100 uM] | 50 μL |

Each submix was aliquoted into 100 μL aliquots and incubated as described below:
Thermocycler conditions:
95° C. 30 seconds
Ramp down to 50° C. at 0.1° C./s
Hold at 4° C.
Ligation of the Rolling Circle Template

| Mix: | |
| --- | --- |
| Submix 1 | 100 μL |
| Submix 2 | 100 μL |
| Submix 3 | 100 μL |
| Ligation: | |
| 10X NEB T4 DNA ligase buffer | 200 μL |
| Mixed Oligo submix [5 uM] | 200 μL |
| Water | 1500 μL |
| Mix. | |

Add 100 μL NEB T4 DNA Ligase [400,000 u/ml]
Complete mixture was aliquoted into PCR tubes and incubated at 20° C. for ~20 hr followed by 65° C. for 10 minutes.
Solutions were pooled and 50 μL of 100 uM stock extension primers were added and mixed. Mixture was aliquoted into 100 μL aliquots in PCR tubes and subjected to the following temperature conditions:
Thermocycler conditions:
70° C. 30 seconds
Ramp down to 40° C. at 0.1° C./s
Hold at 4° C.
Template can now be stored at −20° C. until ready to use.
Rolling Circle Amplification for Nanoparticle Construction

| PCR Mix: | |
| --- | --- |
| Water | 969 μL |
| 10X NEB phi29 buffer | 150 μL |
| TCEP [500 mM] | 15 μL |
| BSA [100X] | 15 μL |
| dNTP mix [10 mM] | 1.5 μL |

Vortexed to mix then Added:

| Primed Rolling Circle Template | 300 μL |
| --- | --- |

Vortexed to mix then Added:

| NEB phi29 polymerase [10 Ku/ml] | 50 μL |
| --- | --- |

Figure 3A:
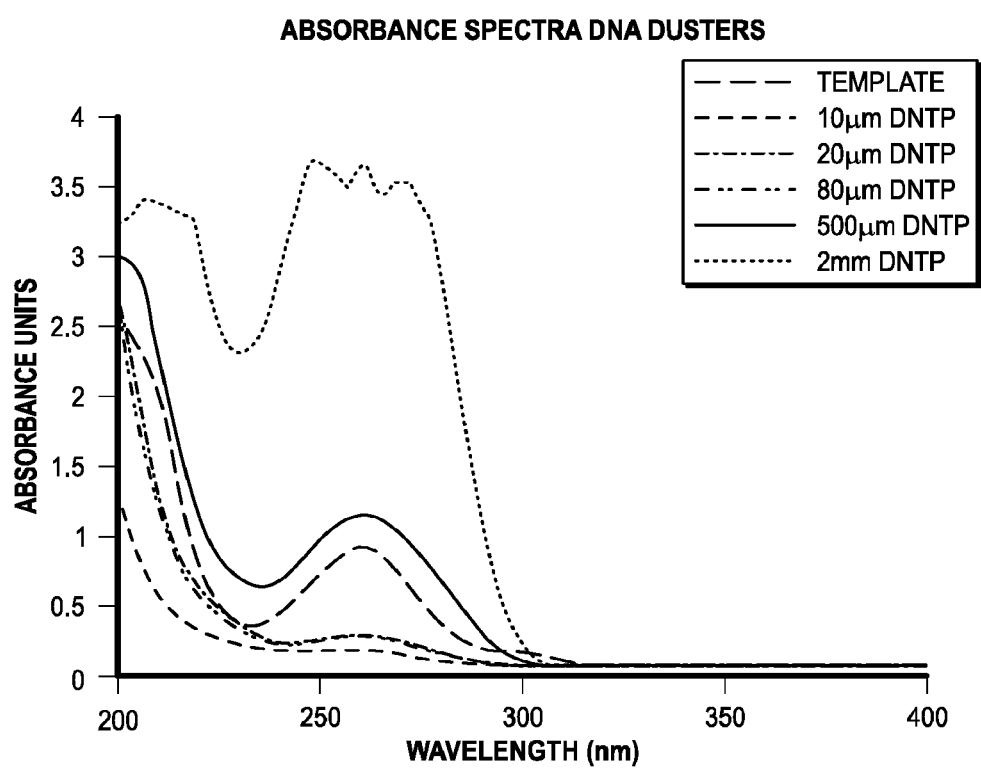
FIG. 3A illustrates absorbance spectra of SNAPs produced in Example 1.
Figure 3B:
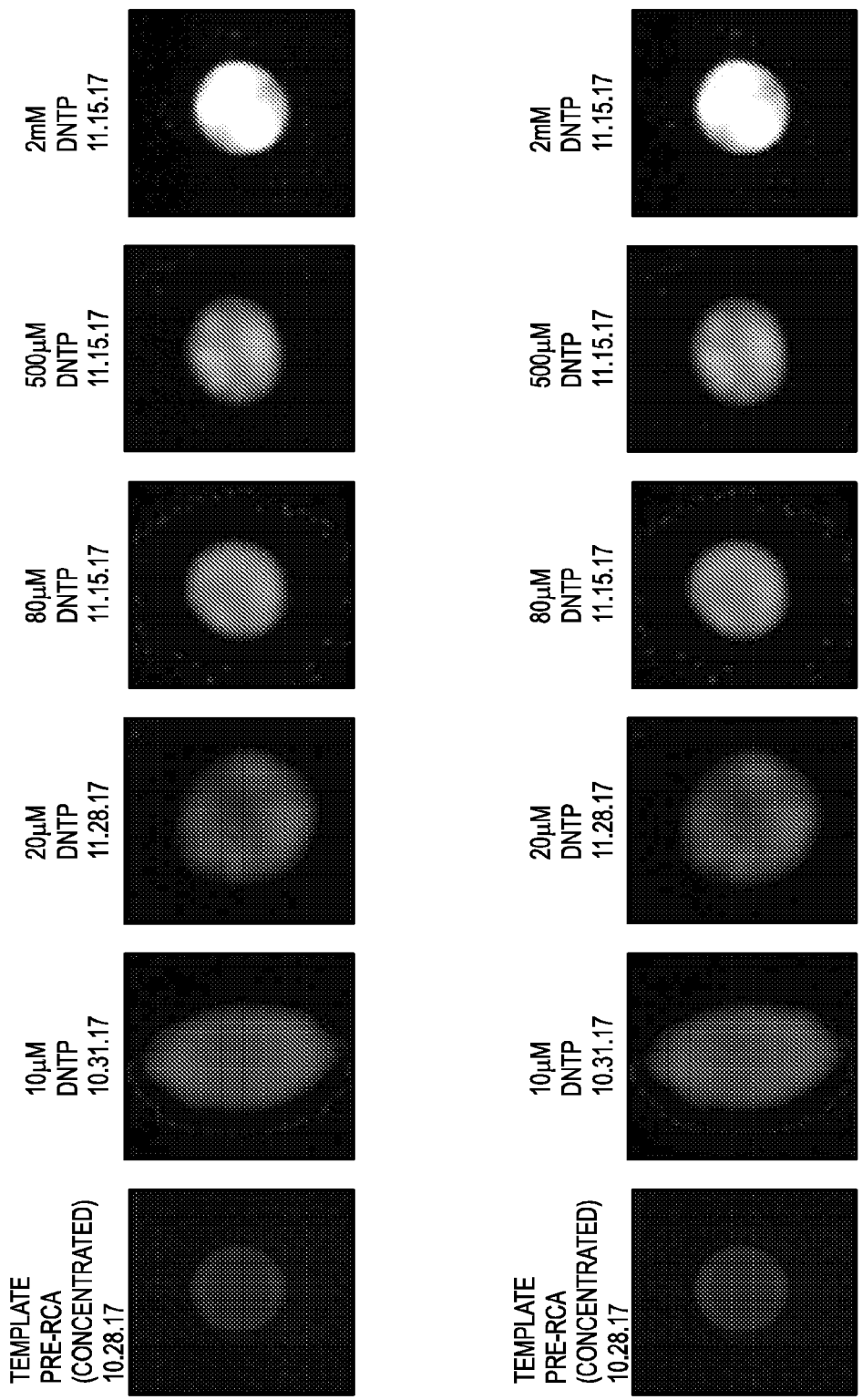
FIG. 3B illustrates fluorescence intensity of the SNAPs imaged as a dot blot.
Figure 4:
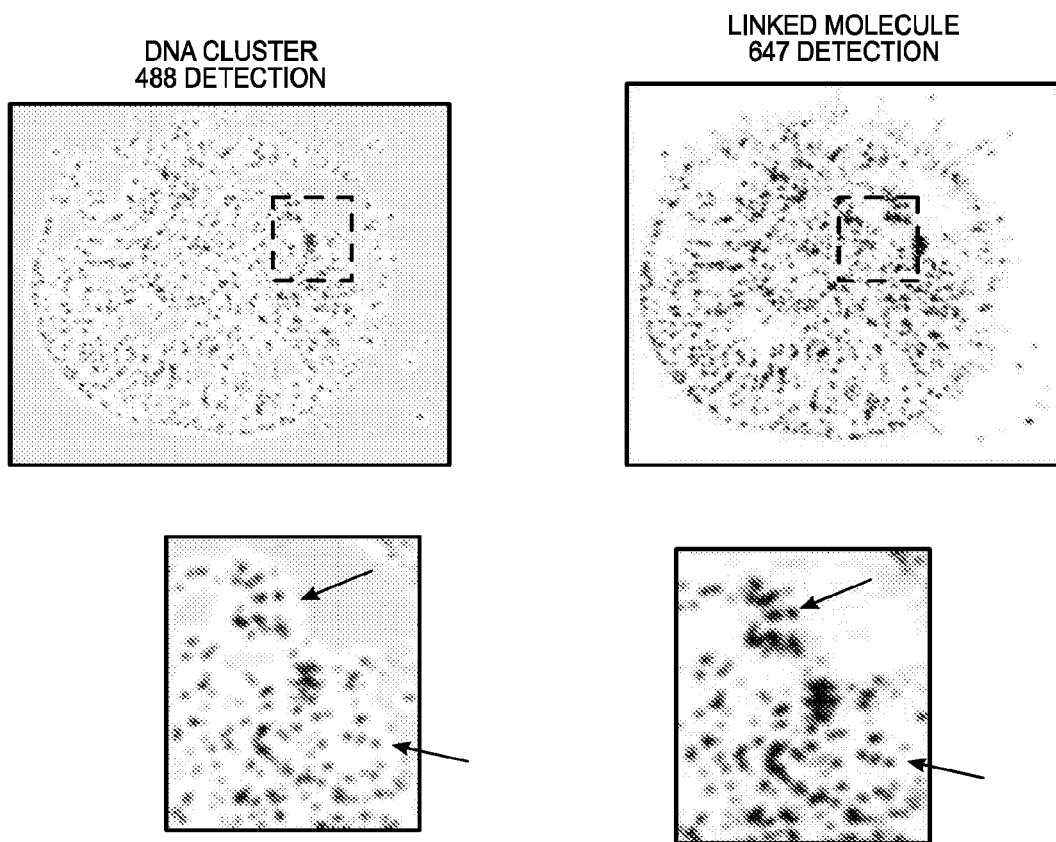
FIG. 4 illustrates co-localization of the SNAPs and attached Deep Red 200 nm beads in microscopy images of the SNAPs produced in Example 1. The Sybr Gold used to visualize the DNA fluoresces at 488 nm, and the linked Deep Red bead fluoresces at 647 nm, regions of the images are blown up to show details, and arrow heads point to examples of co-localization.

Inverted to mix. Aliquoted reaction mixture into 63 μt aliquots in PCR tubes.
Incubated at
30° C. for 120 minutes
65° C. for 10 minutes
Pooled samples and added 90 ul of 250 mM EDTA.
Centrifuged sample at 12,500 G for 5 minutes at 4° C.
Recovered supernatant and discarded white pellet.
Analysis of Nanoballs
Serial dilutions were performed 1:100 on sample (100 ul)+1:10 dilution and 2 ul of Sybr Gold (1×) was added. Applied 1 ul spots on amine surface treated slides and imaged. As seen in FIG. 3 and FIG. 4 DNA SNAPs were successfully formed, and a high degree of co-localization was seen between the DNA SNAPs and the Deep Red balls.

Analysis of Binding

In some cases, SNAPs can be removed from a surface they attach to, such as a chip or array. Removal of SNAPs can be mediated for example by a high amount of acetonitrile, a high concentration of sodium hydroxide, or a high concentration of salt. A high amount of acetonitrile can be a final percentage of at least about 20%, 30%, 40%, 50%, 60%, 70%, 80%, 90%, or 100% acetonitrile. A high amount of sodium hydroxide can be at least about 0.1 M, 0.5 M, 1 M, 2 M, 3 M, 4 M, 5 M, 6 M, 7 M, 8 M, 9 M, or 10 M. A high amount of salt can be at least about 0.1 M, 0.5 M, 1 M, 2 M, 3 M, 4 M, 5 M, 6 M, 7 M, 8 M, 9 M, or 10 M. The salt used can be for example $MgCl_2$ or NaCl. In some cases, a chaotropic reagent such as DMSO or formamide can mediate the removal of SNAPs.

Example 2—SNAP Production Using an Epimark Tao Polymerase

In a further example, SNAP production was optimized using an Epimark Taq polymerase. SNAP templates were prepared according to the method described in Example 1, paragraphs [0093]-[40098] The Taq polymerase was determined to have better control over SNAP size than phi29 polymerases. A 500 µl reaction mixture was prepared using an 8683 ng template. The following reagents were mixed in a 1.5 ml PCR tube:

| PCR Mix: | |
| --- | --- |
| 5X reaction buffer | 100 µl |
| 10 mM dNTPs | 10 µl |
| Template DNA | 16.3 µl |
| Fluorescent dNTPs | 5 µl |
| Nuclease-free water | 369 ul µl |
| Total volume | 500 µl |

The PCR mix was vortexed briefly in the PCR tube. After vortexing, 2.5 µl of Epimark Taq Polymerase was added to the PCR mix. The PCR tube was inverted to mix the polymerase with the other reagents. The PCR mix was placed in a thermal cycler. The template DNA was initially denatured at 94° C. for 30 seconds. The reaction mixture was amplified for 30 cycles under the following thermal conditions:

Denaturation at 94° C. for 30 seconds
Annealing at 53° C. for 60 seconds
Extension at 68° C. for 30 seconds After the final thermal cycle, the SNAPs were held at 68° C. for 5 further minutes. The PCR tube was then cooled to 4° C. and held until purification.

SNAPs were purified after synthesis. dNTPs were removed via an EDTA spin purification method. 30 µl of 250 mM EDTA was added to the 500 µl PCR mix in the PCR tube. The PCR tube was centrifuged at 12,500 G for 5 minutes at 4° C. The supernatant was saved and the pellet was discarded. SNAP samples were filtered with 0.22 µm filter tubes, then purified using AKTA FPLC using a gradient method. SNAPs were purified via anion exchange chromatography using 1 L each of deionized water and 1M NaCl solution that had been filtered through 0.22 µm filters. After collecting the SNAP-containing fraction, the solution was desalted using overnight dialysis in a dialysis cassette. SNAPs were concentrated using a vacuum centrifuge. The solvent was evaporated at 28° C. for approximately 4 hours until the final volume was less than 500 µl.

Example 3: Purification of SNAPs

A batch of SNAPs can be produced as described herein. Once the SNAPs are produced, they can be purified. A three step example protocol of how SNAPs can be purified is described below.

Step 1: Anion Exchange Chromatography

Fast protein liquid chromatography (FPLC) anion exchange chromatography was used to purify SNAPs. Here, a salt gradient was used to separate differentially charged DNA molecules (SNAPs) for collection. Three fractions (bottom, middle, top) were collected for analysis.

Figure 5:
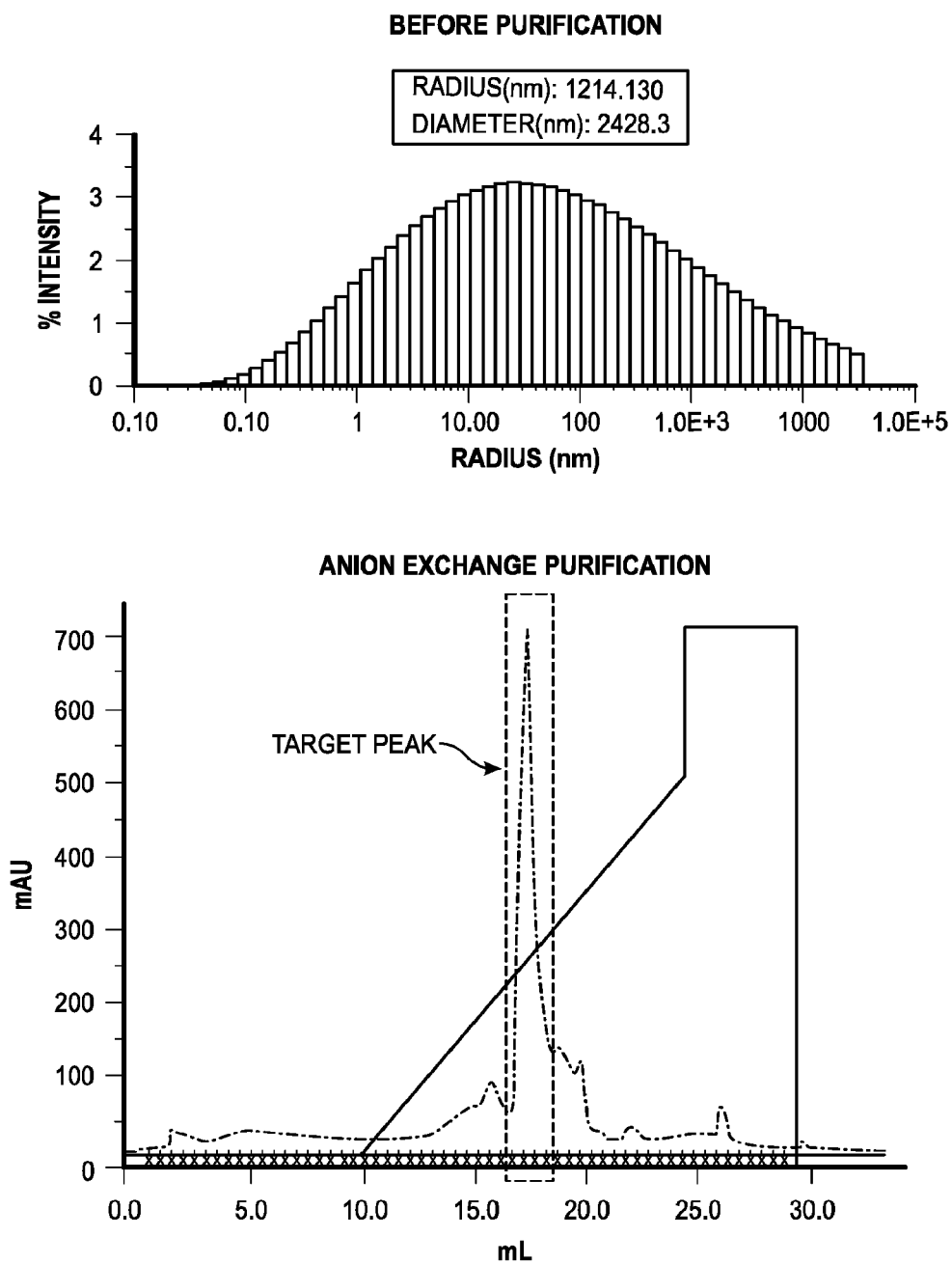
FIG. 5 illustrates the radii of particles in a sample comprising SNAPs before and after anion exchange purification.
Figure 5:
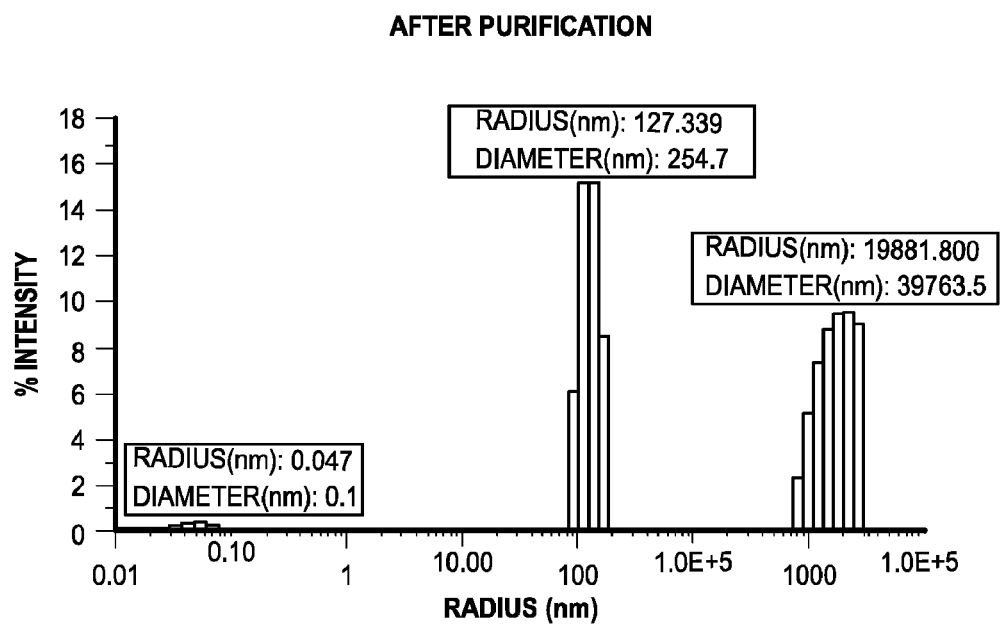

An example of the anion exchange purification is shown in FIG. 5. Dynamic light scattering was used to measure the hydrodynamic radius of particles in a sample prior to purification (left panel). The radii are distributed between about 0.1 nm and 10,000 nm. During anion exchange purification, samples present in an identified target peak (middle panel) were collected. Dynamic light scattering was used to measure the hydrodynamic radius of particles in the purified sample, and the samples were found to comprise SNAPs having hydrodynamic radii around about 100 nm and around about 1000 nm.

In some cases, size exclusion chromatography can be performed in lieu of anion exchange chromatography for purification.

Figure 6:
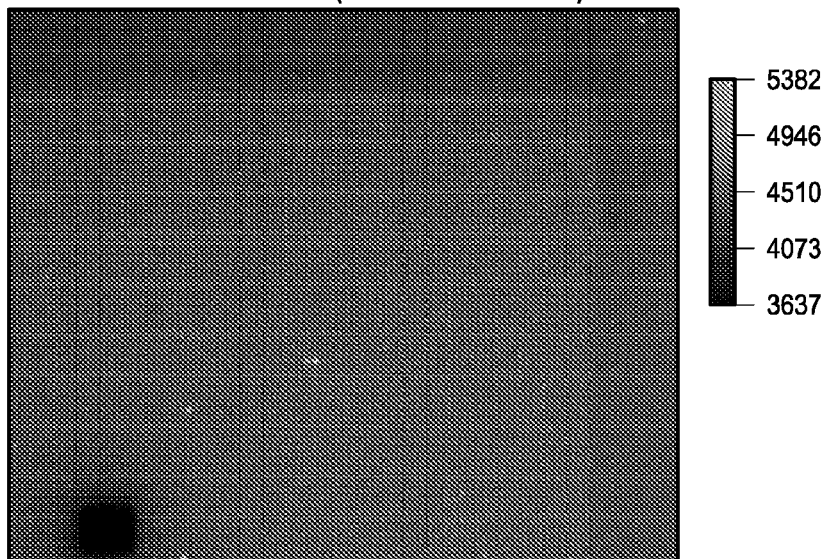
FIG. 6 illustrates the intensities detected in fractions collected during the anion exchange purification of samples comprising SNAPs.
Figure 6:
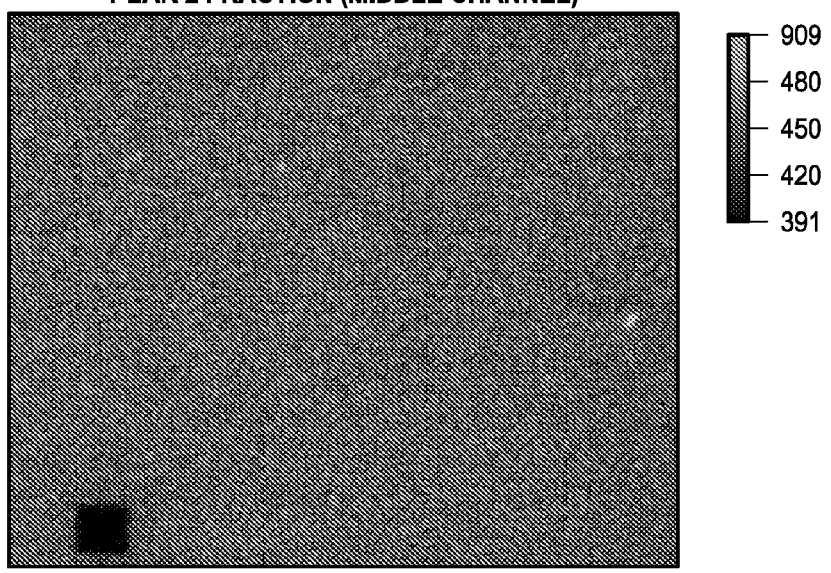
Figure 6:
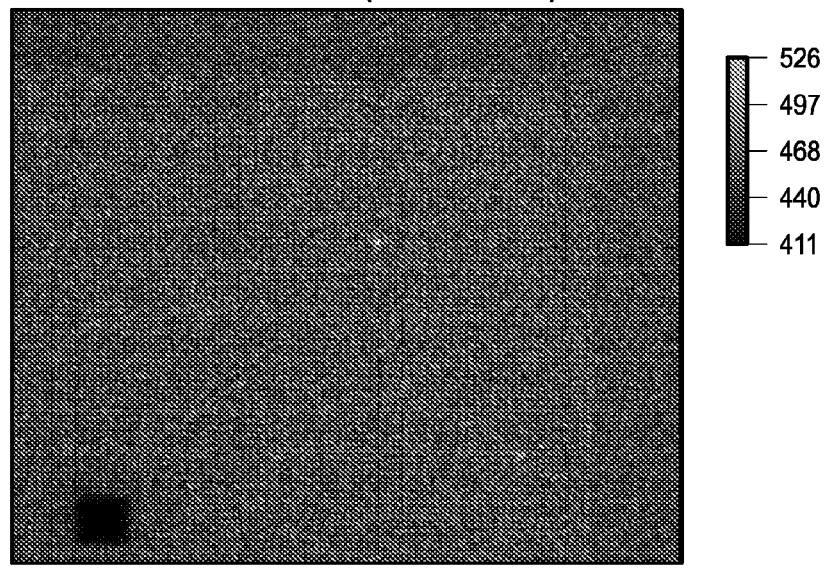
Figure 6:
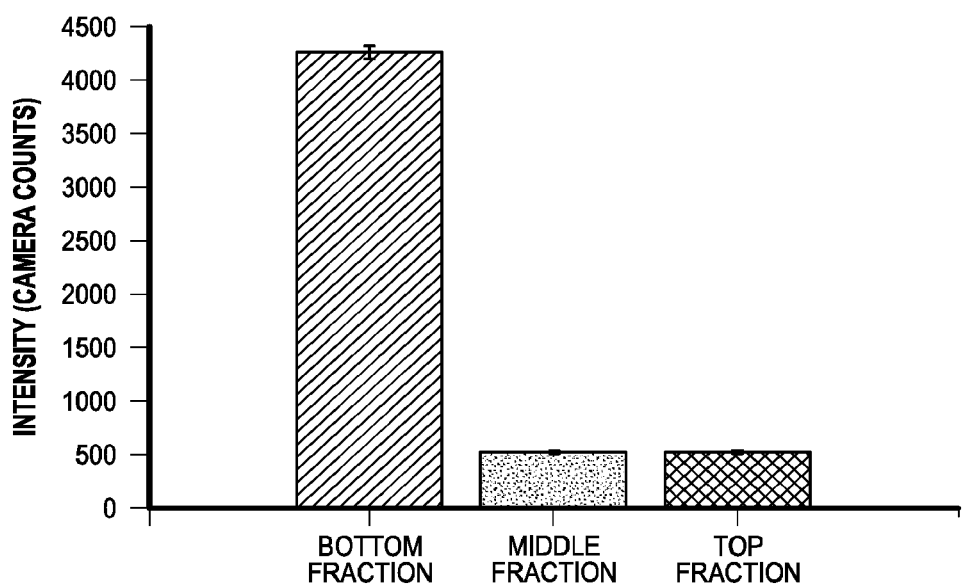

Samples from the three channels were imaged (FIG. 6, left) using a standard microscopy protocol, and intensities were quantified (right). SNAPs from the bottom channel displayed a higher intensity than those from the middle and top channels. Thus, in some cases, the size and/or brightness of the SNAPs can elute in a particular anion exchange fraction.

Step 2: Dialysis

After the anion exchange chromatography was performed, salt was removed by a standard dialysis protocol. Briefly, dialysis is a separation technique that can facilitate the removal of small, unwanted compounds (e.g. salt) from macromolecules (e.g. SNAPs) in solution by selective and passive diffusion through a semi-permeable membrane. An anion exchange purified sample comprising SNAPs requiring salt removal and a buffer solution were placed on opposite sides of the membrane. SNAPs were retained on the sample side of the membrane, but salt was able to pass freely through the membrane. The salt collected on the side of the membrane opposite the SNAPs, thus reducing the concentration of salt in the sample. In this way, the concentrations of small contaminants such as salt within the sample were decreased to acceptable or negligible levels.

Step 3: Concentration

Using a standard vacuum centrifugation protocol, batches of SNAPs were concentrated with minimal loss compared to conventional approaches.

SNAPs can be concentrated to a final concentration of between 1 µM and 100 µM. For example, batches of SNAPs produced have had concentrations of about 63.6 µM, 47.5 µM, 38 µM, and 8.9 µM.

Figure 7:
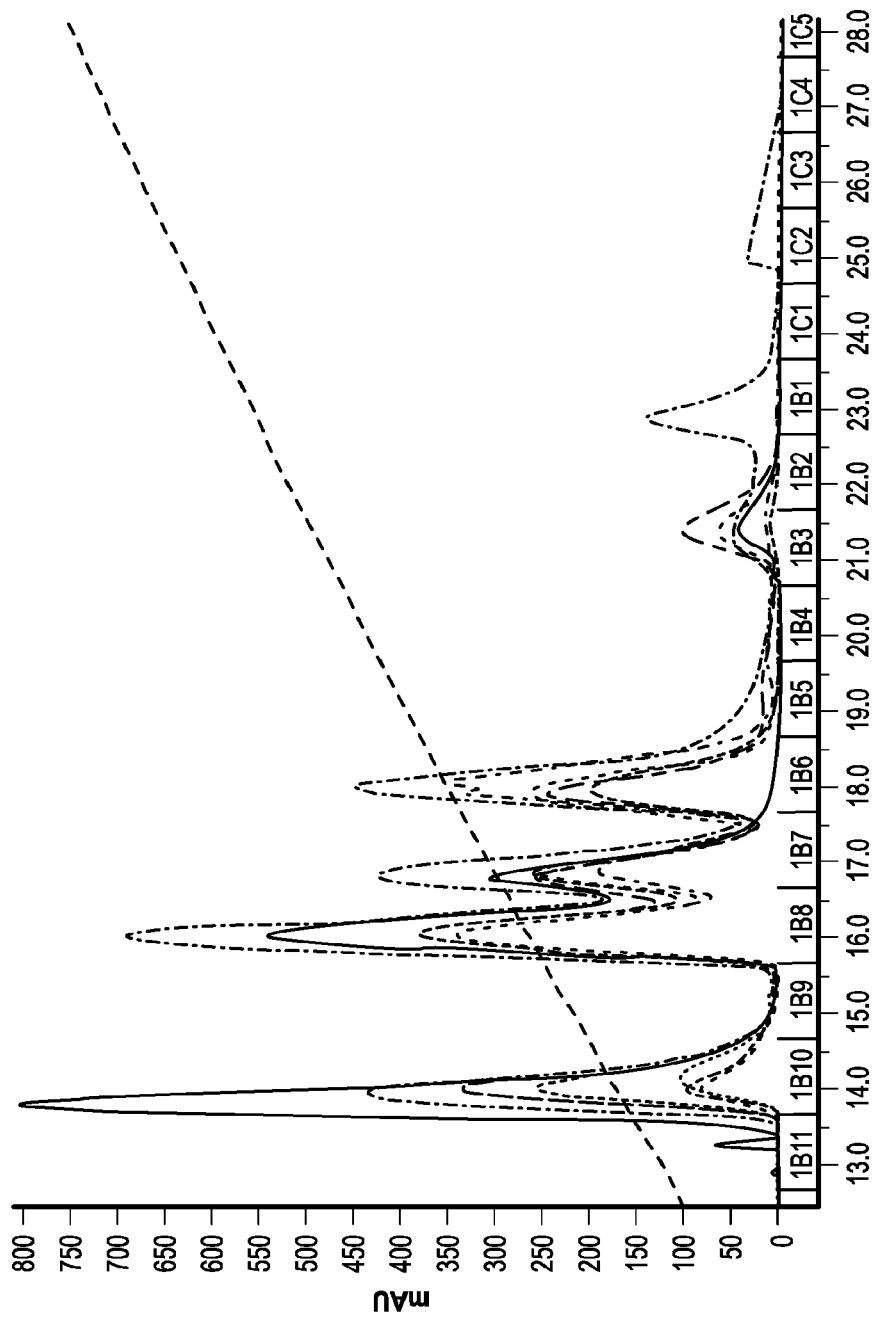
FIG. 7 illustrates the absorption spectra at 260 nm traces of different batches of SNAPs.

FIG. 7 shows the absorption spectra at 260 nm (A260) traces of different SNAP batches. The individual batches were produced using varying fluorescent dNTP types, fluorescent dNTPs from varying vendors, varying fluorescent dyes, varying Taq polymerases, and/or Taq polymerases used from varying vendors. Each SNAP displays a similar absorption profile.

Example 4: Production of SNAPs of a Desired Size

SNAPs were produced as described herein, and nanoparticle size was measured.

Methods for measuring nanoparticle (e.g. SNAP) size can include dynamic light scattering, nanoparticle tracking analysis, and microscopy techniques such as transmission electron microscopy (TEM), scanning electron microscopy (SEM), and atomic force microscopy (AFM).

Dynamic light scattering, which was used herein, can measure a diffusion coefficient through constructive and destructive interference patterns of an entire population of SNAPs. Nanoparticle tracking analysis can measure the diffusion coefficient through particle tracking of individual particles if the particles are greater than 30 nm in size. Microscopy techniques including TEM, SEM, and AFM can measure particle size and allow subsequent image analysis of individual particles without relying on the scattering of light.

Figure 8:
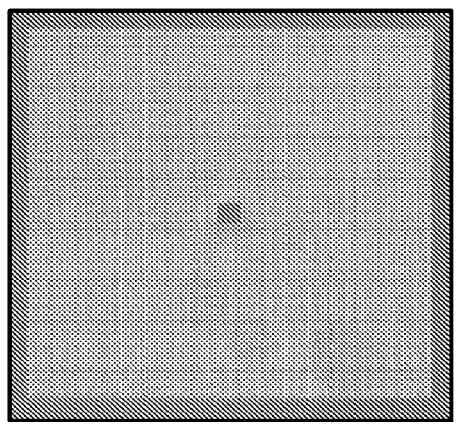
FIG. 8 illustrates the co-localization of small SNAPs on a chip.
Figure 8:
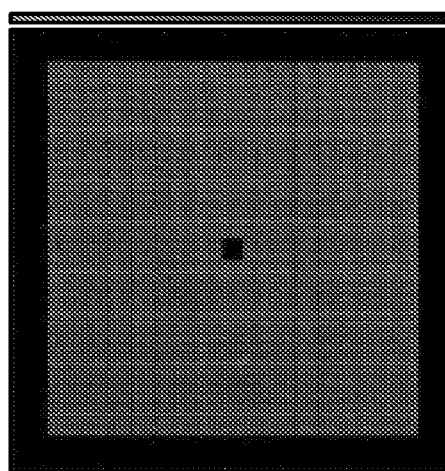
Figure 8:
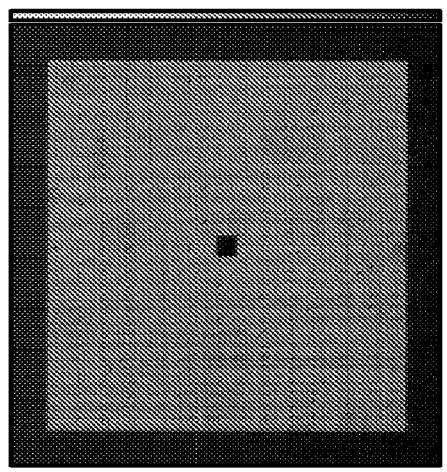

Images were taken using a standard imaging protocol, and hydrodynamic radii of the SNAPs were determined to be between 25 nm and 27 nm by anion exchange chromatography. This size range may allow for multiple SNAPs to occupy each feature in some applications. These small SNAPs were observed to co-localize within a single feature, as seen in FIG. 8. In this example, SNAPs were applied to an array and imaged (SNAP 1 on the bottom panel, SNAP 2 in the middle panel), and co-localization was determined by merging the images (top panel).

Figure 9:
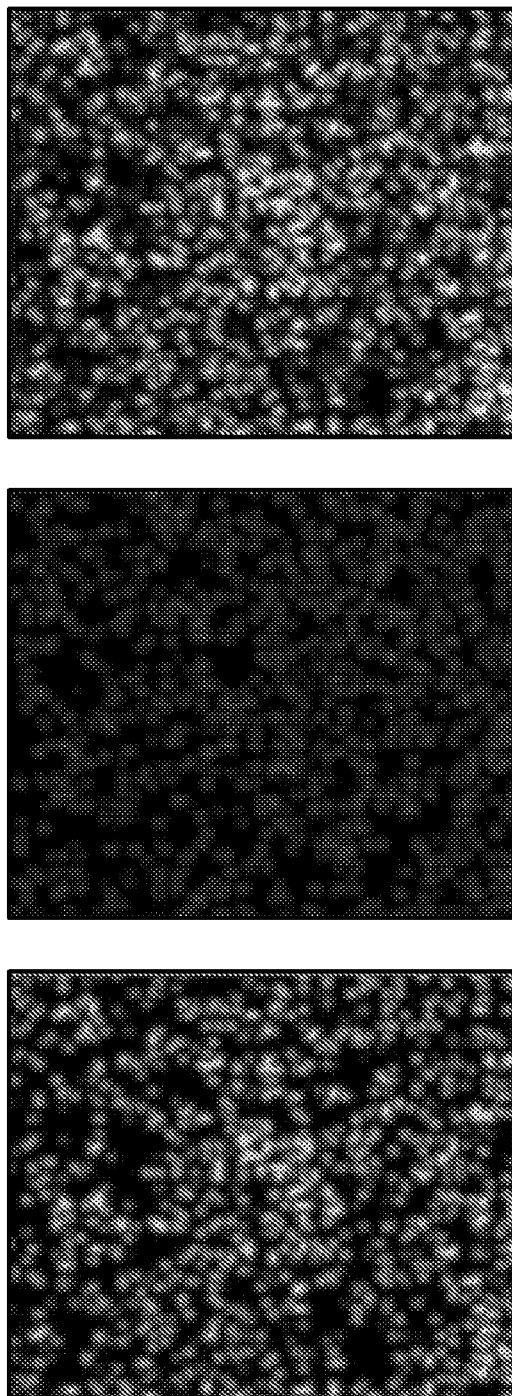
FIG. 9 illustrates the absence of co-localization of large SNAPs on a chip.

In an additional experiment, larger SNAPs were applied to a chip surface. In this case, the large SNAPs arranged themselves on the chip surface, thus achieving a "single occupancy of features." FIG. 9 shows SNAPs having a large hydrodynamic radius applied to a chip having features. The SNAPs were imaged in the bottom (SNAP1) and middle (SNAP2) images, and these images are overlaid (SNAP 1 and SNAP 2) in the top image. Significant co-localization was not observed. Thus, when SNAPs are larger in size, they can sit on the features with very little co-localization. In contrast, when SNAPs are smaller in size, they can co-localize to features in some cases.

To determine an appropriate size range for SNAPs, SNAP occupancy on array can be measured. This can be measured as brightness vs. dilution.

Figure 10:
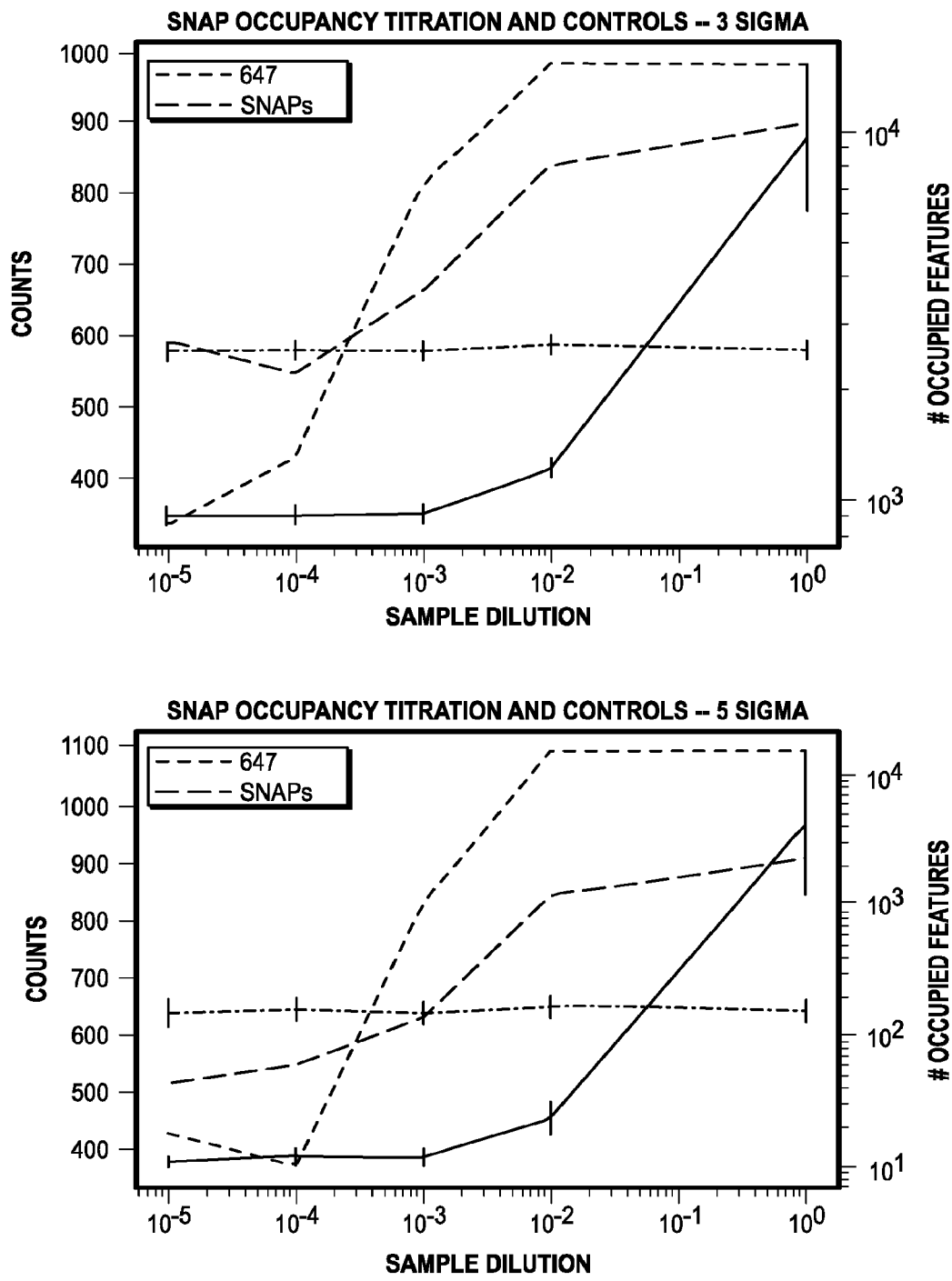
FIG. 10 illustrates the counts and number of features occupied when a titration of SNAPs is applied to a chip.
Figure 10:
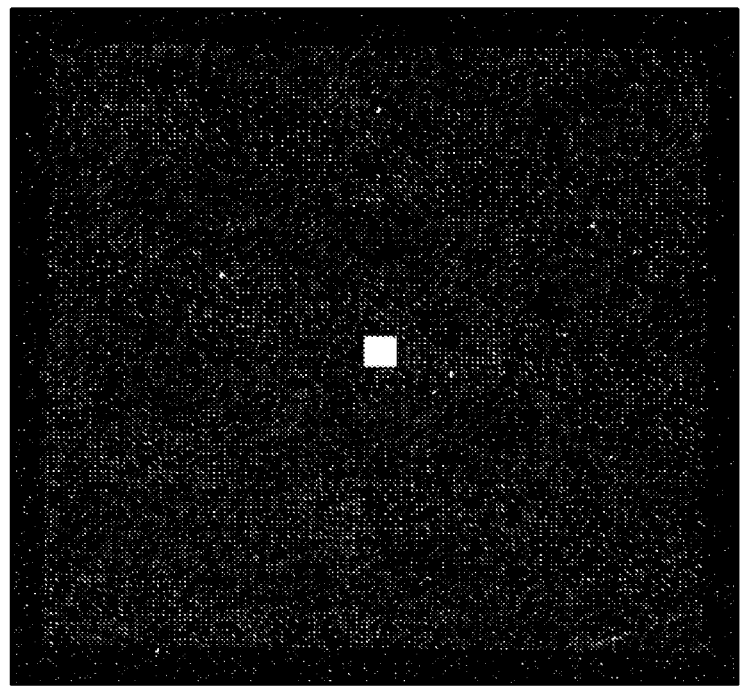
Figure 11:
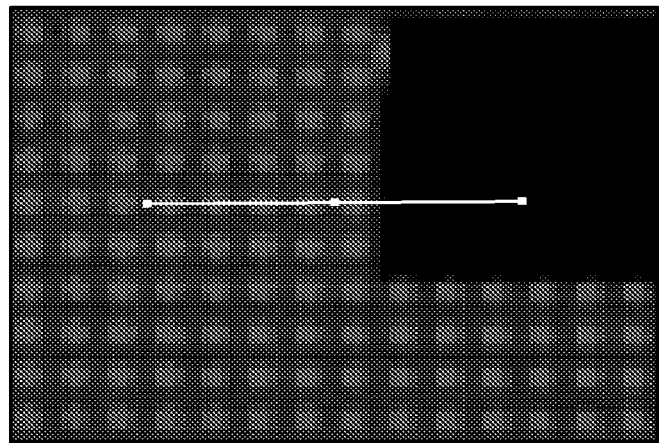
FIG. 11 illustrates the brightness of a batch of SNAPs.
Figure 11:
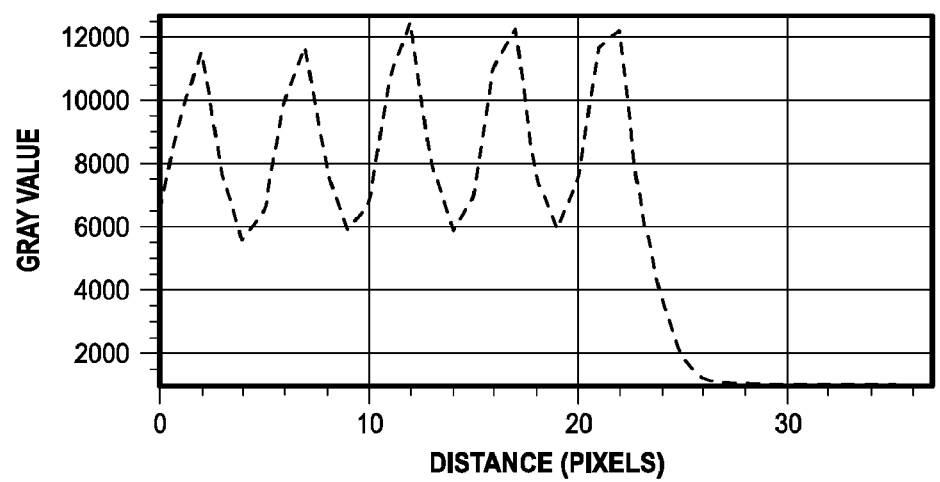

SNAPs were titrated to dilutions ranging between $10^{-5}$ and $10^0$ and applied to an array and signals were measured using dynamic light scattering. For each dilution, the number of counts and number of features occupied by a SNAPs was determined (FIG. 10). The dark lines represent a fluorescent control, while the light lines represent the SNAPs. The dotted lines represent the number of features occupied, while the solid lines represent the number of counts. Different signal trends for small molecules were observed for dye vs. SNAPs on the array.

A constant number of counts was recorded for the SNAPs (solid light line) regardless of dilution factor, which can suggest discrete occupancy of the SNAPs on features of the array.

The apparent number of occupied features was observed to change with detection threshold (dotted light line). This can suggest that the number of features occupied can be a function of the dilution. A receiver operating characteristic (ROC) curve can be developed for detection sensitivity and specificity.

SNAPs produced can be a variety of sizes. In some cases, SNAPs can be about 1 nm, 10 nm, 20 nm, 30 nm, 40 nm, 50 nm, 60 nm, 70 nm, 80 nm, 90 nm, 100 nm, 150 nm, 200 nm, 250 nm, or 300 nm in diameter. The diameter can be a major diameter, a minor diameter, or an average diameter. In some cases, SNAPs can be produced such that SNAPs having a range of diameters can be produced.

Example 5: Brightness of SNAPs

A batch of SNAPs were separately applied to an array having features and imaged using a standard imaging protocol. with a maximum grey value of about 12,000 and a difference in grey value between areas having and not having SNAPs of about 6,000, as measured by the variations in gray value across the array. Thus, SNAPs are able to bind to the array, and conjugated SNAPs can and be detected.

Example 6: Measurement of the Concentration of SNAPs

After the SNAPs are concentrated, the concentration of the SNAPs can be measured. For example, amine conjugated SNAPs can be quantitated using an o-phthaldialdehyde (OPA) free amine reaction, as shown in the top left of FIG. 12. Briefly, OPA can react with the amine to enable fluorescent detection, and can enable quantitation when a standard curve (e.g. PolyT amine serial dilutions between 0 and 100 µM, bottom left of FIG. 12) is performed.

Figure 12:
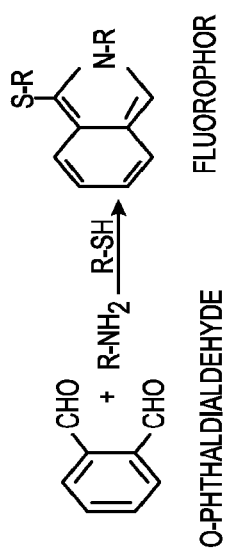
FIG. 12 illustrates the measurement of the concentration of SNAPs using an OPA assay.
Figure 12:
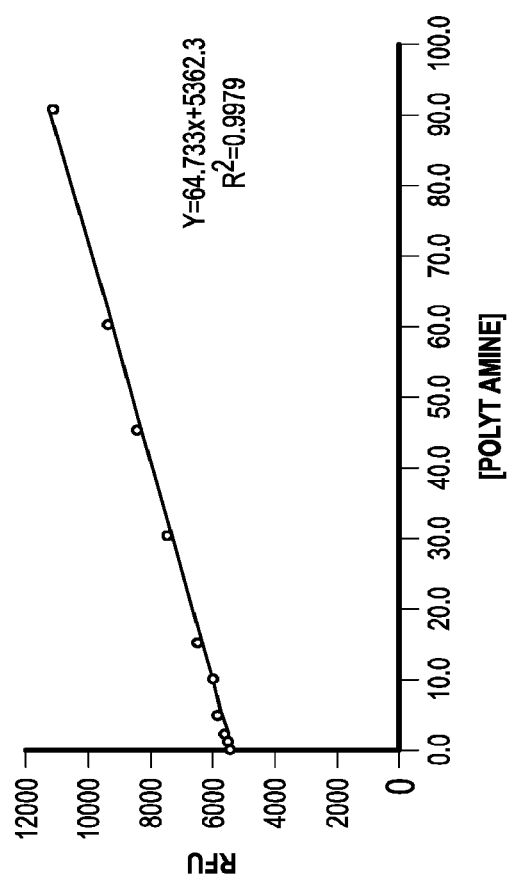
Figure 12:
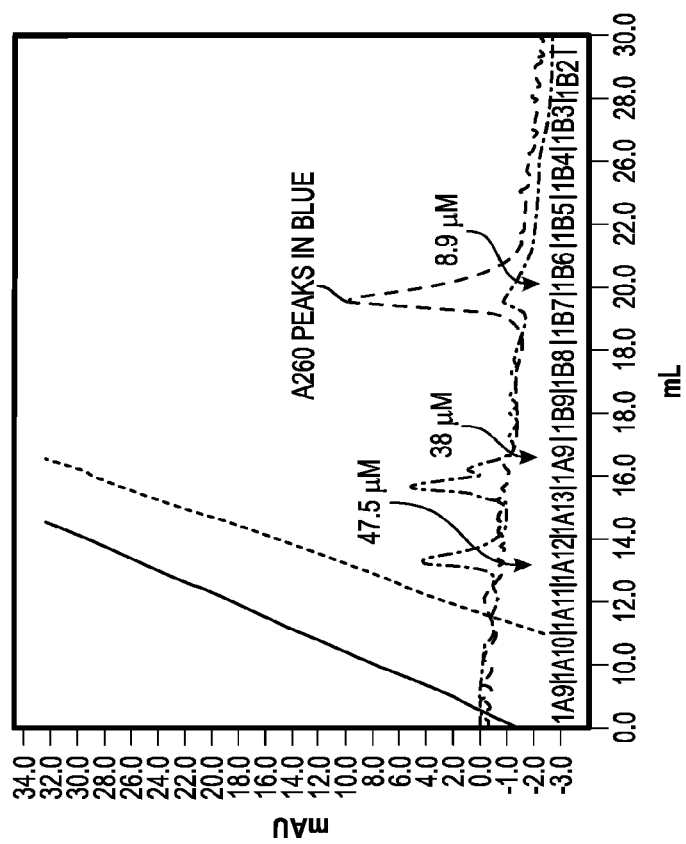
Figure 13:
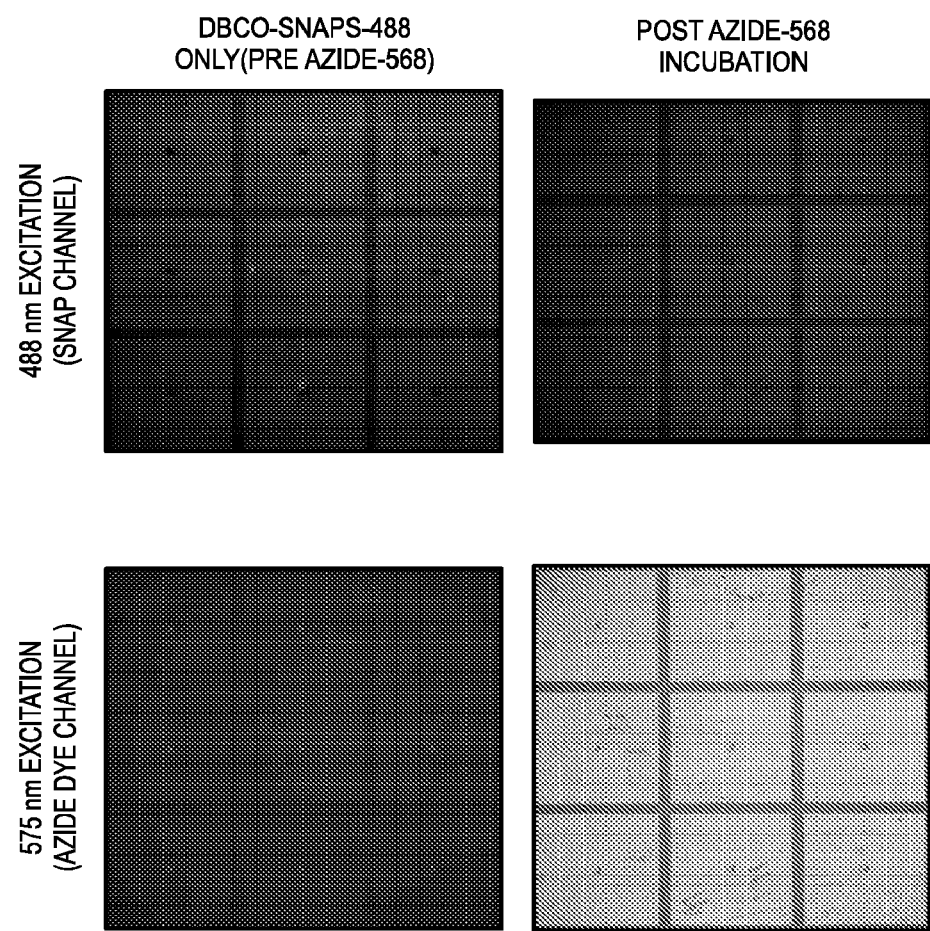
FIG. 13 illustrates fluorescent images at 488 nm and 568 nm chips having SNAPs pre- and post-conjugation with Azide-AlexaFluor 568.

The fluorescence resulting from such a reaction in three separate batches of SNAPs was measured at Ex/Em: 380 nm/460 nm, as shown in FIG. 12 (right). The A260 (absorbance at 260 nm) was quantified, and applied to the standard curve to determine the concentration of each batch. The three batches were determined to have concentrations of 47.5 µM, 38 µM, and 8.9 µM. Another batch was determined to have a concentration of 63.6 µM (data not shown). This assay can measure the concentrations of SNAPs at least in the range of 1 µM and 100 µM. In some cases, a sample of SNAPs can be diluted as necessary to fit into this range. Using this assay, relatively small amounts of amine modified DNA (e.g. SNAPs) can be measured.

Example 7: SNAP Conjugation #1

Figure 14:
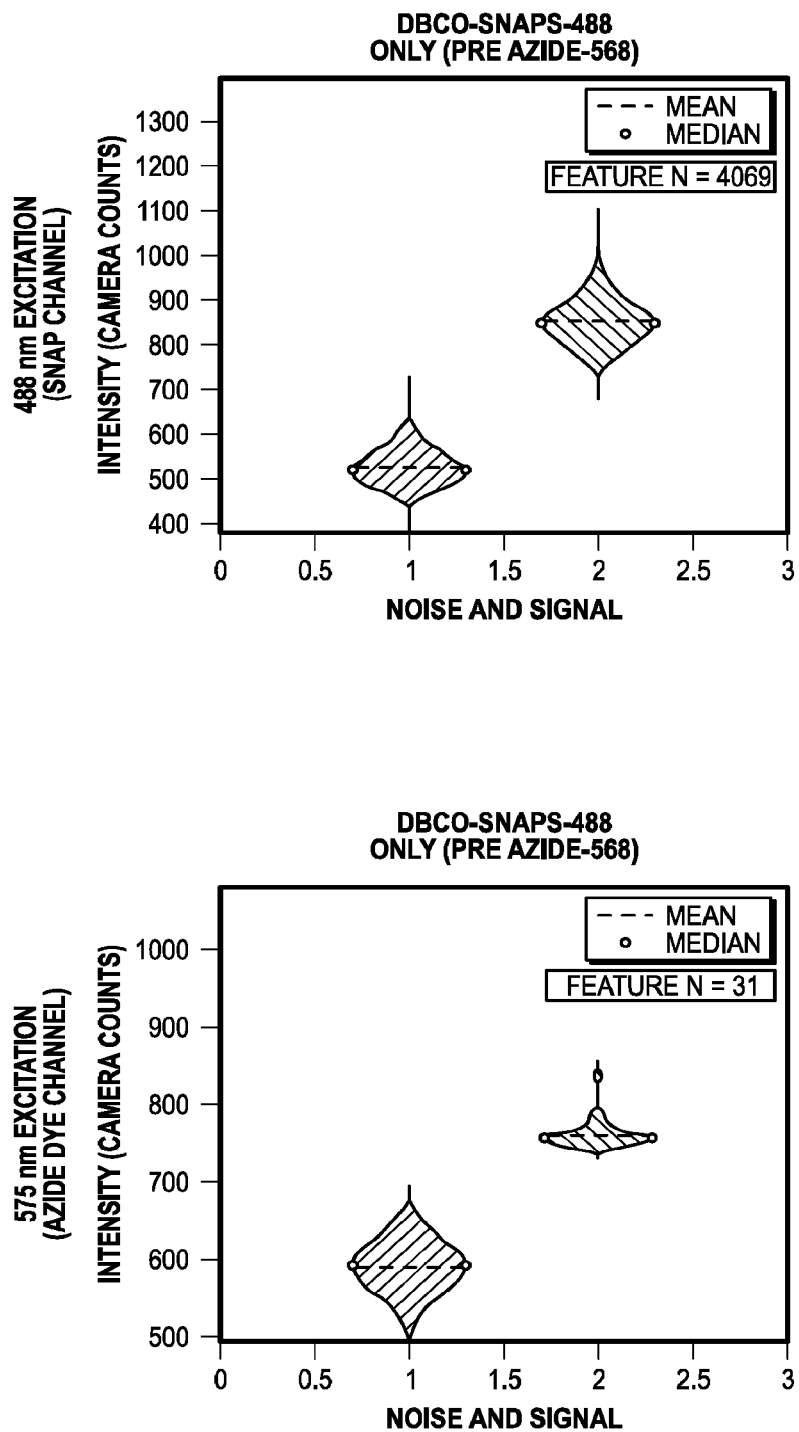
FIG. 14 illustrates quantification of the intensity from fluorescent images at 488 nm and 575 nm chips having SNAPs pre- and post-conjugation with Azide-AlexaFluor 568.
Figure 14:
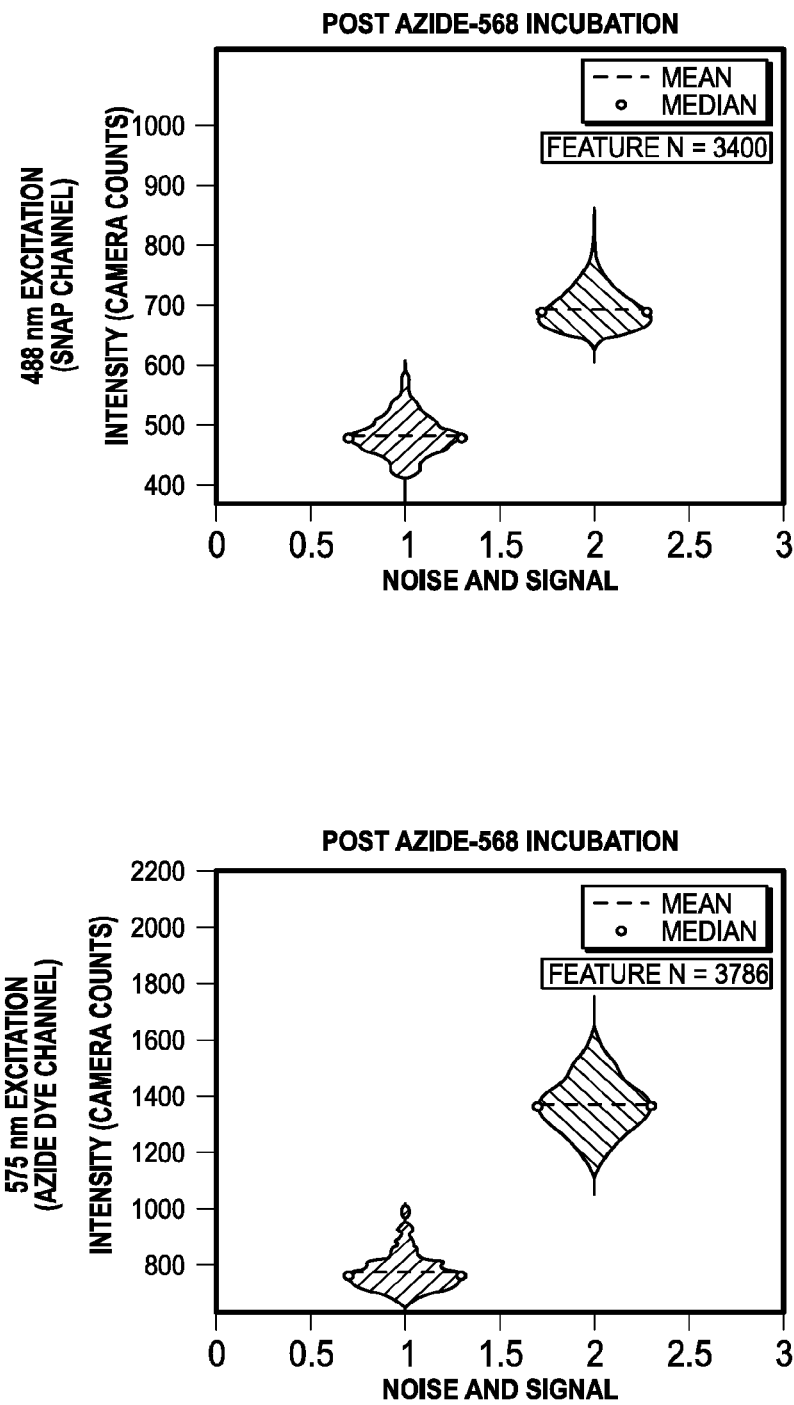

An experiment was performed such that click conjugation of Azide-AlexaFluor 586 to a SNAP was carried out on a chip. DBCO-SNAPs (488) (SNAPs having a DBCO group conjugated to a dye that can fluoresce at 488 nm) was immobilized onto an array by flow, and images were acquired at 488 nm (SNAP channel) and 575 nm (Azide dye channel). Then, Azide-568 (Azide-AlexaFluor 568), which can fluoresce at 568 nm, was incubated on the array to allow for a conjugation reaction between the DBCO and the Azide, and the array was washed after the incubation. Following this protocol, images were again acquired at 488 nm and 575 nm to assess the extent of the DBCO-Azide reaction. After incubation, the Azide dye channel showed significantly more fluorescence than before. The SNAP channel (control) showed similar signal before and after the reaction (FIG. 14). This shows that the click conjugation between DBCO and Azide on a chip (array) can be feasible.

For both channels, pre- and post-incubation, signal to noise ratio and intensity were measured for the dark (darker shading) and bright (brighter shading) sections (FIG. 14). These data confirm that the intensity is significantly increased after the click reaction, and that the click reaction performs well on the chip.

Figure 15:
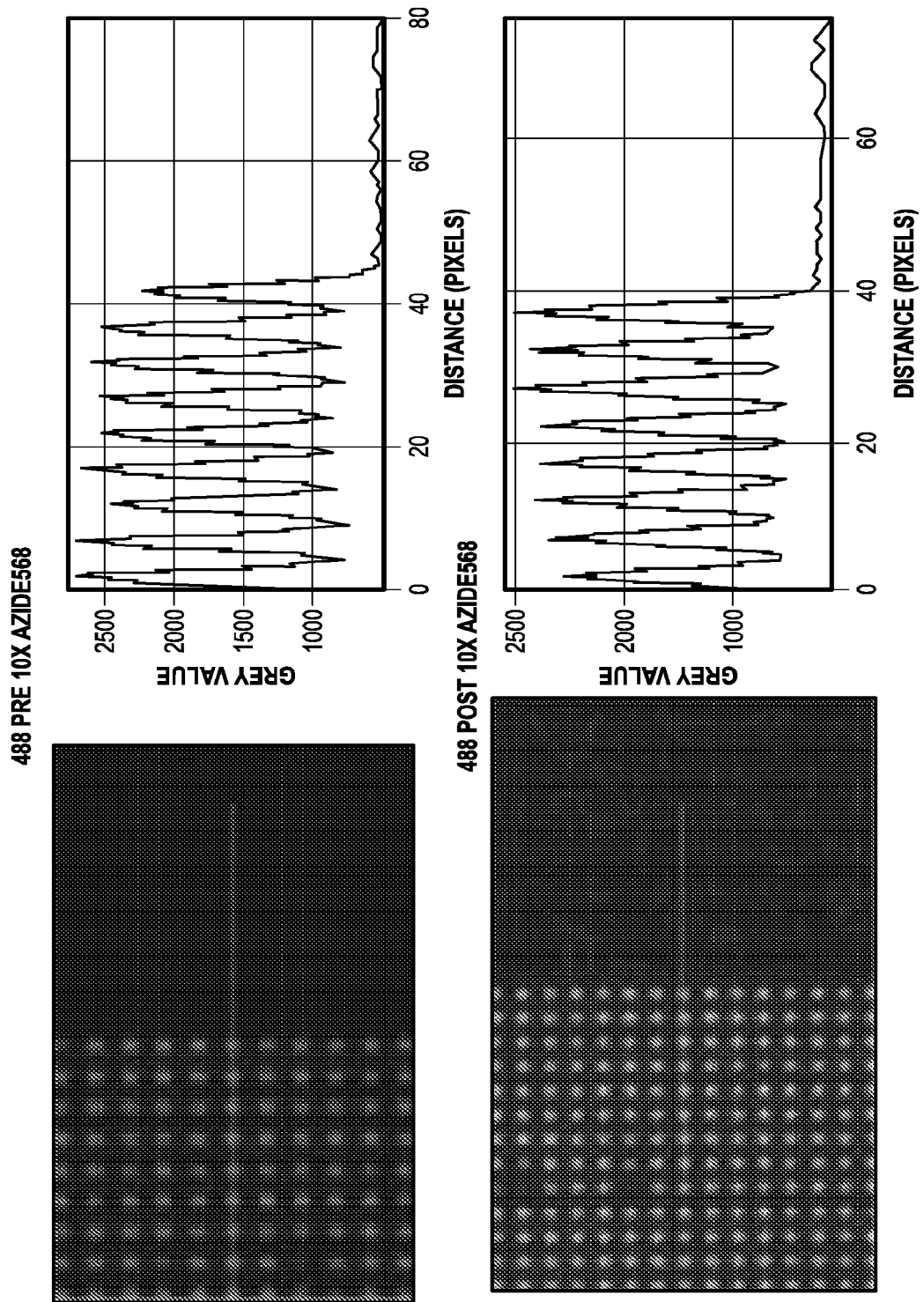
FIG. 15 illustrates fluorescent images at 488 nm of chips having SNAPs, pre- and post-incubation with Azide-AlexaFluor 568 in excess.
Figure 16:
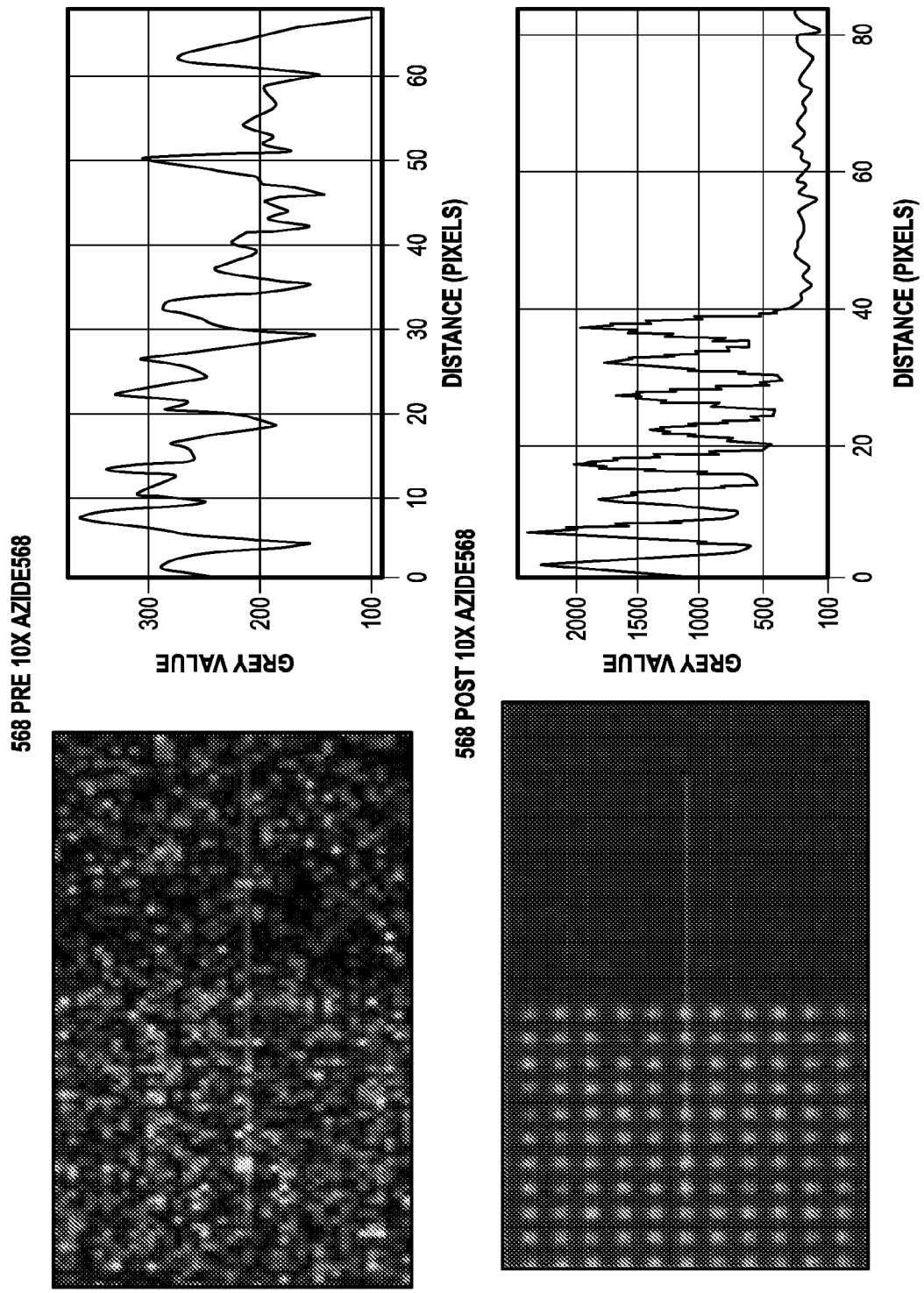
FIG. 16 illustrates fluorescent images at 568 nm of chips having SNAPs, pre- and post-incubation with Azide-AlexaFluor 568 in excess.

An additional set of SNAPs was then immobilized on arrays and conjugated to Azide-AlexaFluor 568, wherein the Azide-AlexaFluor 568 was applied at 10× excess of the total number of features. There were about 23.5 million features per flow channel. Images were taken at 488 nm and 568 nm, pre- and post-incubation, and the intensities were quantified. The intensities at 488 nm were slightly lower at 488 nm, which can be an effect of differential manual washing of block solution (FIG. 15). Intensities at 568 nm were significantly higher after incubation with 10× Azide-AlexaFluor 568 (about 2-2.5 fold), as shown in FIG. 16. In other words, uniform, localized signal at 568 nm was observed after Azide-AlexaFluor 568 was conjugated in 10× excess of the number of features per channel.

Example 8: SNAP Conjugation #2

An experiment was performed such that click conjugation of PE-conjugated (R-Phycoerythrin-conjugated) azide was carried out on a chip. SNAPs were prepared with a DBCO handle and a nucleotide capable of fluorescing at 488 nm. SNAPs were deposited on a chip surface and allowed to incubate for 1 hour to attach to the chip surface. The chip was incubated for between 15 minutes and 30 minutes with a blocking buffer, and PE (1 mg/ml) with Azide handles on Amines was flown over the chip such that there was a 1000× molar excess of PE SNAPs. The chip was then incubated overnight. The channels were then washed with phosphate buffered saline with 2% tween (PBST) and imaged.

Figure 17:
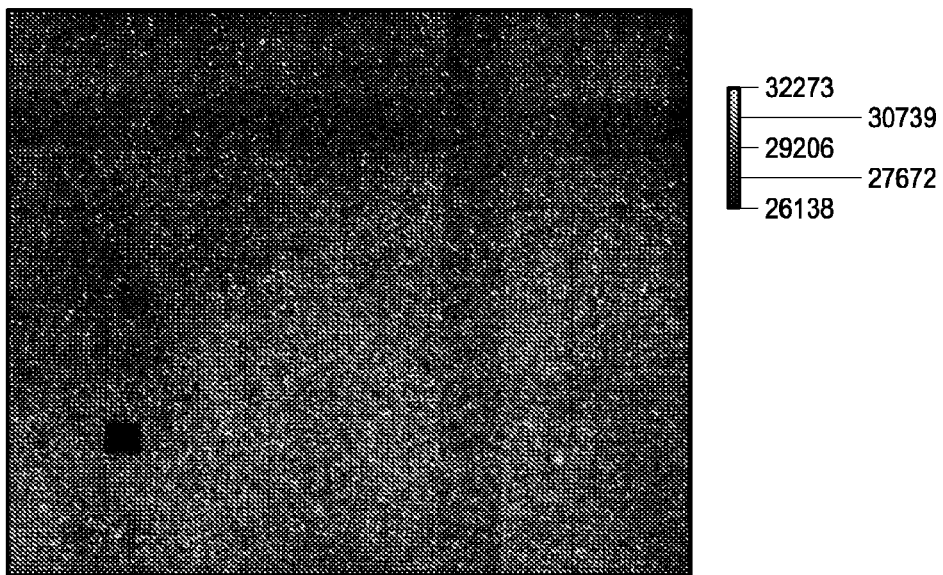
FIG. 17 illustrates the fluorescent image of a chip having SNAPs on the surface after click-conjugation with PE-conjugated azide.
Figure 18A:
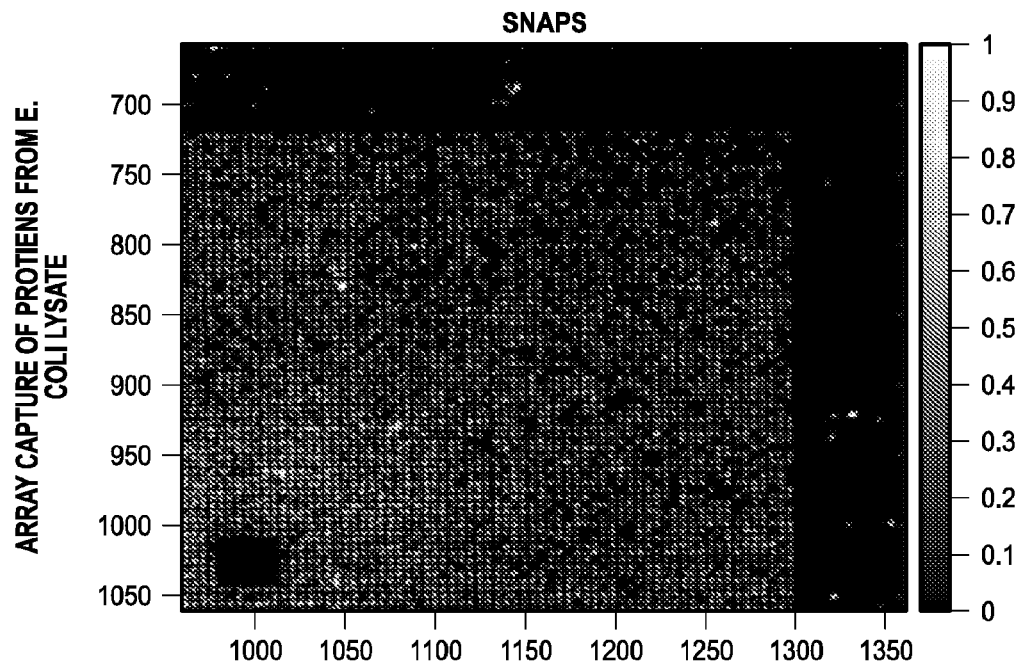
FIGS. 18A-18F illustrate the immobilization of proteins from *E. coli* lysate on an array having features which is coated with SNAPs.
Figure 18B:
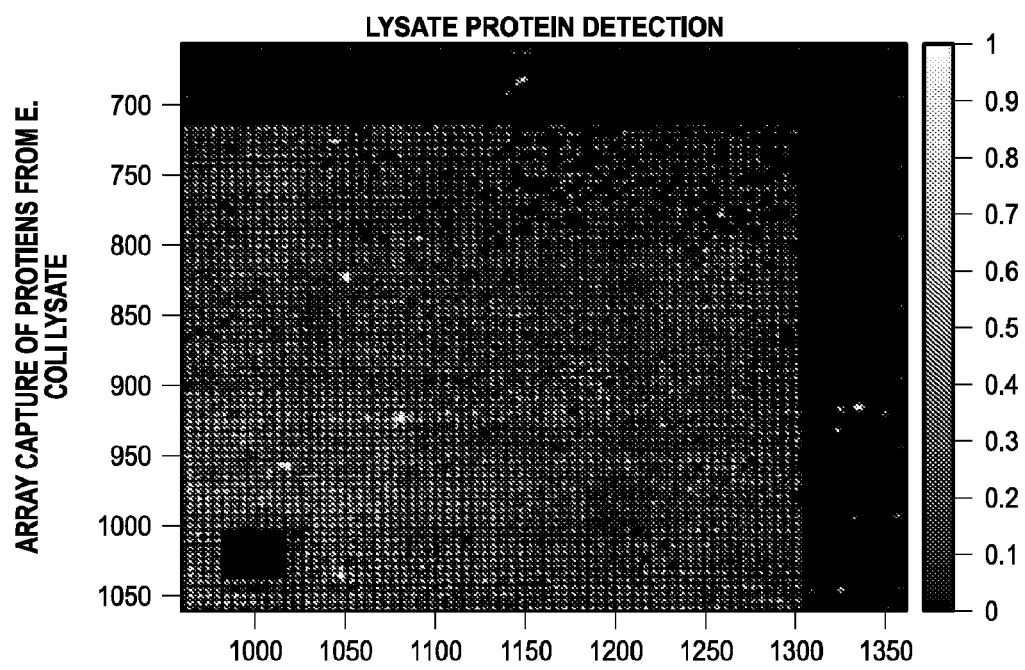
Figure 18C:
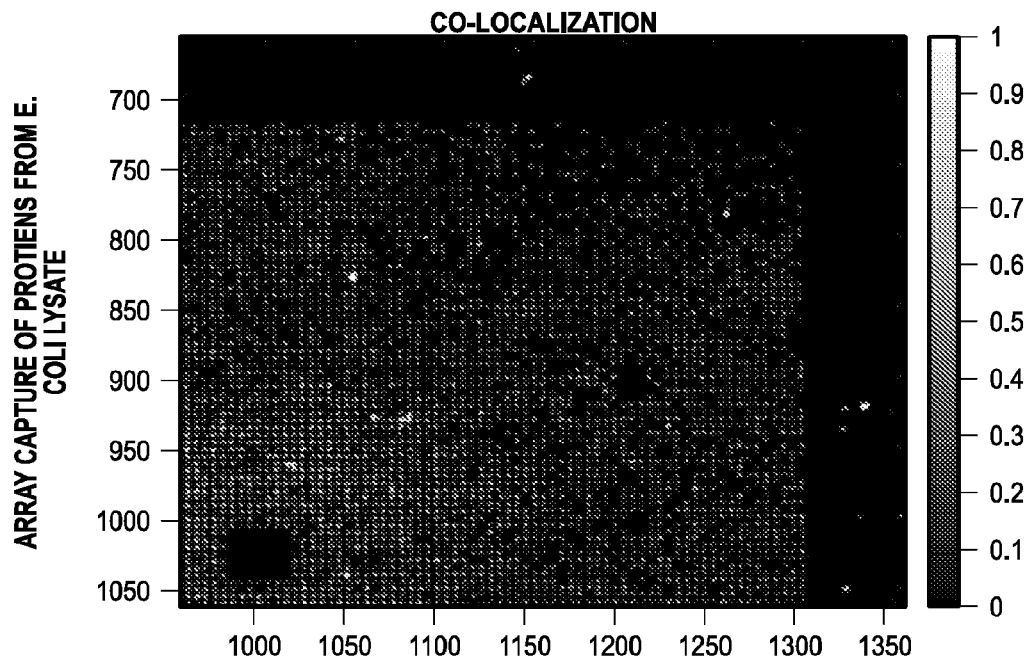
Figure 18D:
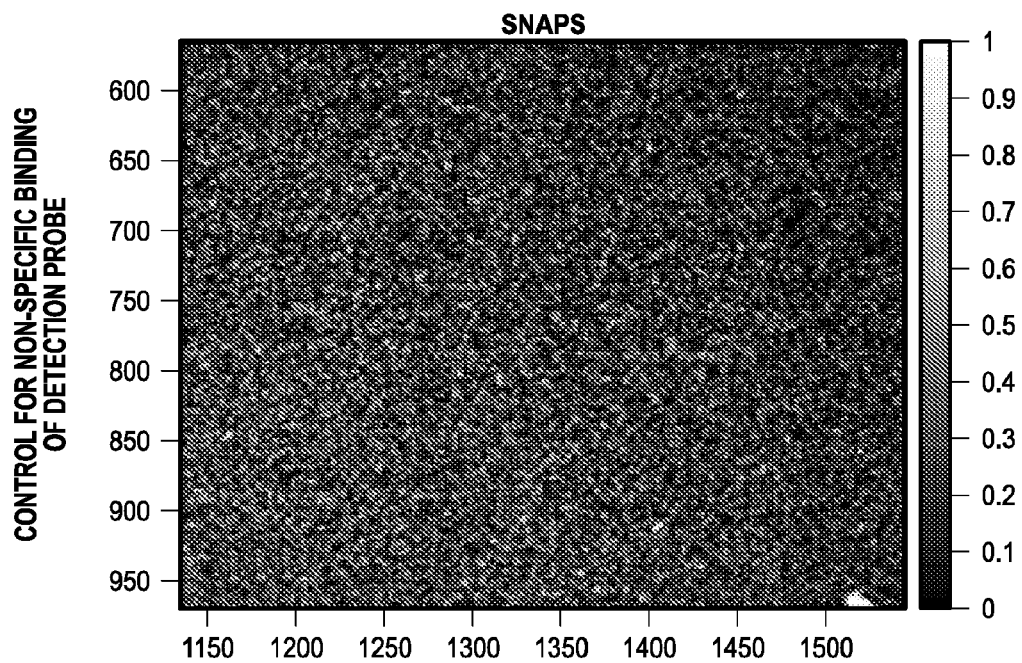
Figure 18E:
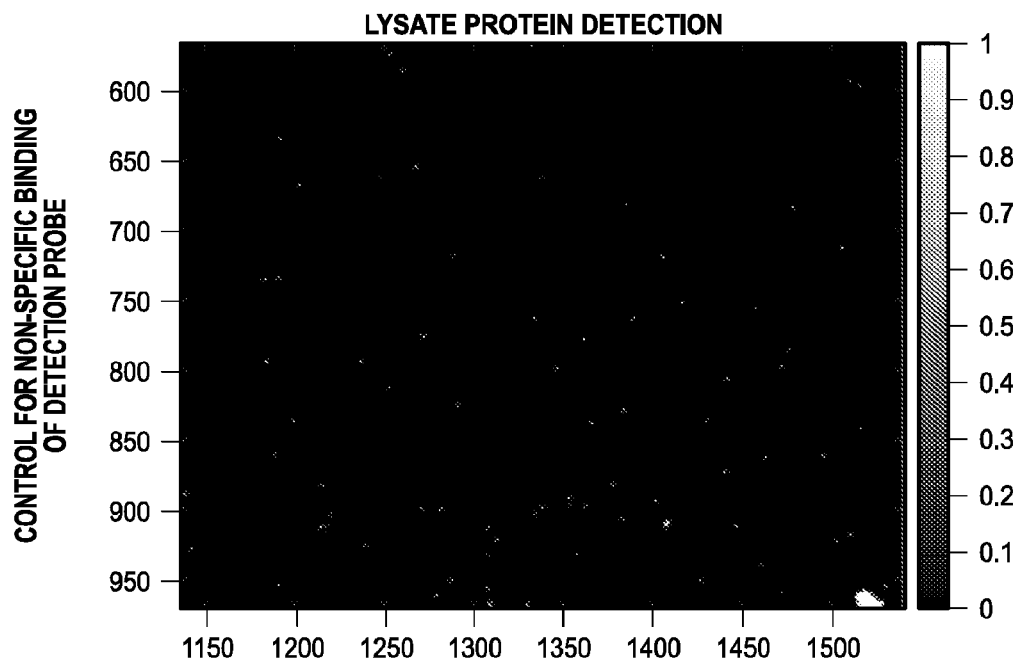
Figure 18F:
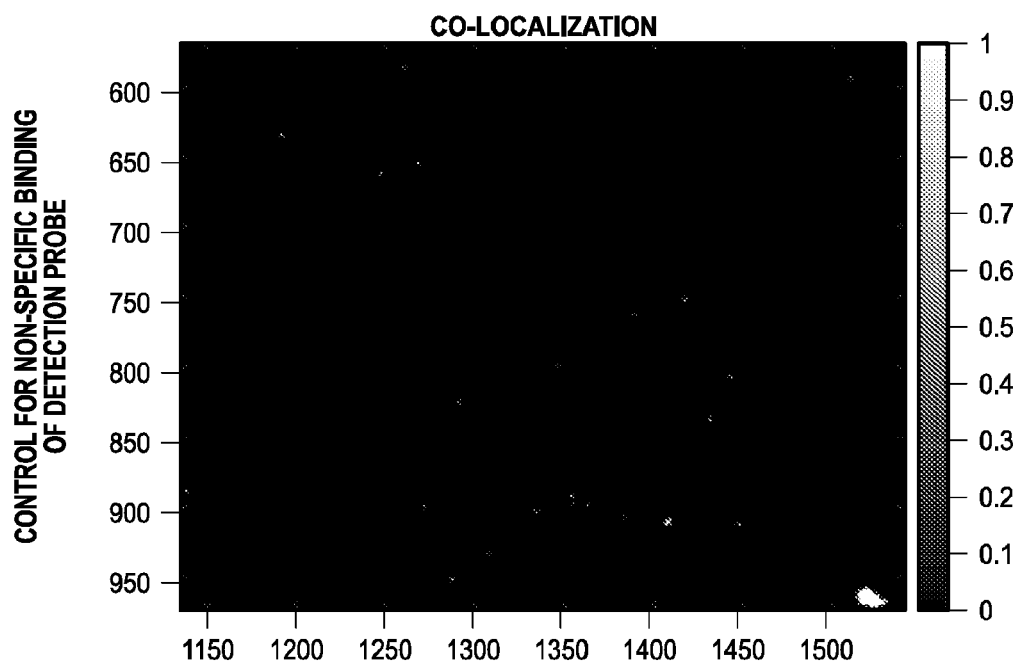
Figure 19A:
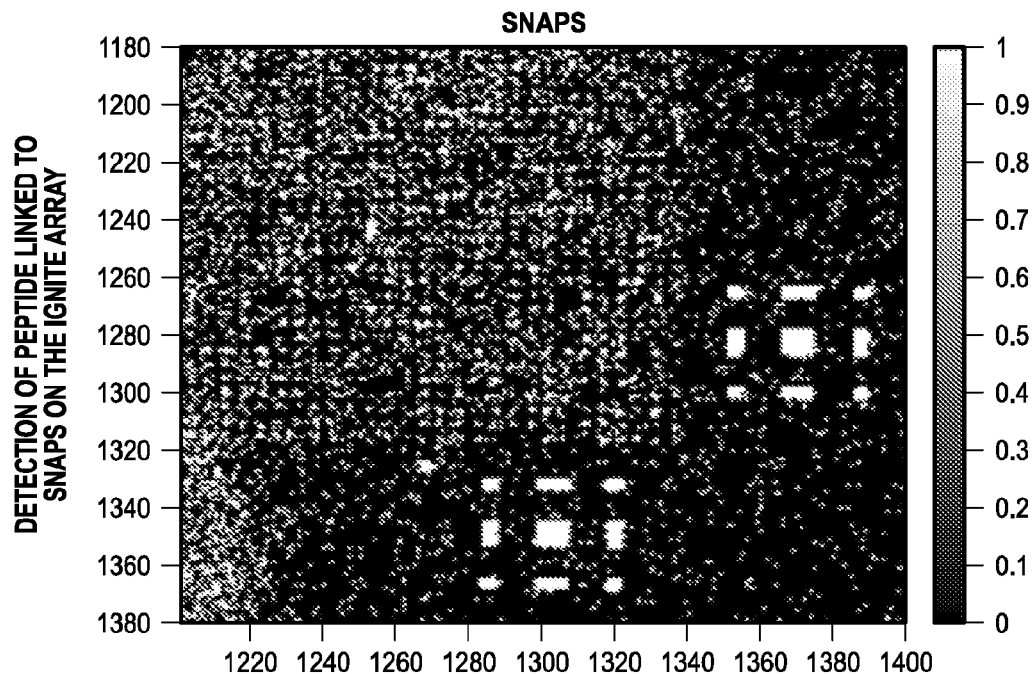
FIGS. 19A-F illustrates the specific detection of short peptides of a short trimer peptide epitope using SNAPs.
Figure 19B:
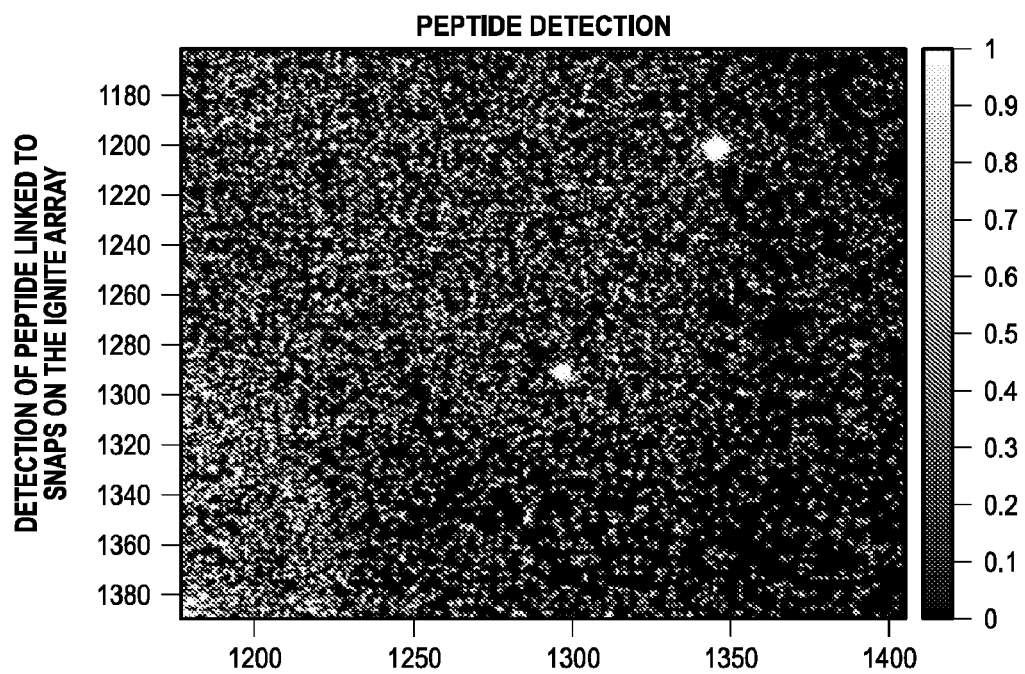
Figure 19C:
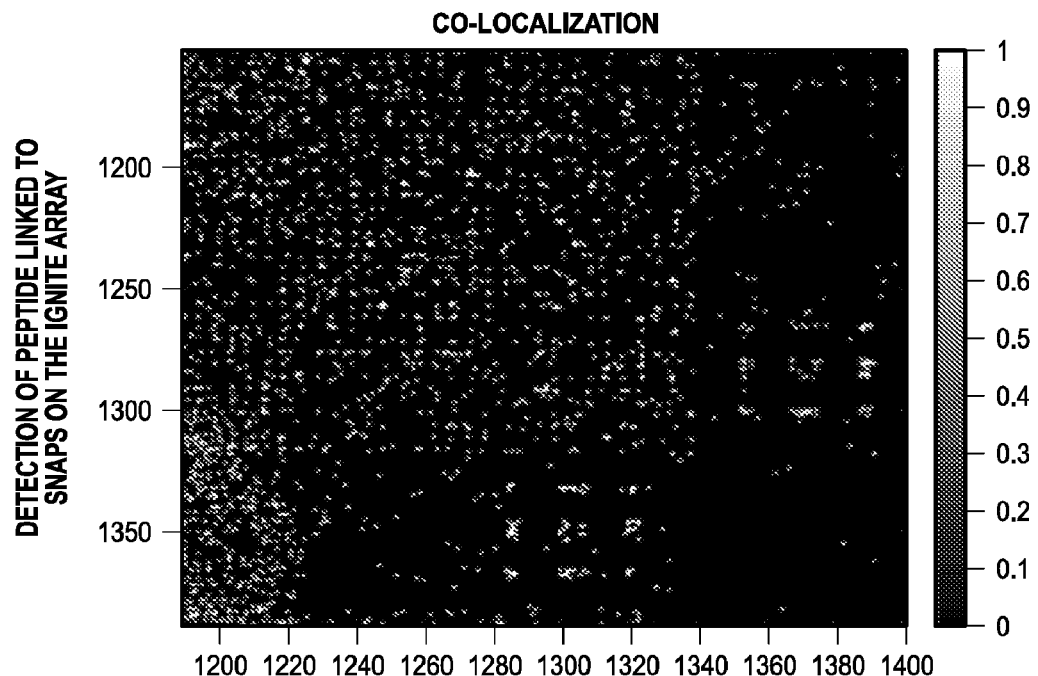
Figure 19D:
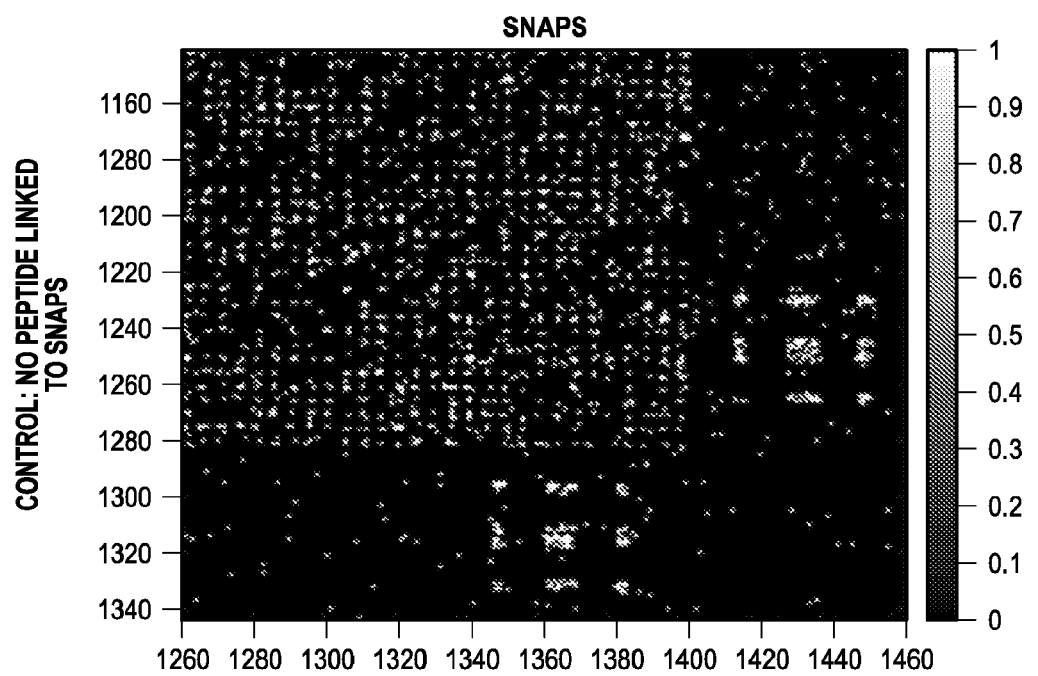
Figure 19E:
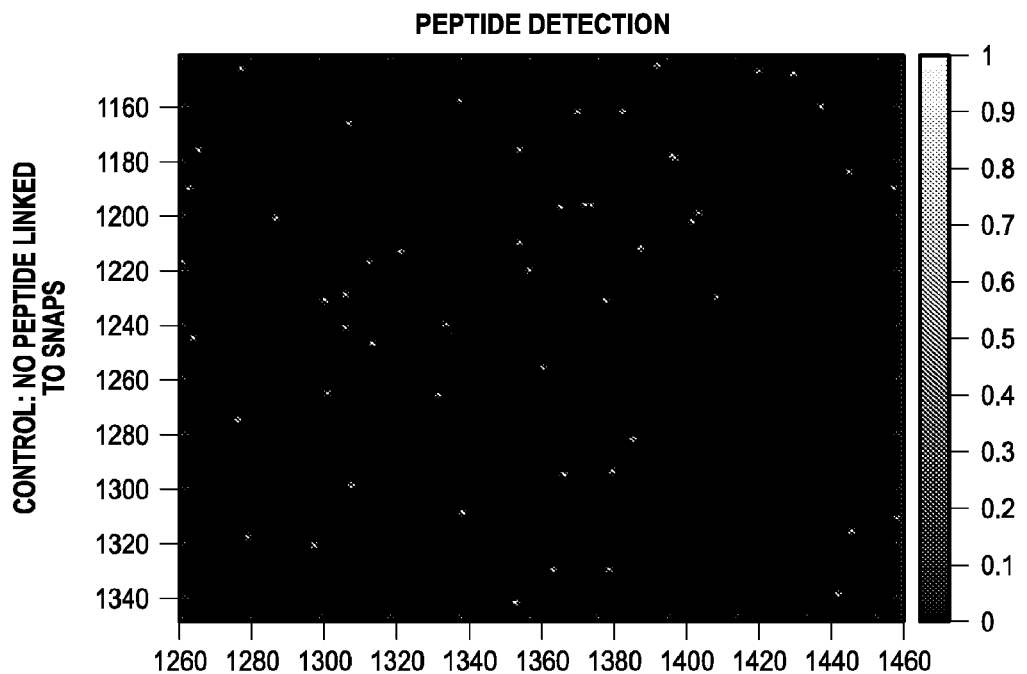
Figure 19F:
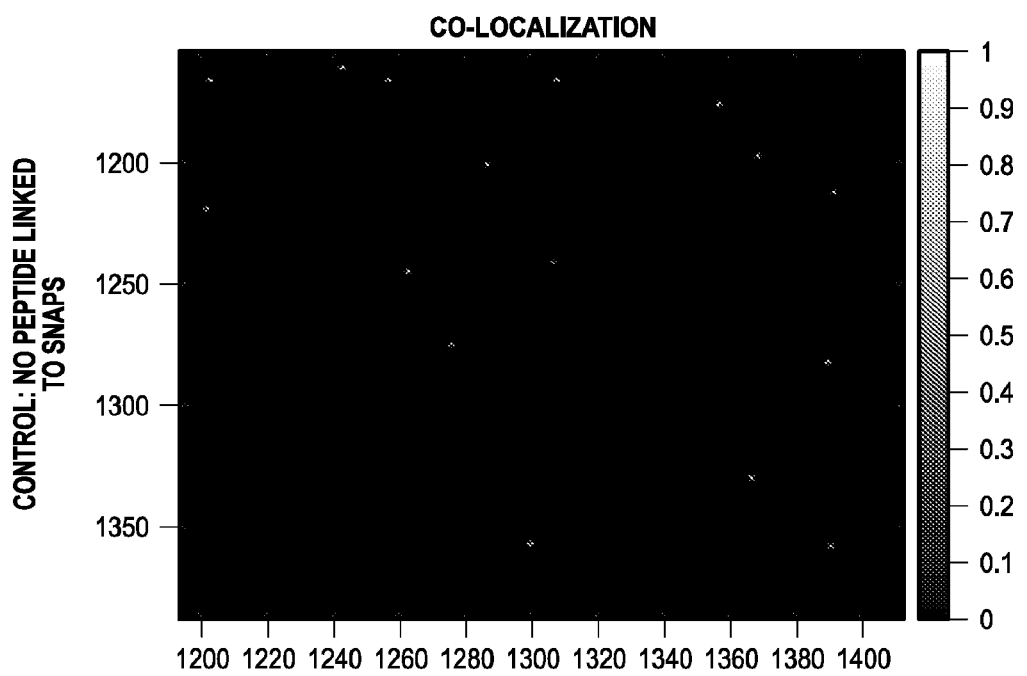

The image is shown in FIG. 17. Overall, there was a high PE signal throughout the flow channel, which can suggest an apparently high non-specific binding. A punctate signal, or an on and off feature, was observed. The on feature was observed to be typically higher by approximately 2000 counts. DBCO SNAPs were present on features, and produced a signal which was low compared with the signal from the PE. In some cases, the batch of SNAPs can be optimized e.g. by improving the quality and increasing the concentration to yield even better results. A titration series (titrating amount of PE used) can be performed as well. In addition, optimization of the blocking procedure can improve results.

Example 9: Biotinylated Click Handled Lysate Conjugation

SNAPs prepared with a DBCO handle can be deposited on a chip surface and allowed to incubate sufficiently long to attach to the chip surface. The chip can be then incubated for between 15 minutes and 30 minutes with a blocking buffer.

Lysate can be biotinylated and handled with an Azide click modifier. The biotinylated Lysate can be flown over the chip to allow click conjugation of the Lysate to the DBCO SNAPs. The Lysate can then be detected, for example via Streptavidin Lobe.

Example 10: DNA Origami

DNA origami SNAPs can be prepared for example with a DBCO handle, and can be deposited on a chip surface and allowed to incubate sufficiently long to attach to the chip surface. In some cases, the DNA origami SNAPs can be deposited on an array in a grid-like fashion. In some cases, the origami SNAPs can be about 300 nm.

In some cases, DNA origami SNAPs can provide flexibility of SNAP organization, shape, design, and sizing of the SNAPs compared with other types of SNAPs.

Example 11: Immobilization of Proteins from Lysate on Array

SNAPs were immobilized onto an array by flow. SNAP fluorescence was detected using a standard imaging protocol with a 100×100 micron field of view (FIGS. 18 A and 18 D). E. coli lysate comprising biotin handles was applied to the array, and proteins were allowed to bind the SNAPs. As a control, SNAPs were exposed to and allowed to conjugate with lysate lacking the biotin handle. Fluorescence imaging was performed using a standard imaging protocol using fluorescent streptavidin, which can bind to biotin for detection, with a 100×100 micron field of view to detect the lysate, As seen in FIGS. 18 B (biotin handle) and 18 E (control). Because the immobilized lysate does not contain the biotin tag, proteins are not detected by fluorescent streptavidin. This control demonstrates that the detection signal observed in (B) is specific to immobilized proteins (i.e., that there is no non-specific binding of the streptavidin detection reagent to the array surface).

The black and white images were multiplied to show co-localization of SNAPs and biotin handled lysate in FIGS. 18 C (biotin handle) and 18 F (control). In the co-localization images, white indicates co-localization, and black indicates no co-localization.

A fiducial can be seen in the bottom left corner of the image. HMDS lanes without feature patterning can be seen as dark stripes on the top and right edges of the field of view. SNAPs on individual features within the sub-array can be seen. Note: SNAPs are also easier to visualize because of fluorescence cross-talk into this channel from the detection channel (see B)

Example 12: Specific Detection of Short Peptide Epitopes (Trimers)

Fluorescently labeled SNAPs were immobilized onto an array by flow. A small peptide (HHH*) was allowed to conjugate with the SNAPs. As a control, SNAPs were immobilized to a chip and no peptide was conjugated to the SNAPs. A fluorescent aptamer that is specific for the small HHH peptide was applied. SNAP fluorescence was detected using a standard imaging protocol with a 35×35 micron field of view (FIGS. 19 A and 19 D). This field of view can show the corner of one sub-array on a chip. The immobilized SNAPs can be seen as discrete spots on the array (each of these spots is 300 nm in diameter).

Fluorescence imaging was performed in the same region in a different fluorescence channel which can detect the aptamer, using a standard protocol to detect the peptide (FIGS. 19 B (peptide) and 19 E (no peptide control)).

The black and white images were multiplied to show co-localization of SNAPs and the HHH peptide. FIGS. 19 C (peptide) and 19 F (no peptide control) shows the co-localization of fluorescence between the SNAP-peptide channel and the aptamer detection channel. Co-localization can indicate successful binding and identification of the HHH peptide on SNAPs on the features of the array. Because there is no bound aptamer in FIG. 19 F, the merge image for the control image shows no co-localization.

In the no peptide control images, because the HHH peptide was unable to bind to the SNAPs on the array, there is no detection of HHH in the aptamer fluorescence channel. Thus, this result can confirm that the HHH peptide was 1) directly attached to the SNAPs and 2) the signal observed in the aptamer channel can be observed only when the target peptide is present.

Two chrome fiducial marks can be seen in the lower right corner of the image. The darker lanes in the image are HMDS-coated areas that do not contain patterned features.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
   (a) obtaining a structured nucleic acid particle that is covalently attached to only one protein molecule of interest, wherein said structured nucleic acid particle comprises a self-hybridized region, and wherein said structured nucleic acid particle comprises nucleic acid origami; and
   (b) then attaching said structured nucleic acid particle to an attachment site on a solid support, such that said attachment site is attached to said only one protein molecule of interest via said structured nucleic acid particle.

2. The method of claim 1, wherein said solid support comprises an array of attachment sites, and wherein said attachment site is separated from any other attachment site of said array by a distance that is greater than the diameter of said structured nucleic acid particle.

3. The method of claim 2, wherein said attachment sites of said array of attachment sites are positively charged.

4. The method of claim 1, wherein said structured nucleic acid particle comprises a photocleaveable bond that covalently attaches said only one protein molecule of interest to said attachment site.

5. The method of claim 4, further comprising cleaving said photocleavable bond of said structured nucleic acid particle, thereby separating said only one protein molecule of interest from said attachment site.

6. The method of claim 1, wherein said solid support is passivated prior to attaching said structured nucleic acid particle to said attachment site.

7. The method of claim 1, wherein said structured nucleic acid particle has a diameter between 10 nanometers (nm) and 50 micrometers (μm).

8. The method of claim 1, wherein said structured nucleic acid particle has a diameter between 10 nm and 5 μm.

9. The method of claim 1, wherein said attachment site on said solid support is positively charged and said structured nucleic acid particle is attached to said attachment site on said solid support through an electrostatic interaction.

10. The method of claim 1, wherein said structured nucleic acid particle is attached to said attachment site on said solid support through a covalent interaction between a functional group of said structured nucleic acid particle and a functional group of said attachment site.

11. The method of claim 1, wherein the diameter of said attachment site is less than the diameter of said structured nucleic acid particle.

12. The method of claim 1, wherein said structured nucleic acid particle occludes binding of more than one protein to the attachment site.

13. The method of claim 1, further comprising covalently attaching said only one protein molecule of interest to said structured nucleic acid particle prior to step (a).

14. The method of claim 1, wherein said nucleic acid origami comprises deoxyribonucleic acid (DNA).

15. The method of claim 1, wherein said nucleic acid origami comprises RNA.

16. The method of claim 1, wherein said nucleic acid origami is covalently attached to said only one protein molecule of interest by a linker.

17. The method of claim 16, wherein said nucleic acid origami comprises a landing surface that contacts said attachment site and wherein said linker positions the only one protein molecule of interest distal from said solid support relative to said landing surface.

18. The method of claim 16, wherein said linker comprises a region of a double stranded DNA.

19. The method of claim 1, wherein said attachment site is in an array of attachment sites on said solid support.

20. The method of claim 1, further comprising non-covalently binding said single only one protein molecule of interest to a second protein.

21. The method of claim 1, further comprising detecting said single only one protein molecule of interest using a structured nucleic acid particle having an attached probe and a fluorescent moiety.

22. The method of claim 1, wherein said attachment site has a diameter that is larger than said only one protein molecule of interest.

23. The method of claim 1, wherein said structured nucleic acid particle has a diameter between 50 nanometers and 100 micrometers.

24. The method of claim 1, wherein said structured nucleic acid particle has a diameter of at least 75 nanometers.

25. The method of claim 1, further comprising, prior to step (a), conjugating said only one protein molecule of interest to said structured nucleic acid particle by covalently attaching said structured nucleic acid particle to said only one protein molecule of interest and separating said structured nucleic acid particle unconjugated to said only one protein molecule of interest from said structured nucleic acid particle that is covalently attached to said only one protein molecule of interest.

* * * * *

```
SEQUENCE LISTING

<160> NUMBER OF SEQ ID NOS: 5

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gccagggtgc gagggtttgt ttcattgctt cacgccctta ccctcgcacc ctggcacgg      59

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcccacggtg gcacctcgca cct                                             23

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcacgctgc caccctcgct tttgcgaggg tggcagcgt                            39

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcgaggtgcg aggtgccacc gtgggaccgt                                      30

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
aagggcgtga agcaatga                                                    18
```